United States Patent
Sharp et al.

(10) Patent No.: US 10,017,821 B2
(45) Date of Patent: *Jul. 10, 2018

(54) BIOMARKERS FOR DIAGNOSING ISCHEMIA

(71) Applicant: The Regents of the University of California, Oakland, CA (US)

(72) Inventors: Frank Sharp, Davis, CA (US); Glen C Jickling, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/226,844

(22) Filed: Aug. 2, 2016

(65) Prior Publication Data

US 2017/0029891 A1    Feb. 2, 2017

Related U.S. Application Data

(63) Continuation of application No. 14/370,709, filed as application No. PCT/US2013/020240 on Jan. 4, 2013, now Pat. No. 9,410,204.

(60) Provisional application No. 61/584,232, filed on Jan. 7, 2012.

(51) Int. Cl.
    *C12Q 1/68* (2018.01)
    *C12Q 1/6883* (2018.01)
    *G01N 33/68* (2006.01)

(52) U.S. Cl.
    CPC ....... *C12Q 1/6883* (2013.01); *G01N 33/6893* (2013.01); *C12Q 2600/118* (2013.01); *C12Q 2600/158* (2013.01); *G01N 2800/2871* (2013.01); *G01N 2800/324* (2013.01); *G01N 2800/50* (2013.01); *G01N 2800/7019* (2013.01)

(58) Field of Classification Search
    CPC ............ C12Q 1/6883; C12Q 2600/158; G01N 33/6893; G01N 2800/2871; G01N 2800/324; G01N 28/50; G01N 2800/7019
    See application file for complete search history.

(56) References Cited

U.S. PATENT DOCUMENTS

| 9,057,109 | B2 | 6/2015 | Chang |
| 9,200,322 | B2 | 12/2015 | Barr et al. |
| 9,410,204 | B2 * | 8/2016 | Sharp .................. C12Q 1/6883 |

(Continued)

FOREIGN PATENT DOCUMENTS

| WO | WO 02/12892 | 2/2002 |
| WO | WO 03/016910 | 2/2003 |

(Continued)

OTHER PUBLICATIONS

PCT International Search Report and Written Opinion dated Jul. 25, 2008 issued in PCT/US2008/062064.

(Continued)

*Primary Examiner* — Reza Ghafoorian
(74) *Attorney, Agent, or Firm* — Weaver Austin Villeneuve & Sampson LLP

(57) ABSTRACT

The present invention provides methods and compositions for diagnosing and predicting the occurrence of ischemia. For example, the present invention provides methods and compositions for diagnosing and predicting the risk and cause of transient neurological events (TNE) as ischemic or non-ischemic.

11 Claims, 3 Drawing Sheets

(56) References Cited

U.S. PATENT DOCUMENTS

| | | | |
|---|---|---|---|
| 9,803,243 | B2 | 10/2017 | Sharp et al. |
| 2001/0053519 | A1 | 12/2001 | Fodor et al. |
| 2002/0115120 | A1 | 8/2002 | Kapeller-Libermann et al. |
| 2003/0119064 | A1 | 6/2003 | Valkirs et al. |
| 2003/0199000 | A1 | 10/2003 | Valkirs et al. |
| 2004/0191783 | A1 | 9/2004 | Leclercq et al. |
| 2004/0203083 | A1 | 10/2004 | Buechler et al. |
| 2006/0046259 | A1 | 3/2006 | Baird et al. |
| 2006/0078882 | A1 | 4/2006 | Zetter et al. |
| 2007/0042425 | A1 | 2/2007 | Hochstrasser et al. |
| 2007/0050146 | A1 | 3/2007 | Bentwich et al. |
| 2007/0280917 | A1 | 12/2007 | Helgadottir |
| 2009/0148933 | A1* | 6/2009 | Battrell ............... B01F 11/0071 435/287.2 |
| 2009/0197774 | A1 | 8/2009 | Kozian et al. |
| 2010/0105046 | A1 | 4/2010 | Epstein et al. |
| 2010/0197518 | A1 | 8/2010 | Xu et al. |
| 2010/0216115 | A1 | 8/2010 | Yan et al. |
| 2012/0015904 | A1 | 1/2012 | Sharp et al. |
| 2012/0065087 | A1 | 3/2012 | Sharp et al. |
| 2012/0316076 | A1 | 12/2012 | Sharp et al. |
| 2015/0018234 | A1 | 1/2015 | Sharp et al. |
| 2016/0222455 | A1 | 8/2016 | Xu et al. |
| 2016/0237501 | A1 | 8/2016 | Sharp et al. |
| 2016/0265059 | A1 | 9/2016 | Sharp et al. |
| 2016/0289765 | A1 | 10/2016 | Sharp et al. |

FOREIGN PATENT DOCUMENTS

| | | |
|---|---|---|
| WO | WO 2005/116268 | 12/2005 |
| WO | WO 2006/036220 | 4/2006 |
| WO | WO 2008/137465 | 11/2008 |
| WO | WO 2010/012834 | 2/2010 |
| WO | WO 2012/009547 | 1/2012 |
| WO | WO 2012/009567 | 1/2012 |
| WO | WO 2012/121978 | 9/2012 |
| WO | WO 2013/103781 | 7/2013 |

OTHER PUBLICATIONS

PCT International Preliminary Report on Patentability dated Nov. 3, 2009 issued in PCT/US2008/062064.
PCT International Search Report and Written Opinion dated Mar. 28, 2012 issued in PCT/US2011/044062.
PCT International Preliminary Report on Patentability dated Jan. 15, 2013 issued in PCT/US2011/044062.
PCT International Search Report and Written Opinion dated Mar. 28, 2012 issued in PCT/US2011/044023.
PCT International Preliminary Report on Patentability dated Jan. 15, 2013 issued in PCT/US2011/044023.
PCT International Search Report and Written Opinion dated Oct. 24, 2012 issued in PCT/US2012/027316.
PCT International Preliminary Report on Patentability dated Sep. 10, 2013 issued in PCT/US2012/027316.
PCT International Search Report and Written Opinion dated Apr. 12, 2013 issued in PCT/US2013/020240.
PCT International Preliminary Report on Patentability dated Jul. 8, 2014 issued in PCT/US2013/020240.
Indian First Examination Report dated Dec. 13, 2016 issued in IN 3762/KOLNP/2009.
European Extended Search Report dated Mar. 16, 2011 issued in EP 10014221.5.
European Extended Search Report dated Nov. 12, 2013 issued in EP11807532.4.
European Extended Search Report dated Apr. 11, 2014 issued in EP 11 807 519.1.
"*Homo sapiens* disabled homolog 2, mitogen-responsive phosphoprotein (*Drosophila*), mRNA (cDNA clone MGC:1764 IMAGE:3504380)," Accession:BC003064.2, GI: 33870637, complete cds [Downloaded on Feb. 21, 2017 at https://www.ncbi.nlm.nih.gov/nuccore/BC003064.2?report-girevhist], 1 page.

"Affymetrix GeneChip Human Genome U133 Array Set HG-U133B," *GEO Accession viewer* (Mar. 11, 2002), XP002427171 pp. 1-4.
"Affymetrix Genechip Human Genome U133 plus 2.0 Array," *GEO Accession viewer* 7 (Nov. 7, 2003), XP002343693 pp. 1-3.
Barr et al. (2010) "Genomic biomarkers and cellular pathways of ischemic stroke by RNA gene expression profiling" *Neurology* 75:1009-1014.
Benner et al. (2001) "Evolution, language and analogy in functional genomics," *Trends in Genetics* 17(7):414-418.
Cheung et al. (2003) "Natural variation in human gene expression assessed in lymphoblastoid cells," *Nature Genetics* 33:422-425.
Cobb et al. (2002) "Sepsis gene expression profiling: Murine splenic compared with hepatic responses determined by using complementary DNA microarrays," *Crit Care Med* 30(12):2711-2721.
Crawford et al., (2007) "The biological importance of measuring individual variation," *J. Exp. Biol.* 210:1613-1621.
Davi et al. (2009) "CD40 ligand and MCP-1 as predictors of cardiovascular events in diabetic patients with stroke," *J. Atheroscler. Thromb.* 16:707-713.
Ferronato et al. (2010) "Upregulated Expression of Toll-like Receptor 4 in Peripheral Blood of Ischaemic Stroke Patients Correlates with Cyclooxygenase 2 Expression," *European Journal of Vascular and Endovascular Surgery* 41(3): 358-363.
Fung et al. (2008) "A biomarker panel for peripheral arterial disease," *Vasc. Med.* 13:217-224.
Greenbaum et al. (2003) "Comparing protein abundance and mRNA expression levels on a genomic scale," *Genome Biology* 4:117(1-8).
Haller et al. (2004) "Equivalence test in quantitative reverse transcription polymerase chain reaction: confirmation of reference genes suitable for normalization," *Anal. Biochem.* 335:1-9.
Hassan et al. (2003) "Marker of endothelial dysfunction in lacunar infarction and ischaemic leukoaraiosis," *Brain* 126:424-432.
Hou et al. (2003) "High-density DNA Microarray Analysis of Gene Expression Following Transient Focal Cerebral Ischemia in Mouse," *International Congress Series* 1252:45-56.
Jakobsen et al. (1990) "Purification of mRNA directly from crude plant tissues in 15 minutes using magnetic oligo dT microspheres," *Nucleic Acids Research*, 18(12):3669.
Jensen et al. (2008) "The promise and potential pitfalls of serum biomarkers for ischemic stroke and transient ischemic attack," *Neurologist* 14(4):243-246.
Jensen et al. (2009) "Potential biomarkers for the diagnosis of stroke," *Expert Review of Cardiovascular Therapy*, 7(4):389-93.
Jickling et al. (2010) "Biomarkers of ischemic stroke," *US Neurology*, 5(2):52-54.
Jickling et al. (Nov. 2010) "Signatures of cardioembolic and large vessel ischemic stroke," *Ann Neural.*, 68(5):681-692.
Jickling et al. (2011) "Profiles of lacunar and non-lacunar stroke," *Ann Neurol.*, 70(3):477-485.
Jickling et al. (2012) "Prediction of cardioembolic, arterial and lacunar causes of cryptogenic stroke by gene expression and infarct location," *Stroke*, 43(8): 2036-2041 [doi:10.1161/STROKEAHA.111.648725 pp. 1-12].
Karl-Olof Lövblad et al. (2006) "Actual diagnostic approach to the acute stroke patient," *Neuro Eur Radiol*, 16:1253-1269.
Laskowitz et al. (2005) "Panel of Biomarkers Predicts Stroke," *Ann. N.Y. Acad. Sci.*, 1053:30.
Leypoldt et al. (2009) "Dimethylarginine Dimethylaminohydrolase-1 Transgenic Mice are not Protected from Ischemic Stroke," *PlosOne*, 4(10):e7337(1-4).
Li et al. (Oct. 2013) "Transcriptome Analysis Reveals Distinct Patterns of Long Noncoding RNAs in Heart and Plasma of Mice with Heart Failure," *Plos ONE*, 8(10):e77938, 10 pp.
Lim et al. (2010) "MicroRNA in Cerebral Ischemia," *Translational Stroke Research*, 1:287-303.
Lynch et al. (2004) "Novel diagnostic test for acute stroke," *Stroke*, 35(1):57-63.
May et al. (1988) "How many species are there on Earth," *Science*, 241:1441-1449.
Montaner et al. (2008) "Etiologic diagnosis of ischemic stroke subtypes with plasma biomarkers," *Stroke*, 39(8):2280-2287.

(56) References Cited

OTHER PUBLICATIONS

Moore et al. (2005) "Using peripheral blood mononuclear cells to determine a gene expression profile of acute ischemic stroke: a pilot investigation," *Circulation*, 111(2):212-21.
Patel et al. (Dec. 12, 2001) "Lack of Clinical Significance of Early Ischemic Changes on Computed Tomography in Acute Stroke," *Jama*, 286(22):2830-2838.
Pradervand et al. (2008) "Affymetrix Whole-Transcript Human Gene 1.0 ST array is highly concordant with standard 3'expression arrays," *BioTechniques*, 44(6):759-762.
Read et al. (2001) "Stroke Genomics: Approaches to Identify, Validate, and Understand Ischemic Stroke Gene Expression," *J. Cereb. Blood Flow Metab.*, 21:755-778.
Reynolds et al. (2003) "Early Biomarkers of Stroke," *Clin. Chem.*, 49:1733-1739.
Rothwell et al. (2007) "Effect of urgent treatment of transient ischaemic attack and minor stroke on early recurrent stroke (EXPRESS study): a prospective population-based sequential comparison," *Lancet*, 370:1432-42.
Sendera et al. (2002) "Expression Profiling with Oligonucleotide Arrays: Technologies and Applications for Neurobiology," *Neurochemical Research*, 27:1005-1026.
Sharp et al. (2007) "Genomic Profiles of Stroke in Blood," *Stroke*, 28:691-693.
Slogoff et al. (1985) "Does Perioperative Myocardial Ischemia Lead to Postoperative Myocardial Infarction?" *Anesthesiology*, 62:107-114.
Stamova et al. (2009) "Identification and validation of suitable endogenous reference genes for gene expression studies in human peripheral blood," *BMC Medical Genomics* 2:49 pages, 1-13.
Stamova et al. (2010) "Gene Expression Profiling of Blood for the Prediction of Ischemic Stroke," Supplementary Material, *Stroke*, 41(10):2171-2177, 26 pages.
Stapleton et al. (Mar. 1999) "Prospective Comparison of Whole-Blood- and Plasma-Based Hepatitis C Virus RNA Detection Systems: Improved Detection Using Whole Blood as the Source of Viral RNA," *Journal of Clinical Microbiology*, 37(3):484-489.
Swarup et al. (2007) "Circulating (cell-free) nucleic acids—A promising, non-invasive tool for early detection of several human diseases," *FEBS Letters*, 581:795-799.
Tang et al. (2005) "Blood Gene Expression Profiling of Neurologic Diseases: A Pilot Microarray Study," *Arch Neurol.*, 62:210-215.
Tang et al. (2006) "Gene expression in blood changes rapidly in neutrophils and monocytes after ischemic stroke in humans: a microarray study," *Journal of Cerebral Blood Flow and Metabolism*, 26(8):1089-1102.
Thellin et al. (1999) "Housekeeping genes as internal standards: use and limits," *J. Biotechnol.*, 75:291-295.
Tombul et al. (2005) "Hemostatic markers and platelet aggregation factors as predictive markers for type of stroke and neurological disability following cerebral infarction," *Journal of Clinical Neuroscience*, 12(4): 429-434.
Veltkamp et al. (2002) "Transient focal ischemia increases endothelial nitric oxide synthase in cerebral blood vessels," *Stroke*, 33(11):2704-2710.
Viswanathan et al. (2006) "Cerebral Microhemorrhage," *Stroke, Journal of the American Heart Association*, 37:550-555.
Whiteley et al. (2008) "Blood Biomarkers in the Diagnosis of Ischemic Stroke: A Systematic Review," *Stroke*, 39(10):2902-2909.
Whiteley et al. (2009) "Blood Markers for the Prognosis of Ischemic Stroke: A Systematic Review," *Stroke*, 40:e380-e389, 27pp.
Xu et al. (2008) "Gene expression in peripheral blood differs after cardioembolic compared with large-vessel atherosclerotic stroke: biomarkers for the etiology of ischemic stroke," *J Cereb Blood Flow Metab.*, 28(7):1320-1328 [Epub Apr. 2, 2008].
Zhan et al. (2011) "Transient ischemic attacks characterized by RNA profiles in blood," *Neurology*, 77(19):1718-1724.
Zhan et al. (2010) "Brief focal cerebral ischemia that simulates transient ischemic attacks in humans regulates gene expression in rat peripheral blood" *J Cereb Blood Flow Metab.*, 30(1):110-118 DOI: 10.1038/jcbfm.2009.189.
Ziegler et al. (2007) "TLR2 has a Detrimental role in Mouse Transient Focal Cerebral Ischemia," *Biochemical and Biophysical Research Communication*, 359:574-579.
BETSI Project, Biotechnology Education & Training Sequence Investment, (2008) "Preparation of Human Chromosome Spreads," pp. 1-6; Southwestern College, 900 Otay Lakes Road, Chula Vista, 91910, www.swccd.edu/-betsi.
Shendure et al. (Oct. 2008) "Next-generation DNA sequencing," *Nature Biotechnology*, 26(10): 1135-1145.

\* cited by examiner

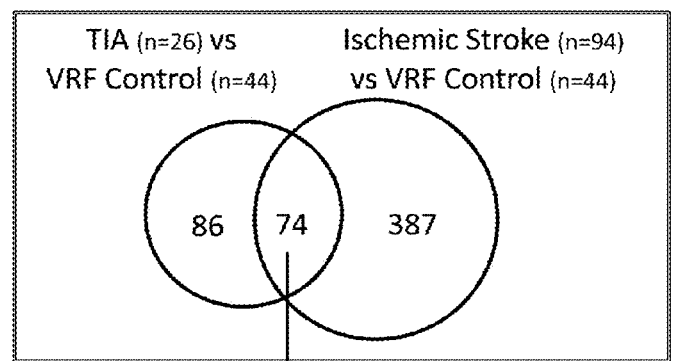
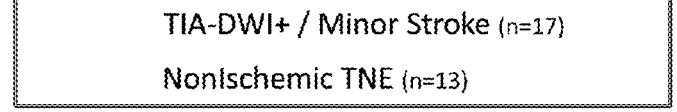
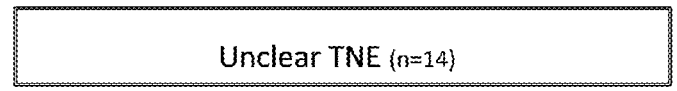
Fig. 1A. Derivation
Fig. 1B. Validation
Fig. 1C. Prediction
Fig. 1A-C

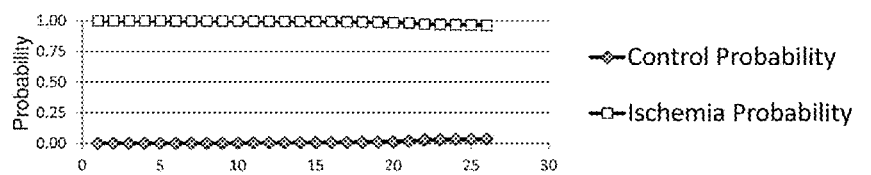
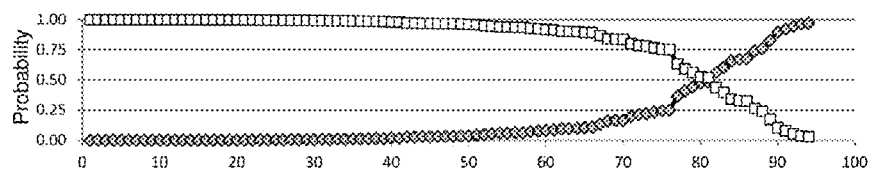
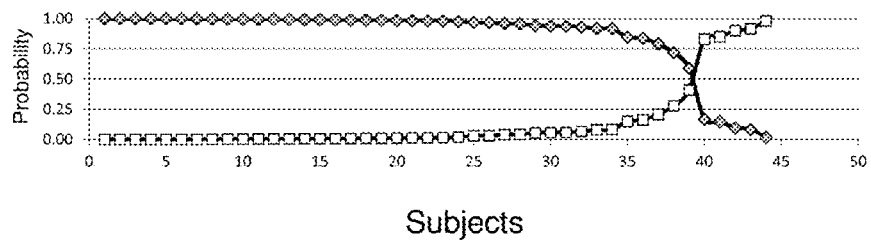
Fig. 3A-C

BIOMARKERS FOR DIAGNOSING ISCHEMIA

CROSS-REFERENCE TO RELATED APPLICATIONS

This application is a continuation of U.S. application Ser. No. 14/370,709, filed on Jul. 3, 2014, issued as U.S. Pat. No. 9,410,204 on Aug. 9, 2016, which is a U.S. national phase under 35 U.S.C. § 371 of International Application No. PCT/US2013/020240, filed on Jan. 4, 2013, which claims the benefit under 35 U.S.C. § 119(e) of U.S. Provisional Application No. 61/584,232, filed on Jan. 7, 2012, which are hereby incorporated herein by reference in their entireties for all purposes.

STATEMENT OF GOVERNMENTAL SUPPORT

This invention was made with government support under Grant No. NS056302 awarded by the National Institutes of Health. The government has certain rights in the invention.

FIELD OF THE INVENTION

The present invention provides methods and compositions for diagnosing and predicting the occurrence of ischemia. For example, the present invention provides methods and compositions for diagnosing and predicting the risk and cause of transient neurological events (TNE) as ischemic or non-ischemic.

BACKGROUND OF THE INVENTION

Systemic inflammation is linked to ischemic stroke and transient ischemic attack (TIA). Cerebral ischemia produces many endogenous ligands and cytokines that elicit an immune response (Arumugam, et al., *Shock*. (2009) 32:4-16). Leukocytes, including neutrophils and monocytes, are activated and recruited to initiate processes of containment, removal, and repair. We have previously demonstrated in a rat model of TIA that a peripheral immune response occurs to transient brain ischemia with similarities to that observed in experimental brain infarction (Zhan, et al., *J Cereb Blood Flow Metab*. (2010) 30:110-118; Zhan, et al., *Brain Res*. (2008) 1234:183-197). This suggests that aspects of the immune response to cerebral ischemia in TIA and stroke are common and may be useful in identifying ischemic events.

In clinical practice, deciphering whether a transient neurological event (TNE) is of ischemic or nonischemic etiology is often difficult. Many common neurological conditions mimic the symptoms of TIA, including migraine, seizure, and syncope. The transient nature of TIA adds to the diagnostic challenge as objective deficits generally resolve by the time of presentation and assessment of symptoms is reliant on patient recall and physician interpretation. Current diagnostic tests including neuroimaging, electrocardiogram, and electroencephalogram are frequently unremarkable, leaving the cause of a TNE unclear. As a result, TIA is estimated to be incorrectly diagnosed in as many as 50% of cases (Ferro, et al., *Stroke*. (1996) 27:2225-2229; Kraaijeveld, et al., *Stroke*. (1984) 15:723-725; Castle, et al., *Stroke*. (2010) 41:1367-1370; Bos, et al., *JAMA*. (2007) 298:2877-2885; and Johnston S C. *JAMA*. (2007) 298:2912-2913). However, correctly identifying ischemic TNE is critical as the risk for stroke is high in TIA and can be reduced by early initiation of stroke prevention therapy (Rothwell, et al., *Lancet*. (2007) 370:1432-1442). Additionally, identifying nonischemic TNE (which have a very low risk of stroke) will improve risk stratification and use of health care resources. Thus, improved methods to distinguish ischemic from nonischemic causes of TNE are needed.

Previous studies have demonstrated an immune response in patients with stroke by evaluating leukocyte RNA expression using whole genome microarrays (Barr, et al., *Neurology*. (2010) 75:1009-1014; Jickling, et al. *Ann Neurol*. (2010) 68:681-692; and Stamova, et al., *Stroke*. (2010) 41:2171-2177). However, the distinction between immune response to cerebral ischemia and cerebral infarction was unclear. We report herein the pathways associated with the peripheral immune response to cerebral ischemia, which has clinical utility to identify ischemic causes of TNE.

SUMMARY OF THE INVENTION

The present invention provides biomarkers useful for diagnosing the occurrence or risk of ischemia, particularly transient cerebral ischemia, and for differentiating a transient neurological event as ischemic or non-ischemic. Accordingly, in one aspect, the invention provides methods for diagnosing transient cerebral ischemia or a predisposition for experiencing transient cerebral ischemia. In some embodiments, the methods comprise: determining a level of expression of a plurality of ischemia-associated biomarkers in a biological sample from a patient, wherein an increase or decrease of the level of expression compared to a control is correlative with or indicates that the patient has suffered or is at risk of experiencing transient cerebral ischemia, wherein the plurality of ischemia-associated biomarkers is selected from the biomarkers set forth in Tables 3 and 5, thereby diagnosing transient cerebral ischemia or a predisposition for experiencing transient cerebral ischemia.

In another aspect, the invention provides methods for diagnosing and/or differentiating a transient neurological event (TNE) as ischemic or non-ischemic. In some embodiments, the methods comprise: determining a level of expression of a plurality of ischemia-associated biomarkers in a biological sample from a patient, wherein an increase or decrease of the level of expression compared to a control is correlative with or indicates that the patient has suffered or is at risk of experiencing transient cerebral ischemia, wherein the plurality of ischemia-associated biomarkers is selected from the biomarkers set forth in Tables 3 and 5, thereby diagnosing a transient neurological event (TNE) as ischemic or non-ischemic.

In a related aspect, the invention provides methods for identifying the occurrence or a predisposition for experiencing ischemia. In some embodiments, the methods comprise: determining a level of expression of a plurality of ischemia-associated biomarkers in a biological sample from a patient, wherein an increase or decrease of the level of expression compared to a control is correlative with or indicates that the patient has suffered or is at risk of experiencing ischemia, wherein the plurality of ischemia-associated biomarkers is selected from the biomarkers set forth in Tables 3 and 5, thereby identifying the occurrence or a predisposition for experiencing ischemia. In some embodiments, the ischemia is selected from the group consisting of cerebral ischemia, myocardial ischemia and pulmonary ischemia.

With respect to embodiments of the methods, in some embodiments, an increased expression level of one or more (e.g., 2, 3, 4, 5, 6, 7, 8, 9, 10, 11, 12, 13, 14, 15 or all) ischemia-associated biomarkers selected from the group consisting of UBE2J1, ELAVL3, FCGR2B, BLVRA, JMJD6, DDAH2, PTRH2, CARD16, CAV1, ZNF608, NDUFB3, SLC22A4, PCMT1, CACNA1A, CASP1 and LOC100129105 indicates that the patient has suffered or is at risk of experiencing ischemia. In some embodiments, an increased expression level of one or more (e.g., 2, 3, 4, 5, 6, 7, 8, 9, 10, 11, 12, 13, 14, 15, 20, 25, 30, 35, 40 or all) ischemia-associated biomarkers selected from the group consisting of AIM2, C14orf101, DNAH17, UBE2J1, LOC203274, PGS1, ZEB2, DDAH2, CARD16, SPATA4, ANXA3, WIT1, FCGR2B, CACNA1A, FKBP15, N4BP2L2, HNRNPH2, ELAVL3, ZNF608, TLR10, BLVRA, SLC22A4, RAB27A, LTBR, CARD16///CASP1, IGFBP5, CASP5, LTB, NDUFB3, SHOX2, CAV1, CNIH4, FLJ39051, CASP1, PTRH2, LOC100129105, PCMT1, CYTH4, JMJD6, DRAM1, FCGR1B indicates that the patient has suffered or is at risk of experiencing ischemia. In some embodiments, an increased expression level of one or more (e.g., 2, 3, 4, 5, 6, 7, 8, 9, 10, 11, 12, 13, 14, 15, 20, 25, 30 or all) ischemia-associated biomarkers selected from the group consisting of CARD16, IRF7, TLR6, NMU, C13orf16, TAPBP, BTC, ZBP1, HSPA6, TWIST1, PLSCR1, SAMD9L, OSTCL, C9orf66, GYPA, ADM, ANKRD22, SHOX, ZNF354A, SRGAP1, GRM5, BAGE, XRCC4, SLC37A3, OVOL2, LIFR, RASAL2, hCG_1749898, IQGAP3, HS3ST3A1, NPR3, SIX3 and HCN1 indicates that the patient has suffered or is at risk of experiencing ischemia. In some embodiments, an increased expression level of one or more (e.g., 2, 3, 4, 5, 6, 7, 8, 9, 10, 11, 12, 13, 14, 15, 20, 25, 30, 35, 40 or all) ischemia-associated biomarkers selected from the group consisting of UBE2J1, CARD16, LOC203274, ZNF608, CARD16///CASP1, PTRH2, ANXA3, FCGR2B, C14orf101, LOC100129105, DDAH2, RAB27A, AIM2, CASP5, HNRNPH2, RAB27A, SHOX2, CNIH4, TLR10, ZEB2, NDUFB3, CYTH4, BLVRA, FLJ39051, SLC22A4, DNAH17, SPATA4, CACNA1A, CASP1, PGS1, LTBR, FCGR1B, IGFBP5, LTB, N4BP2L2, DRAM1, WIT1, ELAVL3, FKBP15, JMJD6, CAV1 and PCMT1 indicates that the patient has suffered or is at risk of experiencing ischemia.

Conversely, in some embodiments, a decreased expression level of one or more (e.g., 2, 3, 4, 5, 6, 7, 8, 9, 10, 11, 12, 13, 14, 15 or all) ischemia-associated biomarkers selected from the group consisting of UBE2J1, ELAVL3, FCGR2B, BLVRA, JMJD6, DDAH2, PTRH2, CARD16, CAV1, ZNF608, NDUFB3, SLC22A4, PCMT1, CACNA1A, CASP1 and LOC100129105 indicates that the patient has not suffered or is not at risk of experiencing ischemia. In some embodiments, a decreased expression level of one or more (e.g., 2, 3, 4, 5, 6, 7, 8, 9, 10, 11, 12, 13, 14, 15, 20, 25, 30, 35, 40 or all) ischemia-associated biomarkers selected from the group consisting of AIM2, C14orf101, DNAH17, UBE2J1, LOC203274, PGS1, ZEB2, DDAH2, CARD16, SPATA4, ANXA3, WIT1, FCGR2B, CACNA1A, FKBP15, N4BP2L2, HNRNPH2, ELAVL3, ZNF608, TLR10, BLVRA, SLC22A4, RAB27A, LTBR, CARD16///CASP1, IGFBP5, CASP5, LTB, NDUFB3, SHOX2, CAV1, CNIH4, FLJ39051, CASP1, PTRH2, LOC100129105, PCMT1, CYTH4, JMJD6, DRAM1, FCGR1B indicates that the patient has not suffered or is not at risk of experiencing ischemia. In some embodiments, a decreased expression level of one or more (e.g., 2, 3, 4, 5, 6, 7, 8, 9, 10, 11, 12, 13, 14, 15, 20, 25, 30 or all) ischemia-associated biomarkers selected from the group consisting of CARD16, IRF7, TLR6, NMU, C13orf16, TAPBP, BTC, ZBP1, HSPA6, TWIST1, PLSCR1, SAMD9L, OSTCL, C9orf66, GYPA, ADM, ANKRD22, SHOX, ZNF354A, SRGAP1, GRM5, BAGE, XRCC4, SLC37A3, OVOL2, LIFR, RASAL2, hCG_1749898, IQGAP3, HS3ST3A1, NPR3, SIX3 and HCN1 indicates that the patient has not suffered or is not at risk of experiencing ischemia. In some embodiments, a decreased expression level of one or more (e.g., 2, 3, 4, 5, 6, 7, 8, 9, 10, 11, 12, 13, 14, 15, 20, 25, 30, 35, 40 or all) ischemia-associated biomarkers selected from the group consisting of UBE2J1, CARD16, LOC203274, ZNF608, CARD16///CASP1, UBE2J1, PTRH2, ANXA3, FCGR2B, C14orf101, LOC100129105, DDAH2, RAB27A, AIM2, CASP5, HNRNPH2, RAB27A, SHOX2, CNIH4, TLR10, ZEB2, NDUFB3, CYTH4, BLVRA, FLJ39051, SLC22A4, DNAH17, SPATA4, CACNA1A, CASP1, PGS1, LTBR, FCGR1B, IGFBP5, LTB, N4BP2L2, DRAM1, WIT1, ELAVL3, FKBP15, JMJD6, CAV1 and PCMT1 indicates that the patient has not suffered or is not at risk of experiencing ischemia.

In some embodiments, a decreased expression level of one or more (e.g., 2, 3, 4, 5, 6, 7 or all) ischemia-associated biomarkers selected from the group consisting of AK5, DIP2A, ETS1, CCND3, GNE, BCL9L, SPATA5, and LBH indicates that the patient has suffered or is at risk of experiencing ischemia. In some embodiments, a decreased expression level of one or more (e.g., 2, 3, 4, 5, 6, 7, 8, 9, 10, 11, 12, 13, 14, 15, 20 or all) ischemia-associated biomarkers selected from the group consisting of NEIL2, FOXK1, NUCKS1, MMP19, APBA2, SPATA5, BCL9L, GLG1, CCND3, TBC1D10A, AK5, ZNF609, ETS1, WHAMML1///WHAMML2, GNE, NPTXR, DIP2A, LBH, APBB1, ZMYND11, CAPN5, TAF3 and FMNL3 indicates that the patient has suffered or is at risk of experiencing ischemia. In some embodiments, a decreased expression level of one or more (e.g., 2, 3, 4, 5, 6, 7, 8, 9, 10, 11, 12, 13, 14, 15, 20, 25, 30, 35, 40, 45, 50 or all) ischemia-associated biomarkers selected from the group consisting of CAND1, GUSBL2, SLC3A1, ALDH6A1, CLTC, FUS, RANBP10, KIAA0391, MED1, NAPEPLD, KIAA1919, HCFC1, TPP2, G3BP1, PRDX6, YARS, PYGB, YBX1///YBX1P2, FUS///NR1H3, GCAT, CAPN5, LOC100129656, SMARCC2, HELLS, MAP2K7, ZNF652, GSTM1, C16orf35, KIAA1659, GSTM2, LOC440104, VTI1A, HERC1, ALS2CL, GSTM1, GCAT, ERMN, LOC100293532, IFT80, RBM6, BAZ1B, HNRNPUL2, ENTPD5, ATXN2L, LPIN1, METTL3, MBNL2, SMURF2, C20orf196, UNC84A, DCAF16 and EIF3B indicates that the patient has suffered or is at risk of experiencing ischemia. In some embodiments, a decreased expression level of one or more (e.g., 2, 3, 4, 5, 6, 7, 8, 9, 10, 11, 12, 13, 14, 15, 20, 25 or all) ischemia-associated biomarkers selected from the group consisting of FOXK1, AK5, APBA2, NUCKS1, NEIL2, WHAMML1///WHAMML2, GLG1, CCND3, LBH, TAF3, TBC1D10A, FMNL3, SPATA5, ZMYND11, CAPN5, GNE, MMP19, ZNF609, ETS1, BCL9L, DIP2A, APBB1, NPTXR indicates that the patient has suffered or is at risk of experiencing ischemia.

Conversely, in some embodiments, an increased expression level of one or more (e.g., 2, 3, 4, 5, 6, 7 or all) ischemia-associated biomarkers selected from the group consisting of AK5, DIP2A, ETS1, CCND3, GNE, BCL9L, SPATA5, and LBH indicates that the patient has not suffered or is not at risk of experiencing ischemia. In some embodiments, an increased expression level of one or more (e.g., 2, 3, 4, 5, 6, 7, 8, 9, 10, 11, 12, 13, 14, 15, 20 or all) ischemia-associated biomarkers selected from the group consisting of NEIL2, FOXK1, NUCKS1, MMP19, APBA2, SPATA5, BCL9L, GLG1, CCND3, TBC1D10A, AK5, ZNF609, ETS1, WHAMML1///WHAMML2, GNE, NPTXR, DIP2A, LBH, APBB1, ZMYND11, CAPN5, TAF3 and FMNL3 indicates that the patient has not suffered or is not at risk of experiencing ischemia. In some embodiments, an increased expression level of one or more (e.g., 2, 3, 4, 5, 6, 7, 8, 9, 10, 11, 12, 13, 14, 15, 20, 25, 30, 35, 40, 45, 50 or all) ischemia-associated biomarkers selected from the group consisting of CAND1, GUSBL2, SLC3A1, ALDH6A1, CLTC, FUS, RANBP10, KIAA0391, MED1, NAPEPLD, KIAA1919, HCFC1, TPP2, G3BP1, PRDX6, YARS, PYGB, YBX1///YBX1P2, FUS///NR1H3, GCAT, CAPN5, LOC100129656, SMARCC2, HELLS, MAP2K7, ZNF652, GSTM1, C16orf35, KIAA1659, GSTM2, LOC440104, VTI1A, HERC1, ALS2CL, GSTM1, GCAT, ERMN, LOC100293532, IFT80, RBM6, BAZ1B, HNRN-PUL2, ENTPD5, ATXN2L, LPIN1, METTL3, MBNL2, SMURF2, C20orf196, UNC84A, DCAF16 and EIF3B indicates that the patient has not suffered or is not at risk of experiencing ischemia. In some embodiments, an increased expression level of one or more (e.g., 2, 3, 4, 5, 6, 7, 8, 9, 10, 11, 12, 13, 14, 15, 20, 25 or all) ischemia-associated biomarkers selected from the group consisting of FOXK1, AK5, APBA2, NUCKS1, NEIL2, WHAMML1///WHAMML2, GLG1, CCND3, LBH, TAF3, TBC1D10A, FMNL3, SPATA5, ZMYND11, CAPN5, GNE, MMP19, ZNF609, ETS1, BCL9L, DIP2A, APBB1, NPTXR indicates that the patient has not suffered or is not at risk of experiencing ischemia.

In a related aspect, the invention provides methods for diagnosing and/or differentiating a transient neurological event (TNE) as ischemic or non-ischemic. In some embodiments, the methods comprise: determining a level of expression of a plurality of ischemia-associated biomarkers in a biological sample from a patient, wherein an increase or decrease of the level compared to a control level of expression indicates that the patient has experienced or is at risk of experiencing transient cerebral ischemia;

wherein an increase of the expression level of one or more biomarkers selected from the group consisting of UBE2J1, ELAVL3, FCGR2B, BLVRA, JMJD6, DDAH2, PTRH2, CARD16, CAV1, ZNF608, NDUFB3, SLC22A4, PCMT1, CACNA1A, CASP1 and LOC100129105, and/or a decrease of the expression level of one or more biomarkers selected from the group consisting of AK5, DIP2A, ETS1, CCND3, GNE, BCL9L, SPATA5, and LBH, compared to the control level of expression is correlative with or indicates that the patient has experienced or is at risk of experiencing transient cerebral ischemia, thereby diagnosing a transient neurological event (TNE) as ischemic or non-ischemic. In some embodiments, a decrease of the expression level of one or more biomarkers selected from the group consisting of UBE2J1, ELAVL3, FCGR2B, BLVRA, JMJD6, DDAH2, PTRH2, CARD16, CAV1, ZNF608, NDUFB3, SLC22A4, PCMT1, CACNA1A, CASP1 and LOC100129105, and/or an increase of the expression level of one or more biomarkers selected from the group consisting of AK5, DIP2A, ETS1, CCND3, GNE, BCL9L, SPATA5, and LBH, compared to the control level of expression is correlative with or indicates that the patient has not experienced or is not at risk of experiencing transient cerebral ischemia.

In some embodiments, the determining step is performed at 3 or fewer hours after a suspected ischemic event. In some embodiments, the determining step is performed at 3 or more hours after a suspected ischemic event. In some embodiments, the determining step is performed at least 24 hours after a suspected ischemic event. In some embodiments, the determining step is performed within 72 hours, for example, within 60 hours, 48 hours, 36 hours, 24 hours, 12 hours, 6 hours or 3 hours, after a suspected ischemic event.

In various embodiments, the expression levels of the biomarkers are concurrently or sequentially determined.

In some embodiments, the methods further comprise the step of obtaining a biological sample from the patient. In some embodiments, the biological sample is blood, serum or plasma.

In some embodiments, the method is performed in a clinical laboratory. In some embodiments, the method is performed at the point of care.

In some embodiments, the control is the expression level of one or more stably expressed endogenous reference biomarkers. In some embodiments, the plurality of stably expressed endogenous reference biomarkers are selected from USP7, MAPRE2, CSNK1G2, SAFB2, PRKAR2A, PI4 KB, CRTC1, HADHA, MAP1LC3B, KAT5, GTSE1, CDC2L1///CDC2L2, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445///LOC115110 and PEX16. In some embodiments, the ischemia-associated biomarkers are overexpressed or underexpressed at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, or more, in comparison to the expression levels of a plurality of stably expressed endogenous reference biomarkers. In some embodiments, the expression levels of 2, 3, 4, 5, 6, 7, 8, 9, 10, 15, 20, 25, 30, 35, or all, the endogenous reference biomarkers selected from the group consisting of USP7, MAPRE2, CSNK1G2, SAFB2, PRKAR2A, PI4 KB, CRTC1, HADHA, MAP1LC3B, KAT5, CDC2L1///CDC2L2, GTSE1, CDC2L1///CDC2L2, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445///LOC115110, PEX16 are determined as a control.

In some embodiments, the control is the expression level of the same biomarker in an individual with no history of stroke, heart attack, or peripheral vascular disease. In some embodiments, the control is a threshold level of expression representative of a population of individuals with no history of stroke, heart attack, peripheral vascular disease. The individual or population of individuals may or may not have at least one vascular risk factor (e.g., hypertension, diabetes mellitus, hyperlipidemia, or tobacco smoking).

In some embodiments, the level of expression of at least 15 biomarkers is determined. In some embodiments, the level of expression of about 15-85, 20-70, 30-60 or 40-50 ischemia-associated biomarkers are determined. In some embodiments, about 15, 20, 25, 30, 35, 40, 45, 50, 55, 60, 65, 70, 75, 80, 85, 90, 95 or 100 ischemia-associated biomarkers are determined. In some embodiments, the expression levels of at least about 3, 5, 10, 15, 20, 25, 30, 35, 40, 45, 50, or more, ischemia-associated biomarkers from Table 3 are determined. In some embodiments, the expression levels of at least about 3, 5, 10, 15, 20, 25, 30, 35, 40, 45, 50, or more, ischemia-associated biomarkers from Table 5 are determined.

In some embodiments, the patient is asymptomatic. In some embodiments, the patient is exhibiting symptoms of having experienced an ischemic event, of experiencing an ischemic event, or of an imminent ischemic event (e.g., cerebral ischemia, myocardial ischemia, pulmonary ischemia). In some embodiments, the patient has experienced or is suspected of having experienced an ischemic event. In some embodiments, the determining step is performed at 3 or fewer hours after the ischemic event. In some embodiments, the determining step is performed 3 or more hours after the ischemic event.

In some embodiments, the patient has at least one vascular risk factor. In some embodiments, the patient has no history of stroke, heart attack, peripheral vascular disease.

In some embodiments, the methods further comprise the step of providing a diagnosis to the patient based on the determination and identification of the level of expression of the set of ischemia-associated genes. As appropriate, the diagnosis may be for the occurrence or risk of transient cerebral ischemia or a non-ischemic transient neurological event. As appropriate, the diagnosis may be for the occurrence or risk of an ischemic event (e.g., cerebral ischemia, pulmonary ischemia, or myocardial ischemia).

In some embodiments, the methods further comprise the step of providing an appropriate treatment or prevention regime for ischemia to the patient. In some embodiments, wherein if the patient has experienced or has a predisposition to experience an ischemic event, further comprising the step of determining the cause or risk of the ischemic event. In some embodiments, the methods further comprise the step of recommending or providing a regime of treatment or prevention to the patient appropriate to the determined cause of ischemia. For example, in patients diagnosed as experiencing or having a predisposition for experiencing ischemia, the methods further provide for recommending or providing a regime of treatment or prevention for ischemia (e.g., cerebral ischemia, myocardial ischemia, pulmonary ischemia). The methods may further comprise the step of recommending or providing a regime of treatment to the patient appropriate for cerebral ischemia or transient cerebral ischemia. The methods may further comprise the step of recommending or providing a regime of treatment to the patient appropriate for myocardial ischemia. The methods may further comprise the step of recommending or providing a regime of treatment to the patient appropriate for pulmonary ischemia.

In various embodiments, the methods may further comprise the step of determining the cause or risk of ischemic stroke if the patient has experienced or has a predisposition to experience cerebral ischemia or transient cerebral ischemia. The methods may further comprise the step of recommending or providing a regime of treatment to the patient appropriate to the determined cause of cerebral ischemia. For example, in patients diagnosed as experiencing or having a predisposition for experiencing cardioembolic stroke, the methods further provide for recommending or providing a regime of treatment or prevention for cardioembolic stroke. In patients diagnosed as experiencing or having a predisposition for experiencing carotid stenosis, the methods further provide for recommending or providing a regime of treatment or prevention for carotid stenosis. In patients diagnosed as experiencing or having a predisposition for experiencing atrial fibrillation, the methods further provide for recommending or providing a regime of treatment or prevention for atrial fibrillation. In patients diagnosed as experiencing or having a predisposition for experiencing transient ischemic attack, the methods further provide for recommending or providing a regime of treatment or prevention for transient ischemic attack.

In patients diagnosed as experiencing or having a predisposition for experiencing a non-ischemic transient neurological event, the methods further provide for recommending or providing a regime of treatment or prevention for the non-ischemic transient neurological event (e.g., for migraine, for seizures, etc.).

With respect to embodiments for determination of the level of expression of the biomarkers, in some embodiments, the level of expression of the biomarker is determined at the transcriptional level. For example, in some embodiments, the level of expression is determined by detecting hybridization of an ischemic stroke-associated gene probe to gene transcripts of the biomarkers in the biological sample. In some embodiments, the hybridization step is performed on a nucleic acid array chip. In some embodiments, the hybridization step is performed in a microfluidics assay plate. In some embodiments, the level of expression is determined by amplification of gene transcripts of the biomarkers. In some embodiments, the amplification reaction is a polymerase chain reaction (PCR).

In some embodiments, the level of expression of the biomarker is determined at the protein level.

In another aspect, the invention provides a solid support comprising a plurality of nucleic acids that hybridize to a plurality of the genes set forth in Table 3 and/or a plurality of nucleic acids that hybridize to a plurality of the genes set forth in Table 5. In some embodiments, the solid support comprises a plurality of (e.g., 2, 3, 4, 5, 6, 7, 8, 9, 10, 11, 12, 13, 14, 15, 20, 25, 30 or all) nucleic acids that hybridize to a plurality of the genes selected from the group consisting of UBE2J1, ELAVL3, FCGR2B, BLVRA, AK5, JMJD6, DIP2A, ETS1, DDAH2, CCND3, GNE, PTRH2, CARD16, BCL9L, CAV1, ZNF608, NDUFB3, SLC22A4, PCMT1, CACNA1A, SPATA5, CASP1, LBH and LOC100129105. In some embodiments, the solid support comprises a plurality of (e.g., 2, 3, 4, 5, 6, 7, 8, 9, 10, 11, 12, 13, 14, 15, 20 or all) nucleic acids that hybridize to a plurality of the genes selected from the group consisting of UBE2J1, DDAH2, CARD16, BLVRA, BCL9L, ELAVL3, LOC100129105, SLC22A4, GNE, PCMT1, FCGR2B, DIP2A, CAV1, SPATA5, ZNF608, CACNA1A, NDUFB3, CASP1, JMJD6, AK5, LBH, PTRH2, ETS1, CCND3, AIM2, NEIL2, PGS1, C14orf101, DNAH17, ZEB2, WIT1, MMP19, FOXK1, LOC203274, APBA2, ANXA3, FKBP15, SPATA4, LTBR, N4BP2L2, RAB27A, NUCKS1, TBC1D10A, CARD16/// CASP1, IGFBP5, RAB27A, CNIH4, NPTXR, CASP5, TLR10, GLG1, SHOX2, HNRNPH2, APBB1, ZMYND11, FLJ39051, ZNF609, TAF3, DRAM1, LTB, CAPN5, WHAMML1///WHAMML2, FCGR1B, CYTH4 and FMNL3. In some embodiments, the solid support comprises a plurality of (e.g., 2, 3, 4, 5, 6, 7, 8, 9, 10, 11, 12, 13, 14, 15, 20, 25, 30 or all) nucleic acids that hybridize to a plurality of the genes selected from the group consisting of ADM, ALDH6A1, ALS2CL, ANKRD22, ATXN2L, BAGE, BAZ1B, BTC, C13orf16, C16orf35, C20orf196, C9orf66, CAND1, CAPN5, CARD16, CLTC, DCAF16, EIF3B, ENTPD5, ERMN, FUS, FUS///NR1H3, G3BP1, GCAT, GRM5, GSTM1, GSTM2, GUSBL2, GYPA, HCFC1, hCG_1749898, HCN1, HELLS, HERC1, HNRNPUL2, HS3ST3A1, HSPA6, IFT80, IQGAP3, IRF7, KIAA0391, KIAA1659, KIAA1919, LIFR, LOC100129656, LOC100293532, LOC440104, LPIN1, MAP2K7, MBNL2, MED1, METTL3, NAPEPLD, NMU, NPR3, OSTCL, OVOL2, PLSCR1, PRDX6, PYGB, RANBP10, RASAL2, RBM6, SAMD9L, SHOX, SIX3, SLC37A3, SLC3A1, SMARCC2, SMURF2, SRGAP1, TAPBP, TLR6, TPP2, TWIST1, UNC84A, VTI1A, XRCC4, YARS, YBX1///YBX1P2, ZBP1, ZNF354A and ZNF652.

In various embodiments, the solid support further comprises a plurality of (e.g., 2, 3, 4, 5, 6, 7, 8, 9, 10, 11, 12, 13, 14, 15, 20 or all) of nucleic acids that hybridize to a plurality of endogenous reference genes selected from the group consisting of USP7, MAPRE2, CSNK1G2, SAFB2, PRKAR2A, PI4 KB, CRTC1, HADHA, MAP1LC3B, KAT5, CDC2L1///CDC2L2, GTSE1, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445///LOC115110, PEX16.

In various embodiments, the solid support further comprises a plurality of (e.g., 2, 3, 4, 5, 6, 7, 8, 9, 10, 11, 12, 13, 14, 15, 20, 25, 30 or all) nucleic acids that hybridize to a plurality of ischemic stroke-associated biomarkers selected from the group consisting of FAT3, GADL1, CXADR, RNF141, CLEC4E, TIMP2, ANKRD28, TIMM8A, PTPRD, CCRL1, FCRL4, DLX6, GABRB2, GYPA, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA, MCTP1, SH3GL3, PGM5, CCDC144C///LOC100134159, LECT2, SHOX, TBX5, SPTLC3, SNIP, RBMS3, P704P, THSD4, SNRPN, GLYATL1, DKRZP434L187, OVOL2, SPIB, BXDC5, UNC5B, ASTN2, FLJ35934, CCDC144A, ALDOAP2, LDB3, LOC729222///PPFIBP1, HNRNPUL2, ELAVL2, PRTG, FOXA2, SCD5, LOC283027, LOC344595, RPL22, LOC100129488 and RPL22.

In various embodiments, the solid support further comprises a plurality of (e.g., 2, 3, 4, 5, 6, 7, 8, 9, 10, 11, 12, 13, 14, 15, 20 or all) nucleic acids that hybridize to a plurality of cardioembolic stroke-associated biomarkers selected from the group consisting of IRF6, ZNF254, GRM5, EXT2, AP3S2, PIK3C2B, ARHGEF5, COL13A1, PTPN20A///PTPN20B, LHFP, BANK1, HLA-DOA, EBF1, TMEM19, LHFP, FCRL1, OOEP, LRRC37A3, LOC284751, CD46, ENPP2, C19orf28, TSKS, CHURC1, ADAMTSL4, FLJ40125, CLEC18A, ARHGEF12, C16orf68, TFDP1 and GSTK1.

In various embodiments, the solid support further comprises a plurality of (e.g., 2, 3, 4, 5, 6, 7, 8, 9, 10, 11, 12, 13, 14, 15, 20 or all) nucleic acids that hybridize to a plurality of carotid stenosis-associated biomarkers selected from the group consisting of NT5E, CLASP2, GRM5, PROCR, ARHGEF5, AKR1C3, COL13A1, LHFP, RNF7, CYTH3, EBF1, RANBP10, PRSS35, C12orf42, LOC100127980, FLJ31945, LOC284751, LOC100271832, MTBP, ICAM4, SHOX2, DOPEY2, CMBL, LOC146880, SLC20A1, SLC6A19, ARHGEF12, C16orf68, GIPC2 and LOC100144603.

In various embodiments, the solid support further comprises a plurality of (e.g., 2, 3, 4, 5, 6, 7, 8, 9, 10, 11, 12, 13, 14, 15 or all) nucleic acids that hybridize to a plurality of atrial fibrillation-associated biomarkers selected from the group consisting of SMC1A, SNORA68, GRLF1, SDC4, HIPK2, LOC100129034, CMTM1, TTC7A, LRRC43, MIF///SLC2A11, PER3, PPIE, COL13A1, DUSP16, LOC100129034, BRUNOL6, GPR176, C6orf164 and MAP3K7IP1.

In various embodiments, the solid support further comprises a plurality of (e.g., 2, 3, 4, 5, 6, 7, 8, 9, 10, 11, 12, 13, 14, 15, 20 or all) nucleic acids that hybridize to a plurality of lacunar stroke-associated biomarkers selected from the group consisting of HLA-DQA1, FLJ13773, RASEF, CALM1, QKI, TTC12, CCL3///CCL3L1///CCL3L3, CCDC78, PRSS23, LAIR2, C18orf49, MPZL3, UTS2, FAM70B, UTS2, LOC254128, LGR6, IL8, CHML, STX7, PROCR, VAPA, LAG3, OASL, LOC100132181, HLA-DRB4, CCL2, UGCG, PDXDC1, ALS2CR11, SCAND2, GBP4, RUNX3, LRRC8B, TSEN54, UBA7, STK4, FAM179A, TGFBR3, CCDC114, GTF2H2, AKAP9, BNC2, BZRAP1, CCL4, CHST2, CSF1, ERBB2, GBR56, GRAMD3, GRHL2, GRK4, ITIH4, KIAA1618, LOC147646, LOC150622, LOC161527, PLEKHF1, PRKD2, RGNEF, SESN2, SLAMF7, SPON2, STAT1, SYNGR1, TRX21, TMEM67, TUBE1, ZNF827, AGFG1, BTG1, CFDP1, CNPY2, FAM105A, GATM, GTF2H2, IGHG1, IL18RAP, N4BP2, PHACTR1, QK1, RTKN2, SLC16A1, SOCS1, SPAG17, ST6GALNAC1, STK17B, STT3B, STX16, TBC1D12, TRIM4, UACA, and WHAMML2.

In some embodiments, the solid support is a microarray. In various embodiments, the microarray has 1000 or fewer hybridizing nucleic acids, for example, 900, 800, 700, 600, 500 or fewer hybridizing nucleic acids. In various embodiments, the microarray does not comprise nucleic acids that hybridize to genes whose expression is not correlative of or associated with ischemia.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization described below are those well-known and commonly employed in the art. Standard techniques are used for nucleic acid and peptide synthesis. Generally, enzymatic reactions and purification steps are performed according to the manufacturer's specifications. The techniques and procedures are generally performed according to conventional methods in the art and various general references (see generally, Sambrook et al. MOLECULAR CLONING: A LABORATORY MANUAL, 3rd ed. (2001) Cold Spring Harbor Laboratory Press, Cold Spring Harbor, N.Y. and Ausubel, et al., CURRENT PROTOCOLS IN MOLECULAR BIOLOGY, 1990-2008, Wiley Interscience), which are provided throughout this document. The nomenclature used herein and the laboratory procedures in analytical chemistry, and organic synthetic described below are those well-known and commonly employed in the art. Standard techniques, or modifications thereof, are used for chemical syntheses and chemical analyses.

"Ischemia" or "ischemic event" as used herein refers to diseases and disorders characterized by inadequate blood supply (i.e., circulation) to a local area due to blockage of the blood vessels to the area. Ischemia includes for example, strokes and transient ischemic attacks. Strokes include, e.g., ischemic stroke (including, but not limited to, cardioembolic strokes, atheroembolic or atherothrombotic strokes, i.e., strokes caused by atherosclerosis in the carotid, aorta, heart, and brain, small vessel strokes (i.e., lacunar strokes), strokes caused by diseases of the vessel wall, i.e., vasculitis, strokes caused by infection, strokes caused by hematological disorders, strokes caused by migraines, and strokes caused by medications such as hormone therapy), hemorrhagic ischemic stroke, intracerebral hemorrhage, and subarachnoid hemorrhage.

The term "transient ischemic attack," "TIA," or "ministroke" interchangeably refer to a change in the blood supply to a particular area of the brain, resulting in brief neurologic dysfunction that persists, by definition, for less than 24 hours. By definition, a TIA resolves within 24 hours, but most TIA symptoms resolve within a few minutes. If symptoms persist longer, then it is categorized as a stroke. Symptoms include temporary loss of vision (typically amaurosis fugax); difficulty speaking (aphasia); weakness on one side of the body (hemiparesis); numbness or tingling (paresthesia), usually on one side of the body, and dizziness, lack of coordination or poor balance. The symptoms of a TIA usually last a few seconds to a few minutes and most symptoms disappear within 60 minutes.

Transient neurological attacks (TNA) or transient neurological events (TNE) interchangeably refer to events involving neurological symptoms typically lasting only a few minutes or hours and no more than 24 hours. TIAs are considered focal TNAs; other events—including quickly resolving amnesia, confusion, or dizziness and fainting are considered nonfocal TNAs.

The term "small deep infarct" or "small deep infarction" or "SDI" interchangeably refer to focal infarction of the brain due to an uncertain cause, including but not limited to, cardioembolic, atheroembolic, atherosclerotic disease of the parent artery or disease of the perforating artery.

The term "lacunar stroke" or "lacune" interchangeably refer to focal infarction of the brain due to perforating branch occlusion from microatheroma or lipohyalinosis. Implicit in this definition of lacunar stroke is that the: 1) infarction is not due to cardioembolic source; 2) infarction is not due to atherosclerotic disease of parent arteries; 3) infarction occurs in regions of the brain supplied by penetrating arteries, e.g., basal ganglia, thalamus, internal capsule, corona radiata or pons; 4) lacunar stroke is oftentimes associated with the presence of hypertension, diabetes or other vascular risk factors; and 5) infarcts tend to be smaller, generally less than 50 mm in diameter. When the cause of stroke is uncertain or likely other than perforating artery disease, then the more general term—small deep infarct—is appropriate. See, e.g., Caplan, *Stroke* (2003) 34(3):653-9; Norrving, *Pract Neurol* (2008) 8:222-228; Lastilla, *Clin Exp Hypertens*. (2006) 28(3-4):205-15; and Arboix and Marti-Vilalta, *Expert Rev Neurother*. (2009) 9(2):179-96.

An "ischemia reference expression profile" refers to the pattern of expression of a set of genes (e.g., a plurality of the genes set forth in Tables 3 and/or 5 differentially expressed (i.e., overexpressed or underexpressed) in an individual who has suffered or is at risk of experiencing ischemia (e.g., transient cerebral ischemia, transient ischemic attacks (TIA), cerebral ischemia, myocardial ischemia, pulmonary ischemia) relative to the expression in a control (e.g., the expression level in an individual free of an ischemic event or the expression level of a stably expressed endogenous reference biomarker). A gene from Tables 3 and/or 5 that is expressed at a level that is at least about 1.2-, 1.3-, 1.4-, 1.5-, 1.6-, 1.7-, 1.8-, 1.9-, 2.0-, 2.1-, 2.2-, 2.3-, 2.4-, 2.5-, 2.6-, 2.7-, 2.8-, 2.9-, 3.0-, 3.1-, 3.2-, 3.3-3.4- or 3.5-fold higher than the level in a control is a gene overexpressed in ischemia and a gene from Tables 3 and/or 5 that is expressed at a level that is at least about 1.2-, 1.3-, 1.4-, 1.5-, 1.6-, 1.7-, 1.8-, 1.9-, 2.0-, 2.1-, 2.2-, 2.3-, 2.4-, 2.5-, 2.6-, 2.7-, 2.8-, 2.9-, 3.0-, 3.1-, 3.2-3.3-, 3.4- or 3.5-fold lower than the level in a control is a gene underexpressed in ischemia. Alternately, genes that are expressed at a level that is at least about 10%, 20%, 30%, 40%, 50%, 60%, 70%, 80%, 90%, or 100% higher than the level in a control is a gene overexpressed in ischemia and a gene that is expressed at a level that is at least about 10%, 20%, 30%, 40%, 50%, 60%, 70%, 80%, 90%, or 100% lower than the level in a control is a gene underexpressed in ischemia.

A "plurality" refers to two or more, for example, 2, 3, 4, 5, 6, 7, 8, 9, 10, 11, 12, 13, 14, 15, 16, 17, 18, 19, 20, 21, 22, 23 or more (e.g., genes). In some embodiments, a plurality refers to concurrent determination of expression levels about 15-85, 20-60 or 40-50 genes, for example, about 15, 20, 25, 30, 35, 40, 45, 50, 55, 60, 65, 70, 75, 80, 85, 90, 95, 100, or more, genes. In some embodiments, "plurality" refers to all genes listed in one or more or all tables, e.g., all genes listed in Tables 1, 2, 5A, 5B, 5C, 5D, 7, 8 and/or 9.

The terms "patient," "subject" or "individual" interchangeably refers to a mammal, for example, a human or a non-human mammal, including primates (e.g., macaque, pan troglodyte, pongo), a domesticated mammal (e.g., felines, canines), an agricultural mammal (e.g., bovine, ovine, porcine, equine) and a laboratory mammal or rodent (e.g., rattus, murine, lagomorpha, hamster, guinea pig).

"Sample" or "biological sample" includes sections of tissues such as biopsy and autopsy samples, and frozen sections taken for histologic purposes. Such samples include blood, sputum, tissue, lysed cells, brain biopsy, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

"Array" as used herein refers to a solid support comprising attached nucleic acid or peptide probes. Arrays typically comprise a plurality of different nucleic acid or peptide probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., *Science*, 251:767-777 (1991). These arrays may generally be produced using mechanical synthesis methods or light directed synthesis methods which incorporate a combination of photolithographic methods and solid phase synthesis methods. Techniques for the synthesis of these arrays using mechanical synthesis methods are described in, e.g., U.S. Pat. No. 5,384,261. Arrays may comprise a planar surface or may be nucleic acids or peptides on beads, gels, polymeric surfaces, fibers such as fiber optics, glass or any other appropriate substrate as described in, e.g., U.S. Pat. Nos. 5,770,358, 5,789,162, 5,708,153, 6,040,193 and 5,800, 992. Arrays may be packaged in such a manner as to allow for diagnostics or other manipulation of an all-inclusive device, as described in, e.g., U.S. Pat. Nos. 5,856,174 and 5,922,591.

The term "gene" means the segment of DNA involved in producing a polypeptide chain; it includes regions preceding and following the coding region (leader and trailer) as well as intervening sequences (introns) between individual coding segments (exons).

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

The phrase "stringent hybridization conditions" refers to conditions under which a probe will hybridize to its target subsequence, typically in a complex mixture of nucleic acid, but to no other sequences. Stringent hybridization conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent hybridization conditions are selected to be about 5-10° C. lower than the thermal melting point for the specific sequence at a defined ionic strength Ph. The $T_m$ is the temperature (under defined ionic strength, Ph, and nucleic concentration) at which 50% of the probes complementary to the target hybridize to the target sequence at equilibrium (as the target sequences are present in excess, at $T_m$, 50% of the probes are occupied at equilibrium). Stringent hybridization conditions will be those in which the salt concentration is less than about 1.0 M sodium ion, typically about 0.01 to 1.0 M sodium ion concentration (or other salts) at Ph 7.0 to 8.3 and the temperature is at least about 30° C. for short probes (e.g., 10 to 50 nucleotides) and at least about 60° C. for long probes (e.g., greater than 50 nucleotides). Stringent hybridization conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent hybridization conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. "Amino acid analogs" refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region of a TIA-associated gene (e.g., a gene set forth in Tables 1, 2, 5A, 5B, 5C, 5D, 7, 8 and/or 9), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to TIA-associated nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

BRIEF DESCRIPTION OF THE DRAWINGS

FIGS. 1A-C illustrate a flow diagram of study analyses. A. To derive common ischemia genes, TIA and ischemic stroke subjects were compared to controls. Of the 160 probesets differentially expressed in TIA, 74 (46%) were identical to those in ischemic stroke (FDR<0.05, fold change ≥1.2|). A subset of 26 probesets were found to optimally distinguish TIA and ischemic stroke from controls using LDA. B. A prediction model using these 26 probesets was developed and evaluated by cross-validation on the original validation cohort, and on a validation cohort of TNE of known ischemic and nonischemic etiology. C. The 26 probesets were subsequently used to predict ischemia in TNE of unclear etiology.

FIGS. 3A-C illustrate probability plots of the predicted diagnosis of cerebral ischemia in TIA and ischemic stroke versus controls. The predicted probabilities are from cross-validation of the LDA 26 common ischemic gene model on the derivation cohort. The predicted probability of ischemia versus nonischemia in shown for (3A) the 26 patients clinically diagnosed as TIA; (3B) the 94 with ischemic strokes; (3C) the 44 vascular risk factor controls. The probability of a subject being ischemia is shown in red, and the probability of a subject being nonischemia is shown in blue. Cerebral ischemia was correctly predicted in 89% of subjects, and nonischemia was correctly predicted in 89% of controls. The probability of predicted diagnosis for the majority of subjects was >90%.

DETAILED DESCRIPTION

1. Introduction

Figure 2:
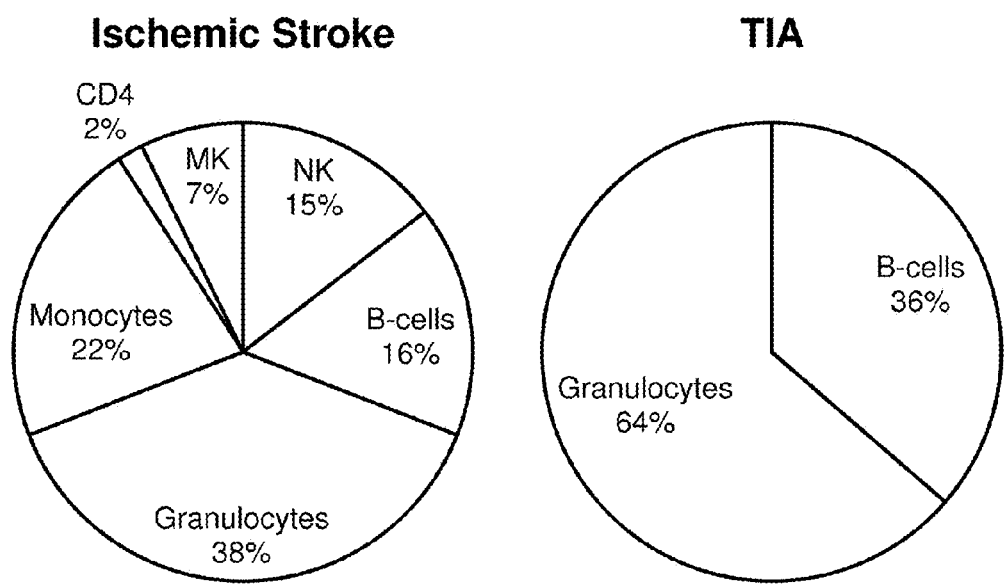
FIG. 2 illustrates proportional representation of the immune cells that contributed to RNA expression in blood in TIA and ischemic stroke patients. Previous studies have identified genes unique to each cell type in blood (Watkins, et al., Blood. (2009) 113:e1-9). These profiles were used to identify cells contributing to the differentially expressed genes in TIA and stroke. The genes differentially expressed in TIA were associated mostly with granulocytes and B-cells. The genes differentially expressed in ischemic stroke were associated mostly with granulocytes, monocytes, natural killer cells and B-cells, with some contribution from megakaryocytes and CD4 T-cells.

We have compared genes expressed in the blood of patients with transient ischemic attacks (TIA) and ischemic stroke to controls subjects to identify patients with cerebral ischemia. A core of 26 genes that are different in patients with cerebral ischemia from patients without transient ischemia was identified. There is currently no blood test for cerebral ischemia in TIA, and brain imaging is usually negative when ischemia is transient. It is important to identify ischemic causes of transient neurological events because they are treated with vascular prevention therapy. Non ischemic causes of transient neurological events, such as migraine and seizure, obtain very different therapy and physician follow up. Deciphering whether a transient neurological event is of ischemic or nonischemic etiology is very challenging to physicians relying mostly on clinical history. No blood test currently exists to help with this distinction, and other diagnostic investigations are usually unremarkable.

In one embodiment, the invention provides a blood test for transient cerebral ischemia. Currently, the best way for diagnosing TIA clinical history is with Computerized Axial Tomography or Computed Tomography (CT) or Magnetic Resonance Imaging (MRI) brain scan. However, acute scans of patients with TIA are usually normal. Thus, a blood test for transient cerebral ischemia would complement clinical history which is limited by patient recall and communication abilities, as well as physician ability to elicit relevant information.

The cause of a transient neurological event is often not entirely clear. It is oftentimes not known whether some transient neurological event is caused by cerebral ischemia or other common conditions such as migraine, seizure or syncope/fainting. A blood test to identify cerebral ischemia would help address these questions and guide appropriate therapy for the patient. Ischemic transient neurological events undergo extensive evaluation of the heart, vasculature, blood and brain, and patients receive stroke prevention therapy such as antiplatelet/anticoagulation, anti-hypertensive medication and lipid lowering therapy. Patients with non-ischemic transient neurological events undergo different diagnostic evaluation and therapy, such as EEG and anti-seizure medication for seizures, and anti-migraine medication for migraines.

The biomarkers and blood test described herein for identifying cerebral ischemia were also found to identify ischemia in other organs. In 3 patients with pulmonary embolism (i.e., ischemia of the lungs) ischemia was correctly identified. In 17 patients with myocardial infarction (i.e., ischemia of the heart) ischemia was correctly identified in 16/17 patients. Thus, though discovered to identify ischemia in the brain, applications of the present biomarkers to other organ ischemia exist. A diagnostic blood test for pulmonary embolism lacks sufficient sensitivity. Currently, imaging of the lungs is required using ventilation/perfusion (V/Q) scans and CT scan of the pulmonary vasculature, both of which often demonstrate equivocal findings, are costly, and are challenging to interpret.

2. Subjects Who can Benefit from the Present Methods

Individuals who will benefit from the present methods may be exhibiting symptoms of a transient neurological event, ischemic or non-ischemic. Alternatively, the subject may be suspected of having experienced a transient neurological event, ischemic or non-ischemic. In some embodiments, the subject has not experienced and/or is not at risk of having an intracerebral hemorrhage. In some embodiments, the subject has not experienced and/or is not at risk of having an intracerebral hemorrhage or hemorrhagic stroke. In some embodiments, the subject has been diagnosed as having not experienced and/or not at risk of having an intracerebral hemorrhage or hemorrhagic stroke.

In some embodiments, the levels of expression of the panel of biomarkers is determined within 3 hours of a suspected ischemic event. In some embodiments, the levels of expression of the panel of biomarkers are determined at 3 or more hours after a suspected ischemic event. In some embodiments, the levels of expression of the panel of biomarkers are determined within 6, 12, 18, 24, 36, 48 hours of a suspected ischemic event.

In some cases, the subject is asymptomatic, but may have a risk or predisposition to experiencing ischemia or TIA, e.g., based on genetics, a related disease condition, environment or lifestyle. For example, in some embodiments, the patient suffers from a chronic inflammatory condition, e.g., has an autoimmune disease (e.g., rheumatoid arthritis, Crohn's disease inflammatory bowel disease), atherosclerosis, hypertension, or diabetes. In some embodiments, the patient has high LDL-cholesterol levels or suffers from a cardiovascular disease (e.g., atherosclerosis, coronary artery disease). In some embodiments, the patient has an endocrine system disorder, a neurodegenerative disorder, a connective tissue disorder, or a skeletal and muscular disorder. Exemplary disorders associated with, related to, or causative of TIA are discussed in co-pending application Ser. No. 13/182,630 and PCT/US2011/044023, which are hereby incorporated herein by reference in their entirety for all purposes. In various embodiments, the subject has one or more vascular risk factors (e.g., hypertension, diabetes mellitus, hyperlipidemia, or tobacco smoking). In some embodiments, the subject has an ABCD score that is 4 or greater (see, e.g., Josephson, et al., *Stroke*. (2008) 39(11):3096-8; Rothwell et al., *Lancet* (2005) 366(9479):29-36; and Johnston, et al., *Lancet*. (2007) 369(9558):283-92).

3. Biomarkers Indicative of the Occurrence or Risk of Ischemia

Biomarkers useful for the prediction, diagnosis or confirmation of the occurrence of ischemia (e.g., cerebral ischemia, myocardial ischemia, pulmonary ischemia), and/or for distinguishing a transient neurological event (TNE) as ischemic or non-ischemic are listed in Tables 3 and/or 5. Determination of the expression levels of a plurality of the biomarkers of Tables 3 and/or 5 can be performed for the prediction, diagnosis or confirmation of the occurrence of ischemia in conjunction with other biomarkers known in the art for the prediction, diagnosis or confirmation of the occurrence of ischemic stroke, in conjunction with other methods known in the art for the diagnosis of ischemic stroke, in conjunction with biomarkers described herein and known in the art useful for determining the cause of ischemic stroke and/or in conjunction with methods known in the art for determining the cause of ischemic stroke. Such biomarkers are described in co-pending and co-owned U.S. patent application Ser. Nos. 12/598,107; 13/182,779; 13/182,630; PCT/US2011/044062, PCT/US2011/044023 and 61/449,347, each of which is hereby incorporated herein by reference in its entirety for all purposes.

Determination of the expression levels of a plurality of the biomarkers of Tables 3 and/or 5 can be performed for the prediction, diagnosis or confirmation of the occurrence of ischemia can also be performed independently, e.g., to diagnose that ischemia has occurred, to distinguish a TNE as ischemic or non-ischemic, or to determine the risk that a patient may suffer an ischemic event.

As appropriate, the expression levels of at least about 3, 5, 10, 15, 20, 25, 30, 40, 50, 60, 70, 80 or more biomarkers from Table 3 and/or Table 5 are determined. In some embodiments, the expression levels of a plurality of biomarkers in Table 3 or Table 5 are determined. In some embodiments, the expression levels of all listed biomarkers in Table 3 and/or Table 5 are determined.

In some embodiments, the level of expression of biomarkers indicative of the occurrence of ischemia is determined within 72 hours, for example, within 60, 48, 36, 24, 12, 6 or 3 hours of a suspected ischemic event. In various embodiments, an increased expression level of one or more ischemia-associated biomarkers of Table 3 selected from the group consisting of UBE2J1, ELAVL3, FCGR2B, BLVRA, JMJD6, DDAH2, PTRH2, CARD16, CAV1, ZNF608, NDUFB3, 5LC22A4, PCMT1, CACNA1A, CASP1 and LOC100129105, is correlative with or indicates that the patient suffers from or is at risk of developing ischemia or that the patient experienced or is at risk of experiencing an ischemic transient neurological event. In various embodiments, an increased expression level of one or more ischemia-associated biomarkers of Table 3 selected from the group consisting of UBE2J1, CARD16, LOC203274, ZNF608, CARD16///CASP1, UBE2J1, PTRH2, ANXA3, FCGR2B, C14orf101, LOC100129105, DDAH2, RAB27A, AIM2, CASP5, HNRNPH2, RAB27A, SHOX2, CNIH4, TLR10, ZEB2, NDUFB3, CYTH4, BLVRA, FLJ39051, SLC22A4, DNAH17, SPATA4, CACNA1A, CASP1, PGS1, LTBR, FCGR1B, IGFBP5, LTB, N4BP2L2, DRAM1, WIT1, ELAVL3, FKBP15, JMJD6, CAV1 and PCMT1 is correlative with or indicates that the patient suffers from or is at risk of developing ischemia or that the patient experienced or is at risk of experiencing an ischemic transient neurological event. In various embodiments, a decreased expression level of one or more ischemia-associated biomarkers of Table 3 selected from the group consisting of AK5, DIP2A, ETS1, CCND3, GNE, BCL9L, SPATA5, and LBH is correlative with or indicates that the patient suffers from or is at risk of developing ischemia or that the patient experienced or is at risk of experiencing an ischemic transient neurological event. In various embodiments, a decreased expression level of one or more ischemia-associated biomarkers of Table 3 selected from the group consisting of FOXK1, AK5, APBA2, NUCKS1, NEIL2, WHAMML1///WHAMML2, GLG1, CCND3, LBH, TAF3, TBC1D10A, FMNL3, SPATA5, ZMYND11, CAPN5, GNE, MMP19, ZNF609, ETS1, BCL9L, DIP2A, APBB1, NPTXR is correlative with or indicates that the patient suffers from or is at risk of developing ischemia or that the patient experienced or is at risk of experiencing an ischemic transient neurological event.

Conversely, in various embodiments, a decreased expression level of one or more ischemia-associated biomarkers of Table 3 selected from the group consisting of UBE2J1, ELAVL3, FCGR2B, BLVRA, JMJD6, DDAH2, PTRH2, CARD16, CAV1, ZNF608, NDUFB3, SLC22A4, PCMT1, CACNA1A, CASP1 and LOC100129105, is correlative with or indicates that the patient does not suffer from or is not at risk of developing ischemia or that the patient has not experienced or is not at risk of experiencing an ischemic transient neurological event. In various embodiments, a decreased expression level of one or more ischemia-associated biomarkers of Table 3 selected from the group consisting of UBE2J1, CARD16, LOC203274, ZNF608, CARD16///CASP1, UBE2J1, PTRH2, ANXA3, FCGR2B, C14orf101, LOC100129105, DDAH2, RAB27A, AIM2, CASP5, HNRNPH2, RAB27A, SHOX2, CNIH4, TLR10, ZEB2, NDUFB3, CYTH4, BLVRA, FLJ39051, SLC22A4, DNAH17, SPATA4, CACNA1A, CASP1, PGS1, LTBR, FCGR1B, IGFBP5, LTB, N4BP2L2, DRAM1, WIT1, ELAVL3, FKBP15, JMJD6, CAV1 and PCMT1 is correlative with or indicates that the patient does not suffer from or is not at risk of developing ischemia or that the patient experienced or is at risk of experiencing an ischemic transient neurological event. In various embodiments, an increased expression level of one or more ischemia-associated biomarkers of Table 3 selected from the group consisting of AK5, DIP2A, ETS1, CCND3, GNE, BCL9L, SPATA5, and LBH is correlative with or indicates that the patient does not suffer from or is not at risk of developing ischemia or that the patient has not experienced or is not at risk of experiencing an ischemic transient neurological event. In various embodiments, an increased expression level of one or more ischemia-associated biomarkers of Table 3 selected from the group consisting of FOXK1, AK5, APBA2, NUCKS1, NEIL2, WHAMML1///WHAMML2, GLG1, CCND3, LBH, TAF3, TBC1D10A, FMNL3, SPATA5, ZMYND11, CAPN5, GNE, MMP19, ZNF609, ETS1, BCL9L, DIP2A, APBB1, NPTXR is correlative with or indicates that the patient does not suffer from or is not at risk of developing ischemia or that the patient experienced or is at risk of experiencing an ischemic transient neurological event.

In various embodiments, an increased expression level of one or more ischemia-associated biomarkers of Table 3 selected from the group consisting of AIM2, C14orf101, DNAH17, UBE2J1, LOC203274, PGS1, ZEB2, DDAH2, CARD16, SPATA4, ANXA3, WIT1, FCGR2B, CACNA1A, FKBP15, N4BP2L2, HNRNPH2, ELAVL3, ZNF608, TLR10, BLVRA, SLC22A4, RAB27A, LTBR, CARD16///CASP1, IGFBP5, CASP5, LTB, NDUFB3, SHOX2, CAV1, CNIH4, FLJ39051, CASP1, PTRH2, LOC100129105, PCMT1, CYTH4, JMJD6, DRAM1, FCGR1B, is correlative with or indicates that the patient suffers from or is at risk of developing ischemia or that the patient experienced or is at risk of experiencing an ischemic transient neurological event. In various embodiments, a decreased expression level of one or more ischemia-associated biomarkers of Table 3 selected from the group consisting of NEIL2, FOXK1, NUCKS1, MMP19, APBA2, SPATA5, BCL9L, GLG1, CCND3, TBC1D10A, AK5, ZNF609, ETS1, WHAMML1///WHAMML2, GNE, NPTXR, DIP2A, LBH, APBB1, ZMYND11, CAPN5, TAF3 and FMNL3 is correlative with or indicates that the patient suffers from or is at risk of developing ischemia or that the patient experienced or is at risk of experiencing an ischemic transient neurological event.

Conversely, in various embodiments, a decreased expression level of one or more ischemia-associated biomarkers of Table 3 selected from the group consisting of AIM2, C14orf101, DNAH17, UBE2J1, LOC203274, PGS1, ZEB2, DDAH2, CARD16, SPATA4, ANXA3, WIT1, FCGR2B, CACNA1A, FKBP15, N4BP2L2, HNRNPH2, ELAVL3, ZNF608, TLR10, BLVRA, SLC22A4, RAB27A, LTBR, CARD16///CASP1, IGFBP5, CASP5, LTB, NDUFB3, SHOX2, CAV1, CNIH4, FLJ39051, CASP1, PTRH2, LOC100129105, PCMT1, CYTH4, JMJD6, DRAM1, FCGR1B, is correlative with or indicates that the patient does not suffer from or is not at risk of developing ischemia or that the patient has not experienced or is not at risk of experiencing an ischemic transient neurological event. In various embodiments, an increased expression level of one or more ischemia-associated biomarkers of Table 3 selected from the group consisting of NEIL2, FOXK1, NUCKS1, MMP19, APBA2, SPATA5, BCL9L, GLG1, CCND3, TBC1D10A, AK5, ZNF609, ETS1, WHAMML1///WHAMML2, GNE, NPTXR, DIP2A, LBH, APBB1, ZMYND11, CAPN5, TAF3 and FMNL3 is correlative with or indicates that the patient does not suffer from or is not at risk of developing ischemia or that the patient has not experienced or is not at risk of experiencing an ischemic transient neurological event. In various embodiments, an increased expression level of one or more ischemia-associated biomarkers of Table 3 selected from the group consisting of UBE2J1, CARD16, LOC203274, ZNF608, CARD16///CASP1, PTRH2, ANXA3, FCGR2B, C14orf101, LOC100129105, DDAH2, RAB27A, AIM2, CASP5, HNRNPH2, RAB27A, SHOX2, CNIH4, TLR10, ZEB2, NDUFB3, CYTH4, BLVRA, FLJ39051, SLC22A4, DNAH17, SPATA4, CACNA1A, CASP1, PGS1, LTBR, FCGR1B, IGFBP5, LTB, N4BP2L2, DRAM1, WIT1, ELAVL3, FKBP15, JMJD6, CAV1 and PCMT1 is correlative with or indicates that the patient does not suffer from or is not at risk of developing ischemia or that the patient has not experienced or is not at risk of experiencing an ischemic transient neurological event.

In various embodiments, an increased expression level of one or more ischemia-associated biomarkers of Table 5 selected from the group consisting of CARD16, IRF7, TLR6, NMU, C13orf16, TAPBP, BTC, ZBP1, HSPA6, TWIST1, PLSCR1, SAMD9L, OSTCL, C9orf66, GYPA, ADM, ANKRD22, SHOX, ZNF354A, SRGAP1, GRM5, BAGE, XRCC4, SLC37A3, OVOL2, LIFR, RASAL2, hCG_1749898, IQGAP3, HS3ST3A1, NPR3, SIX3 and HCN1, is correlative with or indicates that the patient suffers from or is at risk of developing ischemia or that the patient experienced or is at risk of experiencing an ischemic transient neurological event. In various embodiments, a decreased expression level of one or more ischemia-associated biomarkers of Table 5 selected from the group consisting of CAND1, GUSBL2, SLC3A1, ALDH6A1, CLTC, FUS, RANBP10, KIAA0391, MED1, NAPEPLD, KIAA1919, HCFC1, TPP2, G3BP1, PRDX6, YARS, PYGB, YBX1///YBX1P2, FUS///NR1H3, GCAT, CAPN5, LOC100129656, SMARCC2, HELLS, MAP2K7, ZNF652, GSTM1, C16orf35, KIAA1659, GSTM2, LOC440104, VTI1A, HERC1, ALS2CL, GSTM1, GCAT, ERMN, LOC100293532, IFT80, RBM6, BAZ1B, HNRNPUL2, ENTPD5, ATXN2L, LPIN1, METTL3, MBNL2, SMURF2, C20orf196, UNC84A, DCAF16 and EIF3B is correlative with or indicates that the patient suffers from or is at risk of developing ischemia or that the patient experienced or is at risk of experiencing an ischemic transient neurological event. Conversely, a decreased expression level of one or more ischemia-associated biomarkers of Table 5 selected from the group consisting of CARD16, IRF7, TLR6, NMU, C13orf16, TAPBP, BTC, ZBP1, HSPA6, TWIST1, PLSCR1, SAMD9L, OSTCL, C9orf66, GYPA, ADM, ANKRD22, SHOX, ZNF354A, SRGAP1, GRM5, BAGE, XRCC4, SLC37A3, OVOL2, LIFR, RASAL2, hCG_1749898, IQGAP3, HS3ST3A1, NPR3, SIX3 and HCN1, is correlative with or indicates that the patient does not suffer from or is not at risk of developing ischemia or that the patient has not experienced or is not at risk of experiencing an ischemic transient neurological event. In various embodiments, an increased expression level of one or more ischemia-associated biomarkers of Table 5 selected from the group consisting of CAND1, GUSBL2, SLC3A1, ALDH6A1, CLTC, FUS, RANBP10, KIAA0391, MED1, NAPEPLD, KIAA1919, HCFC1, TPP2, G3BP1, PRDX6, YARS, PYGB, YBX1///YBX1P2, FUS///NR1H3, GCAT, CAPN5, LOC100129656, SMARCC2, HELLS, MAP2K7, ZNF652, GSTM1, C16orf35, KIAA1659, GSTM2, LOC440104, VTI1A, HERC1, ALS2CL, GSTM1, GCAT, ERMN, LOC100293532, IFT80, RBM6, BAZ1B, HNRN-PUL2, ENTPD5, ATXN2L, LPIN1, METTL3, MBNL2, SMURF2, C20orf196, UNC84A, DCAF16 and EIF3B is correlative with or indicates that the patient does not suffer from or is not at risk of developing ischemia or that the patient has not experienced or is not at risk of experiencing an ischemic transient neurological event.

The overexpression or the underexpression of the biomarkers are determined with reference to a control level of expression. The control level of expression can be determined using any method known in the art. For example, the control level of expression can be from a population of individuals known to not have or be at risk for an ischemic event or can be determined with reference to a panel of stably expressed reference biomarkers. Also, threshold levels of expression can be determined based on levels of expression in predetermined populations (e.g., known to not have or be at risk for an ischemic event versus known to have or be at risk for ischemia). Overexpression or underexpression of a plurality of biomarkers from Table 3 and/or Table 5 that is at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, or more, in comparison to the expression levels of a plurality of stably expressed endogenous reference biomarkers, e.g., those listed in Table 10, is correlative with or indicates that the subject has experienced or is at risk of experiencing an ischemic event. Overexpression or underexpression of a plurality of biomarkers from Table 3 and/or Table 5 that is at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, or more, in comparison to the expression level of the same biomarker in an individual or a population of individuals who have not experienced a vascular event is correlative with or indicates that the subject has experienced or is at risk of experiencing an ischemic event.

Biomarkers useful for the determination and diagnosis of the cause of stroke are described, e.g., in co-owned and co-pending U.S. patent application Ser. No. 12/598,107; 13/182,779; 13/182,630; PCT/US2011/044062, PCT/US2011/044023 and 61/449,347, each of which is hereby incorporated herein by reference in its entirety for all purposes. In addition to evaluating the expression levels of a plurality of biomarkers useful for identifying the occurrence of ischemia and/or for distinguishing a transient neurological event as ischemic or non-ischemic, the expression levels of a plurality of biomarkers can be measured to determine whether a suspected or predicted ischemic event is cardioembolic or atherosclerotic. Furthermore, the expression levels of a plurality of biomarkers can be measured to determine if the cause of stroke is due to carotid stenosis, atrial fibrillation, lacunar stroke or transient ischemic attacks. Classification of stroke subtypes is known in the art and reviewed in, e.g., in Amarenco, et al., Cerebrovasc Dis (2009) 27:493-501. Accordingly, in some embodiments, the expression levels of at least about 3, 5, 10, 15, 20, 25, 30, 40, 50, 60, 70, 80, 85, 100, 200, 500, 1000 or more, ischemic stroke-associated biomarkers are independently determined. In some embodiments, the expression levels of all ischemic stroke-associated biomarkers in a panel are determined.

In various embodiments, the expression levels of a plurality of ischemia-associated genes are co-determined together with the expression levels of a plurality of genes useful in the determination of whether a patient has experienced or has a predisposition to experience cardioembolic stroke (a.k.a., cardiac embolism, cardioembolism emboligenic heart disease). A cardioembolic stroke occurs when a thrombus (clot) dislodges from the heart, travels through the cardiovascular system and lodges in the brain, first cutting off the blood supply and then often causing a hemorrhagic bleed. In some embodiments an increased expression level of one or more ischemic stroke-associated biomarkers selected from the group consisting of IRF6 (NM_006147), ZNF254 (NM_203282), GRM5 (NM_000842///NM_001143831), EXT2 (NM_000401///NM_207122), AP3S2 (NM_005829///NR_023361), PIK3C2B (NM_002646), ARHGEF5 (NM_005435), COL13A1 (NM_001130103///NM_005203///NM_080798///NM_080799///NM_080800///NM_080801///NM_080802///NM_080803///NM_080804///NM_080805///NM_080806///NM_080807///NM_080808///NM_080809///NM_080810///NM_080811///NM_080812///NM_080813///NM_080814///NM_080815), PTPN20A///PTPN20B (NM_001042357///NM_001042358///NM_001042359///NM_001042360///NM_001042361///NM_001042362///NM_001042363///NM_001042364///NM_001042365///NM_001042387///NM_001042389///NM_001042390///NM_001042391///NM_001042392///NM_001042393///NM_001042394///NM_001042395///NM_001042396///NM_001042397///NM_015605), LHFP (NM_005780), BANK1 (NM_001083907///NM_001127507///NM_017935), HLA-DOA (NM_002119), EBF1 (NM_024007), TMEM19 (NM_018279), LHFP (NM_005780), FCRL1 (NM_001159397///NM_001159398///NM_052938), OOEP (NM_001080507) and LRRC37A3 (NM_199340) is correlative with or indicates that the patient has experienced or is at risk for cardioembolic stroke. In some embodiments, a decreased expression level of one or more ischemic stroke-associated biomarkers selected from the group consisting of LOC284751 (NM_001025463), CD46 (NM_002389///NM_153826///NM_172350///NM_172351///NM_172352///NM_172353///NM_172354///NM_172355///NM_172356///NM_172357///NM_172358///NM_172359///NM_172360///NM_172361), ENPP2 (NM_001040092///NM_001130863///NM_006209), C19orf28 (NM_001042680///NM_021731///NM_174983), TSKS (NM_021733), CHURC1 (NM_145165), ADAMTSL4 (NM_019032///NM_025008), FLJ40125 (NM_001080401), CLEC18A (NM_001136214///NM_182619), ARHGEF12 (NM_015313), C16orf68 (NM_024109), TFDP1

(NM_007111///NR_026580) and GSTK1 (NM_001143679///NM_001143680///NM_001143681///NM_015917) is correlative with or indicates that the patient has experienced or is at risk for cardioembolic stroke.

In various embodiments, the expression levels of a plurality of ischemia-associated genes are co-determined together with the expression levels of a plurality of genes useful in the determination of whether a patient has experienced or has a predisposition to experience carotid stenosis. Carotid stenosis is a narrowing or constriction of the inner surface (lumen) of the carotid artery, usually caused by atherosclerosis. An inflammatory buildup of plaque can narrow the carotid artery and can be a source of embolization. Emboli break off from the plaque and travel through the circulation to blood vessels in the brain, causing ischemia that can either be temporary (e.g., a transient ischemic attack), or permanent resulting in a thromboembolic stroke (a.k.a., atherothrombosis, large-artery atherosclerosis, atherosclerosis with stenosis). In some embodiments, an increased expression level of one or more ischemic stroke-associated biomarkers selected from the group consisting of NT5E (NM_002526), CLASP2 (NM_015097), GRM5 (NM_000842///NM_001143831), PROCR (NM_006404), ARHGEF5 (NM_005435), AKR1C3 (NM_003739), COL13A1 (NM_001130103///NM_005203///NM_080798///NM_080799///NM_080800///NM_080801///NM_080802///NM_080803///NM_080804///NM_080805///NM_080806///NM_080807///NM_080808///NM_080809///NM_080810///NM_080811///NM_080812///NM_080813///NM_080814///NM_080815), LHFP (NM_005780), RNF7 (NM_014245///NM_183237), CYTH3 (NM_004227), EBF1 (NM_024007), RANBP10 (NM_020850), PRSS35 (NM_153362), C12orf42 (NM_001099336///NM_198521) and LOC100127980 (XM_001720119///XM_001722650) is correlative with or indicates that the patient has experienced or is at risk for carotid stenosis. In some embodiments, a decreased expression level of one or more ischemic stroke-associated biomarkers selected from the group consisting of FLJ31945 (XM_001714983///XM_001716811///XM_001718431), LOC284751 (NM_001025463), LOC100271832 (NR_027097), MTBP (NM_022045), ICAM4 (NM_001039132///NM_001544///NM_022377), SHOX2 (NM_001163678///NM_003030///NM_006884), DOPEY2 (NM_005128), CMBL (NM_138809), LOC146880 (NR_026899///NR_027487), SLC20A1 (NM_005415), SLC6A19 (NM_001003841), ARHGEF12 (NM_015313), C16orf68 (NM_024109), GIPC2 (NM_017655) and LOC100144603 (NR_021492) is correlative with or indicates that the patient has experienced or is at risk for carotid stenosis.

In various embodiments, the expression levels of a plurality of ischemia-associated genes are co-determined together with the expression levels of a plurality of genes useful in the determination of whether a patient has experienced or has a predisposition to experience atrial fibrillation. Atrial fibrillation (AF or A-fib) is the most common cardiac arrhythmia and involves the two upper chambers (atria) of the heart fibrillating (i.e., quivering) instead of a coordinated contraction. In some instances, cardioembolic stroke can occur as a result of atrial fibrillation. Cardioembolic stroke can be a downstream result of atrial fibrillation in that stagnant blood in the fibrillating atrium can form a thrombus that then embolises to the cerebral circulation, blocking arterial blood flow and causing ischaemic injury. In some embodiments, an increased expression level of one or more ischemic stroke-associated biomarkers selected from the group consisting of SMC1A (NM_006306), SNORA68 (NR_000012), GRLF1 (NM_004491), SDC4 (NM_002999), HIPK2 (NM_001113239///NM_022740///XM_001716827///XM_925800), LOC100129034 (NR_027406///XR_079577), CMTM1 (NM_052999///NM_181268///NM_181269///NM_181270///NM_181271///NM_181272///NM_181283///NM_181296) and TTC7A (NM_020458) is correlative with or indicates that the patient has experienced or is at risk for atrial fibrillation. In some embodiments, a decreased expression level of one or more ischemic stroke-associated biomarkers selected from the group consisting of LRRC43 (NM_001098519///NM_152759), MIF///SLC2A11 (NM_001024938///NM_001024939///NM_002415///NM_030807), PER3 (NM_016831), PPIE (NM_006112///NM_203456///NM_203457), COL13A1 (NM_001130103///NM_005203///NM_080798///NM_080799///NM_080800///NM_080801///NM_080802///NM_080803///NM_080804///NM_080805///NM_080806///NM_080807///NM_080808///NM_080809///NM_080810///NM_080811///NM_080812///NM_080813///NM_080814///NM_080815), DUSP16 (NM_030640), BRUNOL6 (NM_052840), GPR176 (NM_007223), C6orf164 (NR_026784) and MAP3K7IP1 (NM_006116///NM_153497) is correlative with or indicates that the patient has experienced or is at risk for atrial fibrillation.

In various embodiments, the expression levels of a plurality of ischemia-associated genes are co-determined together with the expression levels of a plurality of genes useful in the determination of whether a patient has experienced or has a predisposition to experience transient ischemic attacks (TIA). A transient ischemic attack is a change in the blood supply to a particular area of the brain, resulting in brief neurologic dysfunction that persists, by definition, for less than 24 hours. If symptoms persist longer, then it is categorized as a stroke. In some embodiments, an increased expression level of one or more TIA-associated biomarkers selected from the group consisting of GABRB2 (NM_000813///NM_021911), ELAVL3 (NM_001420///NM_032281), COL1A1 (NM_000088), SHOX2 (NM_003030///NM_006884), TWIST1 (NM_000474), DPPA4 (NM_018189), DKFZP434P211 (NR_003714), WIT1 (NM_015855///NR_023920), SOX9 (NM_000346), DLX6 (NM_005222), ANXA3 (NM_005139), EPHA3 (NM_005233///NM_182644), SOX11 (NM_003108), SLC26A8 (NM_052961///NM_138718), CCRL1 (NM_016557///NM_178445), FREM2 (NM_207361), STOX2 (NM_020225), ZNF479 (NM_033273///XM_001714591///XM_001719979), LOC338862 (NR_038878.1), ASTN2 (NM_014010///NM_198186///NM_198187///NM_198188), FOLH1 (NM_001014986///NM_004476), SNX31 (NM_152628), KREMEN1 (NM_001039570///NM_001039571), ALS2CR11 (NM_152525), FIGN (NM_018086), RORB (NM_006914), LOC732096 (XM_001720784///XM_001725388///XR_016064), GYPA (NM_002099), ALPL (NM_000478///NM_001127501), LHX2 (NM_004789), GALNT5 (NM_014568), SRD5A2L2 (NM_001010874), GALNT14 (NM_024572), OVOL2 (NM_021220), BMPR1B (NM_001203), UNC5B (NM_170744), ODZ2 (NM_001080428///NM_001122679), RASAL2 (NM_004841///NM_170692), SHOX (NM_000451///NM_006883), C19orf59 (NM_174918), ZNFLJ4 (NM_153608), SRGAP1 (NM_020762), ELAVL2 (NM_004432), NCRNA00032 (XM_376821///XM_938938), LOC440345 (XR_015786), FLJ30375 (XM_001724993///XM_001725199///XM_001725628), TFPI (NM_001032281///NM_006287), PTGR1 (NM_012212), ROBO1 (NM_002941///NM_133631), NR2F2 (NM_021005), GRM5 (NM_000842///NM_001143831), LUM (NM_002345), FLJ39051 (NR_033839.1), COL1A2 (NM_000089), CASP5 (NM_001136109///NM_001136110///NM_001136111///NM_001136112///NM_004347//), OPCML (NM_001012393///NM_002545), TTC6 (NM_001007795), TFAP2B (NM_003221), CRISP2 (NM_001142407///NM_001142408///NM_001142417///NM_001142435///NM_003296), SOX11 (NM_003108), ANKRD30B (XM_001716904///XM_001717561///XM_001717810), SCN2A (NM_001040142///NM_001040143///NM_021007), MYNN (NM_018657), FOXA2 (NM_021784///NM_153675), DKFZP434B061 (XR_015528///XR_040812), LOC645323 (NR_015436///NR_024383///NR_024384///XR_041118///XR_041119///XR_041120), SNIP (NM_025248), LOC374491 (NR_002815), ADAM30 (NM_021794), SIX3 (NM_005413), FLJ36144 (XR_040632///XR_040633///XR_040634), CARD8 (NM_014959), RP1-127L4.6 (NM_001010859), FAM149A (NM_001006655///NM_015398), B3GAT2 (NM_080742), SPOCK3 (NM_001040159///NM_016950), ITGBL1 (NM_004791), IQGAP3 (NM_178229), C7orf45 (NM_145268), ZNF608 (NM_020747), LOC375010 (XR_041271), LRP2 (NM_004525), TGFB2 (NM_001135599///NM_003238), SHOX2 (NM_003030///NM_006884), HOXC4///HOXC6 (NM_004503///NM_014620///NM_153633///NM_153693), ELTD1 (NM_022159), FAM182B///RP13-401N8.2 (XM_001132551///XM_001133521///XM_001718365///XM_933752), LIFR (NM_001127671///NM_002310), FOLH1 (NM_001014986///NM_004476), EHF (NM_012153), NDST3 (NM_004784), BRUNOL5 (NM_021938), LOC728460 (XM_001128581///XM_001129498///XM_001723364), PDE1A (NM_001003683///NM_005019), POU2AF1 (NM_006235), FAT1 (NM_005245), PCDH11X///PCDH11Y (NM_014522///NM_032967///NM_032968///NM_032969///NM_032971///NM_032972), FLJ37786 (XR_041472///XR_041473), SLC22A4 (NM_003059), DHRS13 (NM_144683), MEG3 (NR_002766///NR_003530///NR_003531), PIWIL1 (NM_004764), LOC203274 (AL117607.1///BC080605.1), LOC100133920///LOC286297 (NR_024443///XM_001714612///XM_372109///XM_933054///XM_933058), DMRT1 (NM_021951), ADM (NM_001124), VWA3B (NM_144992), GAFA3 (XM_001715321///XM_001722922///XM_001723636), HESX1 (NM_003865), ADAMDEC1 (NM_014479), CAV1 (NM_001753), LAMB4 (NM_007356), TPTE (NM_199259///NM_199260///NM_199261), PPP1R1C (NM_001080545), HPSE (NM_001098540///NM_006665), AIM2 (NM_004833), RUNDC3B (NM_001134405///NM_001134406///NM_138290), CARD16 (NM_001017534///NM_052889), FAM124A (NM_145019), MGC39584 (XR_017735///XR_017787///XR_041937), OSM (NM_020530), RFX2 (NM_000635///NM_134433), MYBPC1 (NM_002465///NM_206819///NM_206820///NM_206821), LTBR (NM_002342), C18orf2 (NM_031416///NR_023925///NR_023926///NR_023927///NR_023928), SNRPN (NM_003097///NM_022805///NM_022806///NM_022807///NM_022808///NR_001289), FLJ36031 (NM_175884), IL1B (NM_000576), TRPM1 (NM_002420), OSTCL (NM_145303), MAPK14 (NM_001315///NM_139012///NM_139013///NM_139014), KCNJ15///LOC100131955 (NM_002243///NM_170736///NM_170737///XM_001713900///XM_001715532///XM_0), FIGN (NM_018086), HNT (NM_001048209///NM_016522), S100A12 (NM_005621), CHIT1 (NM_003465), C7orf53 (NM_001134468///NM_182597), FAM13A1 (NM_001015045///NM_014883), GNAO1 (NM_020988///NM_138736), MAPK14 (NM_001315///NM_139012///NM_139013///NM_139014), FAM55D (NM_001077639///NM_017678), PRKD2 (NM_001079880///NM_001079881///NM_001079882///NM_016457), LIMK2 (NM_001031801///NM_005569///NM_016733), C18orf54 (NM_173529), IGFBP5 (NM_000599), EVI1 (NM_001105077///NM_001105078///NM_005241), PLSCR1 (NM_021105), FOXC1 (NM_001453), LOC646627 (NM_001085474), ZNF462 (NM_021224), CNTLN (NM_001114395///NM_017738), ZNF438 (NM_001143766///NM_001143767///NM_001143768///NM_001143769///NM_001143770), DEFB105A///DEFB105B (NM_001040703///NM_152250), LOC340017 (NR_026992.1), C1orf67 (NM_144989), ACSL1 (NM_001995), ADH1B (NM_000668), SLC2A14///SLC2A3 (NM_006931///NM_153449), IL1B (NM_000576), ST3GAL4 (NM_006278///XM_001714343///XM_001726541///XM_001726562), UBE2J1 (NM_016021), PNPLA3 (NM_025225) and PAPPA (NM_002581) is correlative with or indicates that the patient has experienced or is at risk for TIA. In some embodiments, a decreased expression level of one or more TIA-associated biomarkers selected from the group consisting of NBPF10///RP11-94I2.2 (NM_001039703///NM_183372///XM_001722184), SFXN1 (NM_022754), SPIN3 (NM_001010862), UNC84A (NM_001130965///NM_025154), OLFM2 (NM_058164), PPM1K (NM_152542), P2RY10 (NM_014499///NM_198333), ZNF512B (NM_020713), MORF4L2 (NM_001142418///NM_001142419///NM_001142420///NM_001142421///NM_001142422), GIGYF2 (NM_001103146///NM_001103147///NM_001103148///NM_015575), ERAP2 (NM_001130140///NM_022350), SLFN13 (NM_144682), LOC401431 (XR_040272///XR_040273///XR_040274///XR_040275), MED6 (NM_005466), BAIAP2L1///LOC100128461 (NM_018842///XM_001722656///XM_001724217///XM_001724858), LNPEP (NM_005575///NM_175920), MBNL1 (NM_021038///NM_207292///NM_207293///NM_207294///NM_207295///NM_207296), NOS3 (NM_000603), MCF2L (NM_001112732///NM_024979), KIAA1659 (XM_001723799///XM_001725435///XM_001726785), SCAMP5 (NM_138967), LOC648921 (XM_001715629///XM_001720571///XR_018520), ANAPC5 (NM_001137559///NM_016237), SPON1 (NM_006108), FUS (NM_004960), GPR22 (NM_005295), GAL3ST4 (NM_024637), METTL3 (NM_019852), LOC100131096 (XM_001720907///XM_001726205///XM_001726705), FAAH2 (NM_174912), SMURF2 (NM_022739), SNRPN (NM_003097///NM_022805///NM_022806///NM_022807///NM_022808///NR_001289), FBLN7 (NM_001128165///NM_153214), GLS (NM_014905), G3BP1 (NM_005754///NM_198395), RCAN3 (NM_013441), EPHX2 (NM_001979), DIP2C (NM_014974), CCDC141 (NM_173648), CLTC (NM_004859), FOSB (NM_001114171///NM_006732), CACNA1I (NM_001003406///NM_021096), UNQ6228 (XM_001725293///XM_001725359///XM 001726164), ATG9B (NM_173681), AK5 (NM_012093///NM_174858), RBM14 (NM_006328), MAN1C1 (NM_020379), HELLS (NM_018063), EDAR (NM_022336), SLC3A1 (NM_000341), ZNF519 (NM_145287), LOC100130070///LOC100130775///LOC100131787///LOC100131905///

LOC100132291///LOC100132488///RP527 (NM_001030///XM_001721002///XM_001722161///XM_001722965///XM_001723889//), ZC3H12B (NM_001010888), IQGAP2 (NM_006633), SOX8 (NM_014587), WHDC1L2 (XM_926785), TNPO1 (NM_002270///NM_153188), TNFRSF21 (NM_014452), TSHZ2 (NM_173485), DMRTC1///DMRTC1B (NM_001080851///NM_033053), GSTM1 (NM_000561///NM_146421), GSTM2 (NM_000848///NM_001142368), PNMA6A (NM_032882), CAND1 (NM_018448), CCND3 (NM_001136017///NM_001136125///NM_001136126///NM_001760), GSTM1 (NM_000561///NM_146421), and GUSBL2 (NR_003660///XR_042150///XR_042151) is correlative with or indicates that the patient has experienced or is at risk for TIA.

In various embodiments, the expression levels of a plurality of ischemia-associated genes are co-determined together with the expression levels of a plurality of genes useful in the determination of whether a patient has experienced or has a predisposition to experience lacunar stroke. In some embodiments, an increase of the expression level of one or more biomarkers selected from the group consisting of RASEF (NM_152573), CALM1 (NM_006888), TTC12 (NM_017868), CCL3///CCL3L1///CCL3L3 (NM_001001437///NM_002983///NM_021006), CCDC78 (NM_001031737), PRSS23 (NM_007173), LAIR2 (NM_002288///NM_021270), C18orf49 (AK000229.1///BC047606.1), UTS2 (NM_006786///NM_021995), LGR6 (NM_001017403///NM_001017404///NM_021636), PROCR (NM_006404), LAG3 (NM_002286), OASL (NM_003733///NM_198213), LOC100132181 (XM_001722051.1), HLA-DRB4 (NM_021983///XM_002346251), CCL2 (NM_002982), ALS2CR11 (NM_152525), SCAND2 (NR_003654///NR_004859), GBP4 (NM_052941), RUNX3 (NM_001031680///NM_004350), TSEN54 (NM_207346), UBA7 (NM_003335), FAM179A (NM_199280), TGFBR3 (NM_003243), CCDC114 (NM_144577), AKAP9 (NM_005751///NM_147185), BNC2 (NM_017637), BZRAP1 (NM_004758///NM_024418), CCL4 (NM_002984), CHST2 (NM_004267), CSF1 (NM_000757///NM_172210///NM_172211///NM_172212), ERBB2 (NM_001005862///NM_004448), GBR56 (NM_001145770///NM_001145771///NM_001145772///NM_001145773///NM_001145774), GRAMD3 (NM_001146319///NM_001146320///NM_001146321///NM_001146322///NM_023927), GRHL2 (NM_024915), GRK4 (NM_001004056///NM_001004057///NM_182982), ITIH4 (NM_002218), KIAA1618 (NM_020954), LOC147646 (XM_001134195///XM_001134326///XM_001726058), LOC150622 (NR_026832), LOC161527 (NM_002675///NM_033238///NM_033239///NM_033240///NM_033244///NM_033246), PLEKHF1 (NM_024310), PRKD2 (NM_001079880///NM_001079881///NM_001079882///NM_016457), RGNEF (NM_001080479), SESN2 (NM_031459), SLAMF7 (NM_021181), SPON2 (NM_001128325///NM_012445), STAT1 (NM_007315///NM_139266), SYNGR1 (NM_004711///NM_145731///NM_145738), TRX21 (NM_013351), TMEM67 (NM_001142301///NM_153704///NR_024522), TUBE1 (NM_016262), and ZNF827 (NM_178835), and/or a decrease of the expression level of one or more biomarkers selected from the group consisting of HLA-DQA1 (NM_002122), FLJ13773 (AK023835.1), QKI (NM_006775///NM_206853///NM_206854///NM_206855), MPZL3 (NM_198275), FAM70B (NM_182614), LOC254128 (NR_037856.1///NR_037857.1///NR_037858.1), IL8 (NM_000584), CHML (NM_001821), STX7 (NM_003569), VAPA (NM_003574///NM_194434), UGCG (NM_003358), PDXDC1 (NM_015027), LRRC8B (NM_001134476///NM_015350), STK4 (NM_006282), GTF2H2 (NM_001515), AGFG1 (NM_001135187///NM_001135188///NM_001135189///NM_004504), BTG1 (NM_001731), CFDP1 (NM_006324), CNPY2 (NM_014255), FAM105A (NM_019018), GATM (NM_001482), GTF2H2B (NM_001042490///NM_001098728///NM_001098729///NM_001515), IGHG1 (NG_001019.5///NC_000014.8), IL18RAP (NM_003853), N4BP2 (NM_018177), PHACTR1 (NM_030948), RTKN2 (NM_145307), SLC16A1 (NM_003051), SOCS1 (NM_003745), SPAG17 (NM_206996), ST6GALNAC1 (NM_018414), STK17B (NM_004226), STT3B (NM_178862), STX16 (NM_001001433///NM_001134772///NM_001134773///NM_003763), TBC1D12 (NM_015188), TRIM4 (NM_033017///NM_033091), UACA (NM_001008224///NM_018003), and WHAMML2 (NR_026589) is correlative with or indicates that the patient has experienced or is at risk for experiencing lacunar stroke.

4. Comparison to a Control Level of Expression

The expression of the ischemia-associated biomarkers are compared to a control level of expression. As appropriate, the control level of expression can be the expression level of the same ischemia-associated biomarker in an otherwise healthy individual (e.g., in an individual who has not experienced and/or is not at risk of experiencing ischemia). In some embodiments, the control level of expression is the expression level of a plurality of stably expressed endogenous reference biomarkers, as described herein or known in the art. In some embodiments, the control level of expression is a predetermined threshold level of expression of the same ischemia-associated biomarker, e.g., based on the expression level of the biomarker in a population of otherwise healthy individuals. In some embodiments, the expression level of the ischemia-associated biomarker and the ischemia-associated biomarker in an otherwise healthy individual are normalized to (i.e., divided by), e.g., the expression levels of a plurality of stably expressed endogenous reference biomarkers.

In some embodiments, the overexpression or underexpression of a ischemia-associated biomarker is determined with reference to the expression of the same ischemia-associated biomarker in an otherwise healthy individual. For example, a healthy or normal control individual has not experienced and/or is not at risk of experiencing ischemia. The healthy or normal control individual generally has not experienced a vascular event (e.g., TIA, ischemic stroke, myocardial infarction, peripheral vascular disease, or venous thromboembolism). The healthy or normal control individual generally does not have one or more vascular risk factors (e.g., hypertension, diabetes mellitus, hyperlipidemia, or tobacco smoking). As appropriate, the expression levels of the target ischemia-associated biomarker in the healthy or normal control individual can be normalized (i.e., divided by) the expression levels of a plurality of stably expressed endogenous reference biomarkers.

In some embodiments, the overexpression or underexpression of a ischemia-associated biomarker is determined with reference to one or more stably expressed endogenous reference biomarkers. Internal control biomarkers or endogenous reference biomarkers are expressed at the same or nearly the same expression levels in the blood of patients who have experienced an ischemic event as compared to control patients. Target biomarkers are expressed at higher or lower levels in the blood, serum and/or plasma of patients who have experienced or are at risk of experiencing an ischemic event. The expression levels of the target biomarker to the reference biomarker are normalized by dividing the expression level of the target biomarker to the expression levels of a plurality of endogenous reference biomarkers. The normalized expression level of a target biomarker can be used to predict the occurrence or lack thereof of an ischemic event, and/or the cause of the ischemic event.

In some embodiments, the expression level of the ischemia-associated biomarker from a patient suspected of having or experiencing an ischemic and from a control patient are normalized with respect to the expression levels of a plurality of stably expressed endogenous. The expression levels of the normalized expression of the ischemia-associated biomarkers are compared to the expression levels of the normalized expression of the same ischemia-associated biomarker in a control patient. The determined fold change in expression=normalized expression of target biomarker in the ischemia patient/normalized expression of target biomarker in control patient. Overexpression or underexpression of the normalized ischemia-associated biomarker in the ischemia patient by at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the expression levels of the normalized ischemia-associated biomarker in a healthy control patient indicates that the ischemia patient has experienced or is at risk of experiencing an ischemic event.

In some embodiments, the control level of expression is a predetermined threshold level. The threshold level can correspond to the level of expression of the same ischemia-associated biomarker in an otherwise healthy individual or a population of otherwise healthy individuals, optionally normalized to the expression levels of a plurality of endogenous reference biomarkers. After expression levels and normalized expression levels of the ischemia-associated biomarkers are determined in a representative number of otherwise healthy individuals and individuals predisposed to experiencing ischemia, normal and ischemia-predisposed expression levels of the ischemia-associated biomarkers can be maintained in a database, allowing for determination of threshold expression levels indicative of the presence or absence of risk to experience an ischemic event or the occurrence of ischemia. If the predetermined threshold level of expression is with respect to a population of normal control patients, then overexpression or underexpression of the ischemia-associated biomarker (usually normalized) in the ischemia patient by at least about 1.2-fold, 1.3-fold, 1.4-fold, 1.5-fold, 1.6-fold, 1.7-fold, 1.8-fold, 1.9-fold, 2.0-fold, 2.1 fold, 2.2-fold, 2.3-fold, 2.4-fold, 2.5-fold, 2.6-fold, 2.7-fold, 2.8-fold, 2.9-fold, 3.0-fold, 3.1-fold, 3.2-fold, 3.3-fold, 3.4-fold or 3.5-fold, or more, in comparison to the threshold level indicates that the ischemia patient has experienced or is at risk of experiencing ischemia. If the predetermined threshold level of expression is with respect to a population of patients known to have experienced an ischemic event or known to be at risk for experiencing ischemia, then an expression level in the patient suspected of experiencing ischemia that is approximately equal to the threshold level (or overexpressed or underexpressed greater than the threshold level of expression), indicates that the ischemia patient has experienced or is at risk of experiencing an ischemic event.

With respect to the endogenous reference biomarkers used for comparison, preferably, the endogenous reference biomarkers are stably expressed in blood. Exemplary endogenous reference biomarkers that find use are listed in Table 10, below. Further suitable endogenous reference biomarkers are published, e.g., in Stamova, et al., *BMC Medical Genomics* (2009) 2:49. In some embodiments, the expression levels of a plurality of endogenous reference biomarkers are determined as a control. In some embodiments, the expression levels of at least about 2, 3, 4, 5, 6, 7, 8, 9, 10, 15, 20, 25, 30, 35, or more, endogenous reference biomarkers, e.g., as listed in Table 10 or known in the art, are determined as a control.

In some embodiments, the expression levels of the endogenous reference biomarkers GAPDH, ACTB, B2M, HMBS and PPM are determined as a control. In some embodiments, the expression levels of 2, 3, 4, 5, 6, 7, 8, 9, 10, 15, 20, 25, or more, endogenous reference biomarkers selected from the group consisting of USP7, MAPRE2, CSNK1G2, SAFB2, PRKAR2A, PI4 KB, CRTC1, HADHA, MAP1LC3B, KAT5, CDC2L1///CDC2L2, GTSE1, CDC2L1///CDC2L2, TCF25, CHP, LRRC40, hCG_2003956///LYPLA2///LYPLA2P1, DAXX, UBE2NL, EIF1, KCMF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445///LOC115110, PEX16 are determined as a control.

TABLE 10

38 endogenous reference biomarkers stably expressed in blood for use in normalization and as control levels.
Table 10 - Stably Expressed Endogenous Reference Biomarkers

| Probe Set ID | Gene Symbol | Gene Title | GenBank ID | UniGene ID | RefSeq Transcript ID | RefSeq Protein ID |
|---|---|---|---|---|---|---|
| 201499_s_at | USP7 | ubiquitin specific peptidase 7 (herpes virus-associated) | NM_003470.1 | Hs.706830 | NM_003470 | NP_003461 |
| 202501_at | MAPRE2 | microtubule-associated protein, RP/EB family, member 2 | NM_014268.1 | Hs.532824 | NM_001143826 /// NM_001143827 /// NM_014268 /// NR_026570 | NP_001137298 /// NP_001137299 /// NP_055083 |
| 202573_at | CSNK1G2 | casein kinase 1, gamma 2 | AL530441 | Hs.651905 | NM_001319 | NP_001310 |
| 203280_at | SAFB2 | scaffold attachment factor B2 | NM_014649.1 | Hs.655392 | NM_014649 | NP_055464 |
| 204842_x_at | PRKAR2A | protein kinase, cAMP-dependent, regulatory, type II, alpha | BC002763.1 | Hs.631923 | NM_004157 | NP_004148 |

TABLE 10-continued 38 endogenous reference biomarkers stably expressed in blood for use in normalization and as control levels.
Table 10 - Stably Expressed Endogenous Reference Biomarkers

| Probe Set ID | Gene Symbol | Gene Title | GenBank ID | UniGene ID | RefSeq Transcript ID | RefSeq Protein ID |
|---|---|---|---|---|---|---|
| 206138_s_at | PI4KB | phosphatidylinositol 4-kinase, catalytic, beta | NM_002651.1 | Hs.632465 | NM_002651 | NP_002642 |
| 207159_x_at | CRTC1 | CREB regulated transcription coactivator 1 | NM_025021.1 | Hs.371096 | NM_001098482 /// NM_015321 | NP_001091952 /// NP_056136 |
| 208630_at | HADHA | hydroxyacyl-Coenzyme A dehydrogenase/3-ketoacyl-Coenzyme A thiolase/enoyl-Coenzyme A hydratase (trifunctional protein), alpha subunit | AI972144 | Hs.516032 | NM_000182 | NP_000173 |
| 208786_s_at | MAP1LC3B | microtubule-associated protein 1 light chain 3 beta | AF183417.1 | Hs.356061 | NM_022818 | NP_073729 |
| 209192_x_at | KAT5 | K(lysine) acetyltransferase 5 | BC000166.2 | Hs.397010 | NM_006388 /// NM_182709 /// NM_182710 | NP_006379 /// NP_874368 /// NP_874369 |
| 210474_s_at | CDC2L1 /// CDC2L2 | cell division cycle 2-like 1 (PITSLRE proteins) /// cell division cycle 2-like 2 (PITSLRE proteins) | U04819.1 | Hs.651228 | NM_024011 /// NM_033486 /// NM_033487 /// NM_033488 /// NM_033489 /// NM_033492 /// NM_033493 /// NM_033529 | NP_076916 /// NP_277021 /// NP_277022 /// NP_277023 /// NP_277024 /// NP_277027 /// NP_277028 /// NP_277071 |
| 211040_x_at | GTSE1 | G-2 and S-phase expressed 1 | BC006325.1 | Hs.386189 | NM_016426 | NP_057510 |
| 211289_x_at | CDC2L1 /// CDC2L2 | cell division cycle 2-like 1 (PITSLRE proteins) /// cell division cycle 2-like 2 (PITSLRE proteins) | AF067524.1 | Hs.651228 | NM_024011 /// NM_033486 /// NM_033487 /// NM_033488 /// NM_033489 /// NM_033492 /// NM_033493 /// NM_033529 | NP_076916 /// NP_277021 /// NP_277022 /// NP_277023 /// NP_277024 /// NP_277027 /// NP_277028 /// NP_277071 |
| 213311_s_at | TCF25 | transcription factor 25 (basic helix-loop-helix) | BF000251 | Hs.415342 | NM_014972 | NP_055787 |
| 214665_s_at | CHP | calcium binding protein P22 | AK000095.1 | Hs.406234 | NM_007236 | NP_009167 |
| 215063_x_at | LRRC40 | leucine rich repeat containing 40 | AL390149.1 | Hs.147836 | NM_017768 | NP_060238 |
| 215200_x_at | — | — | AK022362.1 | Hs.663419 | — | — |
| 215568_x_at | hCG_2003956 /// LYPLA2 /// LYPLA2P1 | hCG2003956 /// lysophospholipase II /// lysophospholipase II pseudogene 1 | AL031295 | Hs.533479 | NM_007260 /// NR_001444 | NP_009191 |
| 216038_x_at | DAXX | death-domain associated protein | BE965715 | Hs.336916 | NM_001141969 /// NM_001141970 /// NM_001350 /// NR_024517 | NP_001135441 /// NP_001135442 /// NP_001341 |
| 217393_x_at | UBE2NL | ubiquitin-conjugating enzyme E2N-like | AL109622 | Hs.585177 | NM_001012989 | NP_001013007 |
| 217549_at | — | — | AW574933 | Hs.527860 | — | — |
| 217672_x_at | EIF1 | eukaryotic translation initiation factor 1 | BF114906 | Hs.150580 | NM_005801 | NP_005792 |
| 217938_s_at | KCMF1 | potassium channel modulatory factor 1 | NM_020122.1 | Hs.654968 | NM_020122 | NP_064507 |
| 218378_s_at | PRKRIP1 | PRKR interacting protein 1 (IL11 inducible) | NM_024653.1 | Hs.406395 | NM_024653 | NP_078929 |
| 218571_s_at | CHMP4A | chromatin modifying protein 4A | NM_014169.1 | Hs.279761 | NM_014169 | NP_054888 |
| 219074_at | TMEM184C | transmembrane protein 184C | NM_018241.1 | Hs.203896 | NM_018241 | NP_060711 |
| 220052_s_at | TINF2 | TERF1 (TRF1)-interacting nuclear factor 2 | NM_012461.1 | Hs.496191 | NM_001099274 /// NM_012461 | NP_001092744 /// NP_036593 |
| 220411_x_at | PODNL1 | podocan-like 1 | NM_024825.1 | Hs.448497 | NM_001146254 /// NM_001146255 /// NM_024825 | NP_001139726 /// NP_001139727 /// NP_079101 |
| 221813_at | FBXO42 | F-box protein 42 | AI129395 | Hs.522384 | NM_018994 | NP_061867 |
| 222207_x_at | LOC441258 | Williams Beuren syndrome chromosome region 19 pseudogene | AK024602.1 | Hs.711232 | — | — |
| 222733_x_at | RRP1 | ribosomal RNA processing 1 homolog (S. cerevisiae) | BC000380.1 | Hs.110757 | NM_003683 | NP_003674 |

TABLE 10-continued 38 endogenous reference biomarkers stably expressed in blood for use in
normalization and as control levels.
Table 10 - Stably Expressed Endogenous Reference Biomarkers

| Probe Set ID | Gene Symbol | Gene Title | GenBank ID | UniGene ID | RefSeq Transcript ID | RefSeq Protein ID |
|---|---|---|---|---|---|---|
| 224667_x_at | C10orf104 | chromosome 10 open reading frame 104 | AK023981.1 | Hs.426296 | NM_173473 | NP_775744 |
| 224858_at | ZDHHC5 | zinc finger, DHHC-type containing 5 | AK023130.1 | Hs.27239 | NM_015457 | NP_056272 |
| 225403_at | C9orf23 | chromosome 9 open reading frame 23 | AL528391 | Hs.15961 | NM_148178 /// NM_148179 | NP_680544 /// NP_680545 |
| 226253_at | LRRC45 | leucine rich repeat containing 45 | BE965418 | Hs.143774 | NM_144999 | NP_659436 |
| 227651_at | NACC1 | nucleus accumbens associated 1, BEN and BTB (POZ) domain containing | AI498126 | Hs.531614 | NM_052876 | NP_443108 |
| 232190_x_at | LOC100133445 /// LOC115110 | hypothetical LOC100133445 /// hypothetical protein LOC115110 | AI393958 | Hs.132272 | NR_026927 /// XR_036887 /// XR_038144 | — |
| 49878_at | PEX16 | peroxisomal biogenesis factor 16 | AA523441 | Hs.100915 | NM_004813 /// NM_057174 | NP_004804 /// NP_476515 |

5. Methods of Detecting Biomarkers Associated with Ischemia

Gene expression may be measured using any method known in the art. One of skill in the art will appreciate that the means of measuring gene expression is not a critical aspect of the invention. The expression levels of the biomarkers can be detected at the transcriptional or translational (i.e., protein) level.

In some embodiments, the expression levels of the biomarkers are detected at the transcriptional level. A variety of methods of specific DNA and RNA measurement using nucleic acid hybridization techniques are known to those of skill in the art (see, Sambrook, supra and Ausubel, supra) and may be used to detect the expression of the genes set forth in Tables 3 and 4. Some methods involve an electrophoretic separation (e.g., Southern blot for detecting DNA, and Northern blot for detecting RNA), but measurement of DNA and RNA can also be carried out in the absence of electrophoretic separation (e.g., by dot blot). Southern blot of genomic DNA (e.g., from a human) can be used for screening for restriction fragment length polymorphism (RFLP) to detect the presence of a genetic disorder affecting a polypeptide of the invention. All forms of RNA can be detected, including, e.g., message RNA (mRNA), microRNA (miRNA), ribosomal RNA (rRNA) and transfer RNA (tRNA).

The selection of a nucleic acid hybridization format is not critical. A variety of nucleic acid hybridization formats are known to those skilled in the art. For example, common formats include sandwich assays and competition or displacement assays. Hybridization techniques are generally described in Hames and Higgins Nucleic Acid Hybridization, A Practical Approach, IRL Press (1985); Gall and Pardue, Proc. Natl. Acad. Sci. U.S.A., 63:378-383 (1969); and John et al. Nature, 223:582-587 (1969).

Detection of a hybridization complex may require the binding of a signal-generating complex to a duplex of target and probe polynucleotides or nucleic acids. Typically, such binding occurs through ligand and anti-ligand interactions as between a ligand-conjugated probe and an anti-ligand conjugated with a signal. The binding of the signal generation complex is also readily amenable to accelerations by exposure to ultrasonic energy.

The label may also allow indirect detection of the hybridization complex. For example, where the label is a hapten or antigen, the sample can be detected by using antibodies. In these systems, a signal is generated by attaching fluorescent or enzyme molecules to the antibodies or in some cases, by attachment to a radioactive label (see, e.g., Tijssen, "Practice and Theory of Enzyme Immunoassays," Laboratory Techniques in Biochemistry and Molecular Biology, Burdon and van Knippenberg Eds., Elsevier (1985), pp. 9-20).

The probes can be labeled either directly, e.g., with isotopes, chromophores, lumiphores, chromogens, or indirectly, such as with biotin, to which a streptavidin complex may later bind. Thus, the detectable labels used in the assays of the present invention can be primary labels (where the label comprises an element that is detected directly or that produces a directly detectable element) or secondary labels (where the detected label binds to a primary label, e.g., as is common in immunological labeling). Typically, labeled signal nucleic acids are used to detect hybridization. Complementary nucleic acids or signal nucleic acids may be labeled by any one of several methods typically used to detect the presence of hybridized polynucleotides. The most common method of detection is the use OF AUTORADIOGRAPHY WITH $^{3}$H, $^{125}$I, $^{35}$S, $^{14}$C, or $^{32}$P-LABELED PROBES OR THE LIKE.

Other labels include, e.g., ligands that bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden Introduction to Immunocytochemistry, 2nd ed., Springer Verlag, N.Y. (1997); and in Haugland Handbook of Fluorescent Probes and Research Chemicals, a combined handbook and catalogue Published by Molecular Probes, Inc. (1996).

In general, a detector which monitors a particular probe or probe combination is used to detect the detection reagent label. Typical detectors include spectrophotometers, phototubes and photodiodes, microscopes, scintillation counters, cameras, film and the like, as well as combinations thereof. Examples of suitable detectors are widely available from a variety of commercial sources known to persons of skill in the art. Commonly, an optical image of a substrate comprising bound labeling moieties is digitized for subsequent computer analysis.

Most typically, the amount of RNA is measured by quantifying the amount of label fixed to the solid support by binding of the detection reagent. Typically, the presence of a modulator during incubation will increase or decrease the amount of label fixed to the solid support relative to a control incubation which does not comprise the modulator, or as compared to a baseline established for a particular reaction type. Means of detecting and quantifying labels are well known to those of skill in the art.

In preferred embodiments, the target nucleic acid or the probe is immobilized on a solid support. Solid supports suitable for use in the assays of the invention are known to those of skill in the art. As used herein, a solid support is a matrix of material in a substantially fixed arrangement.

For example, in one embodiment of the invention, microarrays are used to detect the pattern of gene expression. Microarrays provide one method for the simultaneous measurement of the expression levels of large numbers of genes. Each array has a reproducible pattern of a plurality of nucleic acids (e.g., a plurality of nucleic acids that hybridize to a plurality of the genes set forth in Tables 3 and/or 5) attached to a solid support. In one embodiment, the array contains a plurality of nucleic acids that hybridize to a plurality of the genes listed in Table 3. In one embodiment, the array contains a plurality of nucleic acids that hybridize to a plurality of the genes listed in Table 5. In one embodiment, the array further contains a plurality of nucleic acids that hybridize to a plurality of genes useful for diagnosing ischemic stroke, cardioembolic stroke, carotid stenosis, atrial fibrillation, transient ischemic attacks and/or lacunar stroke, as described herein and/or known in the art. In various embodiments, the array further contains a plurality of stably expressed endogenous reference biomarkers. Labeled RNA or DNA is hybridized to complementary probes on the array and then detected by laser scanning. Hybridization intensities for each probe on the array are determined and converted to a quantitative read-out of relative gene expression levels in ischemia (e.g., correlative with or associative of ischemia, or allowing the differentiation of a transient neurological event as ischemic or non-ischemic).

In some embodiments, a sample is obtained from a subject, total mRNA is isolated from the sample and is converted to labeled cRNA and then hybridized to an array. Relative transcript levels are calculated by reference to appropriate controls present on the array and in the sample. See Mahadevappa and Warrington, Nat. Biotechnol. 17, 1134-1136 (1999).

A variety of automated solid-phase assay techniques are also appropriate. For instance, very large scale immobilized polymer arrays (VLSIPS™), available from Affymetrix, Inc. (Santa Clara, Calif.) can be used to detect changes in expression levels of a plurality of genes involved in the same regulatory pathways simultaneously. See, Tijssen, supra., Fodor et al. (1991) Science, 251: 767-777; Sheldon et al. (1993) Clinical Chemistry 39(4): 718-719, and Kozal et al. (1996) Nature Medicine 2(7): 753-759. Integrated microfluidic systems and other point-of-care diagnostic devices available in the art also find use. See, e.g., Liu and Mathies, Trends Biotechnol. (2009) 27(10):572-81 and Tothill, Semin Cell Dev Biol (2009) 20(1):55-62. Microfluidics systems for use in detecting levels of expression of a plurality of nucleic acids are available, e.g., from NanoString Technologies, on the internet at nanostring.com.

Detection can be accomplished, for example, by using a labeled detection moiety that binds specifically to duplex nucleic acids (e.g., an antibody that is specific for RNA-DNA duplexes). One preferred example uses an antibody that recognizes DNA-RNA heteroduplexes in which the antibody is linked to an enzyme (typically by recombinant or covalent chemical bonding). The antibody is detected when the enzyme reacts with its substrate, producing a detectable product. Coutlee et al. (1989) Analytical Biochemistry 181: 153-162; Bogulayski (1986) et al. J. Immunol. Methods 89:123-130; Prooijen-Knegt (1982) Exp. Cell Res. 141:397-407; Rudkin (1976) Nature 265:472-473, Stollar (1970) Proc. Nat'l Acad. Sci. USA 65:993-1000; Ballard (1982) Mol. Immunol. 19:793-799; Pisetsky and Caster (1982) Mol. Immunol. 19:645-650; Viscidi et al. (1988) J. Clin. Microbial. 41:199-209; and Kiney et al. (1989) J. Clin. Microbiol. 27:6-12 describe antibodies to RNA duplexes, including homo and heteroduplexes. Kits comprising antibodies specific for DNA:RNA hybrids are available, e.g., from Digene Diagnostics, Inc. (Beltsville, Md.).

In addition to available antibodies, one of skill in the art can easily make antibodies specific for nucleic acid duplexes using existing techniques, or modify those antibodies that are commercially or publicly available. In addition to the art referenced above, general methods for producing polyclonal and monoclonal antibodies are known to those of skill in the art (see, e.g., Paul (3rd ed.) Fundamental Immunology Raven Press, Ltd., NY (1993); Coligan, et al., Current Protocols in Immunology, Wiley Interscience (1991-2008); Harlow and Lane, Antibodies: A Laboratory Manual Cold Spring Harbor Press, NY (1988); Harlow and Lane, Using Antibodies, Cold Spring Harbor Press, NY (1999); Stites et al. (eds.) Basic and Clinical Immunology (4th ed.) Lange Medical Publications, Los Altos, Calif., and references cited therein; Goding Monoclonal Antibodies: Principles and Practice (2d ed.) Academic Press, New York, N.Y., (1986); and Kohler and Milstein Nature 256: 495-497 (1975)). Other suitable techniques for antibody preparation include selection of libraries of recombinant antibodies in phage or similar vectors (see, Huse et al. Science 246:1275-1281 (1989); and Ward et al. Nature 341:544-546 (1989)). Specific monoclonal and polyclonal antibodies and antisera will usually bind with a dissociation constant ($K_D$) of at least about 0.1 µM, preferably at least about 0.01 µM or better, and most typically and preferably, 0.001 µM or better.

The nucleic acids used in this invention can be either positive or negative probes. Positive probes bind to their targets and the presence of duplex formation is evidence of the presence of the target. Negative probes fail to bind to the suspect target and the absence of duplex formation is evidence of the presence of the target. For example, the use of a wild type specific nucleic acid probe or PCR primers may serve as a negative probe in an assay sample where only the nucleotide sequence of interest is present.

The sensitivity of the hybridization assays may be enhanced through use of a nucleic acid amplification system that multiplies the target nucleic acid being detected. Examples of such systems include the polymerase chain reaction (PCR) system, in particular RT-PCR or real time PCR, and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. High throughput multiplex nucleic acid sequencing or "deep sequencing" to detect captured expressed biomarker genes also finds use. High throughput sequencing techniques are known in the art (e.g., 454 Sequencing on the internet at 454.com).

An alternative means for determining the level of expression of the nucleic acids of the present invention is in situ hybridization. In situ hybridization assays are well known and are generally described in Angerer et al., Methods Enzymol. 152:649-660 (1987). In an in situ hybridization assay, cells, preferentially human cells, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters.

In other embodiments, quantitative RT-PCR is used to detect the expression of a plurality of the genes set forth in Tables 3 and/or 5. In one embodiment, quantitative RT-PCR is used to detect a plurality of the genes listed in Table 3. In one embodiment, quantitative RT-PCR is used to detect a plurality of the genes listed in Table 5. In one embodiment, quantitative RT-PCR is used to further detect a plurality of the genes useful for the diagnosis of ischemic stroke, cardioembolic stroke, carotid stenosis, atrial fibrillation and/or transient ischemic attacks, as described herein and known in the art. A general overview of the applicable technology can be found, for example, in A-Z of Quantitative PCR, Bustin, ed., 2004, International University Line; Quantitative PCR Protocols, Kochanowski and Reischl, eds., 1999, Humana Press; Clinical Applications of PCR, Lo, ed., 2006, Humana Press; PCR Protocols: A Guide to Methods and Applications (Innis et al. eds. (1990)) and PCR Technology: Principles and Applications for DNA Amplification (Erlich, ed. (1992)). In addition, amplification technology is described in U.S. Pat. Nos. 4,683,195 and 4,683,202. Methods for multiplex PCR, known in the art, are applicable to the present invention.

Accordingly, in one embodiment of the invention provides a reaction mixture comprising a plurality of polynucleotides which specifically hybridize (e.g., primers) to a plurality of nucleic acid sequences of the genes set forth in Tables 3 and/or 5. In some embodiments, the invention provides a reaction mixture comprising a plurality of polynucleotides which specifically hybridize (e.g., primers) to a plurality of nucleic acid sequences of the genes set forth in Table 3. In some embodiments, the invention provides a reaction mixture comprising a plurality of polynucleotides which specifically hybridize (e.g., primers) to a plurality of nucleic acid sequences of the genes set forth in Table 5. In some embodiments, the invention provides a reaction mixture further comprising a plurality of polynucleotides which specifically hybridize (e.g., primers) to a plurality of nucleic acid sequences of the genes useful for the diagnosis of ischemic stroke, cardioembolic stroke, carotid stenosis, atrial fibrillation and/or transient ischemic attacks, as described herein and known in the art. In some embodiments, the reaction mixture is a PCR mixture, for example, a multiplex PCR mixture.

This invention relies on routine techniques in the field of recombinant genetics. Generally, the nomenclature and the laboratory procedures in recombinant DNA technology described below are those well-known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. Basic texts disclosing the general methods of use in this invention include Sambrook et al., Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994-2008, Wiley Interscience)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, Tetrahedron Letts. 22:1859-1862 (1981), using an automated synthesizer, as described in Van Devanter et. al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

In some embodiments, the expression level of the biomarkers described herein are detected at the translational or protein level. Detection of proteins is well known in the art, and methods for protein detection known in the art find use. Exemplary assays for determining the expression levels of a plurality of proteins include, e.g., ELISA, flow cytometry, mass spectrometry (e.g., MALDI or SELDI), surface plasmon resonance (e.g., BiaCore), microfluidics and other biosensor technologies. See, e.g., Tothill, Semin Cell Dev Biol (2009) 20(1):55-62.

6. Ischemia Reference Profiles

The invention also provides ischemia reference profiles. The ischemia reference profiles comprise information correlating the expression levels of a plurality of ischemia-associated genes (i.e., a plurality of the genes set forth in Tables 3 and/or 5) to the occurrence or risk of experiencing an ischemic event. The profiles can conveniently be used to diagnose, monitor and prognose ischemia.

One embodiment of the invention provides an ischemia gene expression reference profile for subjects who have experienced or are at risk for experiencing an ischemic event (e.g., cerebral ischemia, myocardial ischemia, pulmonary ischemia, transient cerebral ischemia). Accordingly, the ischemia profile correlates the expression levels of a plurality of the genes selected from Tables 3 and/or 5. For example, an expression profile exhibiting an increase in expression of a plurality of the following genes: UBE2J1, ELAVL3, FCGR2B, BLVRA, JMJD6, DDAH2, PTRH2, CARD16, CAV1, ZNF608, NDUFB3, 5LC22A4, PCMT1, CACNA1A, CASP1 and LOC100129105, when compared to the control level, and/or a decrease in expression of a plurality of the following genes: AK5, DIP2A, ETS1, CCND3, GNE, BCL9L, SPATA5, and LBH when compared to the control level is a reference profile for a subject who has experienced or is at risk for experiencing an ischemic event. An expression profile exhibiting an increase in expression of a plurality of the following genes: UBE2J1, CARD16, LOC203274, ZNF608, CARD16///CASP1, UBE2J1, PTRH2, ANXA3, FCGR2B, C14orf101, LOC100129105, DDAH2, RAB27A, AIM2, CASP5, HNRNPH2, RAB27A, SHOX2, CNIH4, TLR10, ZEB2, NDUFB3, CYTH4, BLVRA, FLJ39051, SLC22A4, DNAH17, SPATA4, CACNA1A, CASP1, PGS1, LTBR, FCGR1B, IGFBP5, LTB, N4BP2L2, DRAM1, WIT1, ELAVL3, FKBP15, JMJD6, CAV1 and PCMT1, when compared to the control level, and/or a decrease in expression of a plurality of the following genes: FOXK1, AK5, APBA2, NUCKS1, NEIL2, WHAMML1///WHAMML2, GLG1, CCND3, LBH, TAF3, TBC1D10A, FMNL3, SPATA5, ZMYND11, CAPN5, GNE, MMP19, ZNF609, ETS1, BCL9L, DIP2A, APBB1, NPTXR when compared to the control level is a reference profile for a subject who has experienced or is at risk for experiencing an ischemic event. In some embodiments, an expression profile exhibiting an increase in expression of a plurality of the following genes: AIM2, C14orf101, DNAH17, UBE2J1, LOC203274, PGS1, ZEB2, DDAH2, CARD16, SPATA4, ANXA3, WIT1, FCGR2B, CACNA1A, FKBP15, N4BP2L2, HNRNPH2, ELAVL3, ZNF608, TLR10, BLVRA, SLC22A4, RAB27A, LTBR, CARD16///CASP1, IGFBP5, CASP5, LTB, NDUFB3, SHOX2, CAV1, CNIH4, FLJ39051, CASP1, PTRH2, LOC100129105, PCMT1, CYTH4, JMJD6, DRAM1, FCGR1B, when compared to the control level, and/or a decrease in expression of a plurality of the following genes: NEIL2, FOXK1, NUCKS1, MMP19, APBA2, SPATA5, BCL9L, GLG1, CCND3, TBC1D10A, AK5, ZNF609, ETS1, WHAMML1///WHAMML2, GNE, NPTXR, DIP2A, LBH, APBB1, ZMYND11, CAPN5, TAF3 and FMNL3 when compared to the control level is a reference profile for a subject who has experienced or is at risk for experiencing an ischemic event. In some embodiments, an expression profile exhibiting an increase in expression of a plurality of the following genes: CARD16, IRF7, TLR6, NMU, C13orf16, TAPBP, BTC, ZBP1, HSPA6, TWIST1, PLSCR1, SAMD9L, OSTCL, C9orf66, GYPA, ADM, ANKRD22, SHOX, ZNF354A, SRGAP1, GRM5, BAGE, XRCC4, SLC37A3, OVOL2, LIFR, RASAL2, hCG_1749898, IQGAP3, HS3ST3A1, NPR3, SIX3 and HCN1, when compared to the control level, and/or a decrease in expression of a plurality of the following genes: CAND1, GUSBL2, SLC3A1, ALDH6A1, CLTC, FUS, RANBP10, KIAA0391, MED1, NAPEPLD, KIAA1919, HCFC1, TPP2, G3BP1, PRDX6, YARS, PYGB, YBX1///YBX1P2, FUS///NR1H3, GCAT, CAPN5, LOC100129656, SMARCC2, HELLS, MAP2K7, ZNF652, GSTM1, C16orf35, KIAA1659, GSTM2, LOC440104, VTI1A, HERC1, ALS2CL, GSTM1, GCAT, ERMN, LOC100293532, IFT80, RBM6, BAZ1B, HNRNPUL2, ENTPD5, ATXN2L, LPIN1, METTL3, MBNL2, SMURF2, C20orf196, UNC84A, DCAF16 and EIF3B when compared to the control level is a reference profile for a subject who has experienced or is at risk for experiencing an ischemic event.

Conversely, an expression profile exhibiting a decrease in expression of a plurality of the following genes: UBE2J1, ELAVL3, FCGR2B, BLVRA, JMJD6, DDAH2, PTRH2, CARD16, CAV1, ZNF608, NDUFB3, SLC22A4, PCMT1, CACNA1A, CASP1 and LOC100129105, when compared to the control level, and/or an increase in expression of a plurality of the following genes: AK5, DIP2A, ETS1, CCND3, GNE, BCL9L, SPATA5, and LBH when compared to the control level is a reference profile for a subject who has not experienced or is not at risk for experiencing an ischemic event. An expression profile exhibiting a decrease in expression of a plurality of the following genes: UBE2J1, CARD16, LOC203274, ZNF608, CARD16///CASP1, UBE2J1, PTRH2, ANXA3, FCGR2B, C14orf101, LOC100129105, DDAH2, RAB27A, AIM2, CASP5, HNRNPH2, RAB27A, SHOX2, CNIH4, TLR10, ZEB2, NDUFB3, CYTH4, BLVRA, FLJ39051, SLC22A4, DNAH17, SPATA4, CACNA1A, CASP1, PGS1, LTBR, FCGR1B, IGFBP5, LTB, N4BP2L2, DRAM1, WIT1, ELAVL3, FKBP15, JMJD6, CAV1 and PCMT1, when compared to the control level, and/or an increase in expression of a plurality of the following genes: FOXK1, AK5, APBA2, NUCKS1, NEIL2, WHAMML1///WHAMML2, GLG1, CCND3, LBH, TAF3, TBC1D10A, FMNL3, SPATA5, ZMYND11, CAPN5, GNE, MMP19, ZNF609, ETS1, BCL9L, DIP2A, APBB1, NPTXR when compared to the control level is a reference profile for a subject who has not experienced or is not at risk for experiencing an ischemic event. In some embodiments, an expression profile exhibiting a decrease in expression of a plurality of the following genes: AIM2, C14orf101, DNAH17, UBE2J1, LOC203274, PGS1, ZEB2, DDAH2, CARD16, SPATA4, ANXA3, WIT1, FCGR2B, CACNA1A, FKBP15, N4BP2L2, HNRNPH2, ELAVL3, ZNF608, TLR10, BLVRA, SLC22A4, RAB27A, LTBR, CARD16///CASP1, IGFBP5, CASP5, LTB, NDUFB3, SHOX2, CAV1, CNIH4, FLJ39051, CASP1, PTRH2, LOC100129105, PCMT1, CYTH4, JMJD6, DRAM1, FCGR1B, when compared to the control level, and/or an increase in expression of a plurality of the following genes: NEIL2, FOXK1, NUCKS1, MMP19, APBA2, SPATA5, BCL9L, GLG1, CCND3, TBC1D10A, AK5, ZNF609, ETS1, WHAMML1///WHAMML2, GNE, NPTXR, DIP2A, LBH, APBB1, ZMYND11, CAPN5, TAF3 and FMNL3 when compared to the control level is a reference profile for a subject who has not experienced or is not at risk for experiencing an ischemic event. In some embodiments, an expression profile exhibiting a decrease in expression of a plurality of the following genes: CARD16, IRF7, TLR6, NMU, C13orf16, TAPBP, BTC, ZBP1, HSPA6, TWIST1, PLSCR1, SAMD9L, OSTCL, C9orf66, GYPA, ADM, ANKRD22, SHOX, ZNF354A, SRGAP1, GRM5, BAGE, XRCC4, SLC37A3, OVOL2, LIFR, RASAL2, hCG_1749898, IQGAP3, HS3ST3A1, NPR3, SIX3 and HCN1, when compared to the control level, and/or an increase in expression of a plurality of the following genes: CAND1, GUSBL2, SLC3A1, ALDH6A1, CLTC, FUS, RANBP10, KIAA0391, MED1, NAPEPLD, KIAA1919, HCFC1, TPP2, G3BP1, PRDX6, YARS, PYGB, YBX1///YBX1P2, FUS///NR1H3, GCAT, CAPN5, LOC100129656, SMARCC2, HELLS, MAP2K7, ZNF652, GSTM1, C16orf35, KIAA1659, GSTM2, LOC440104, VTI1A, HERC1, ALS2CL, GSTM1, GCAT, ERMN, LOC100293532, IFT80, RBM6, BAZ1B, HNRNPUL2, ENTPD5, ATXN2L, LPIN1, METTL3, MBNL2, SMURF2, C20orf196, UNC84A, DCAF16 and EIF3B when compared to the control level is a reference profile for a subject who has not experienced or is not at risk for experiencing an ischemic event.

One embodiment of the invention further provides an ischemia reference profile for subjects who have experienced or are at risk for experiencing stroke, regardless of cause. Accordingly, the ischemia reference profile correlates the expression levels of a plurality of ischemic stroke-associated genes. For example, an expression profile exhibiting an increase in expression of a plurality of the following genes: PGM5, CCDC144C///LOC100134159, LECT2, SHOX, TBX5, SNIP, RBMS3, P704P, THSD4, FAT3, SNRPN, GLYATL1, GADL1, CXADR, OVOL2, RNF141, CLEC4E, BXDC5, UNC5B, TIMP2, ASTN2, FLJ35934, ANKRD28, CCDC144A, TIMM8A, ALDOAP2, LDB3, PTPRD, LOC729222///PPFIBP1, CCRL1, FCRL4, ELAVL2, PRTG, DLX6, SCD5, GABRB2, GYPA, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA, LOC283027, LOC344595, RPL22, LOC100129488 and MCTP1 when compared to the control level, and/or a decrease in expression of a plurality of the following genes: SPTLC3, DKRZP434L187, SPIB, HNRNPUL2, FOXA2, RPL22 and SH3GL3 when compared to the control level is a reference profile for a subject who has experienced or is at risk for stroke.

One embodiment of the invention further provides an ischemia reference profile for subjects who have experienced or are at risk for experiencing cardioembolic stroke. Accordingly, the ischemia reference profile correlates the expression levels of a plurality of the genes correlative for or associated with cardioembolic stroke. For example, an expression profile exhibiting an increase in expression of a plurality of the following genes: IRF6, ZNF254, GRM5, EXT2, AP3S2, PIK3C2B, ARHGEF5, COL13A1, PTPN20A///PTPN20B, LHFP, BANK1, HLA-DOA, EBF1, TMEM19, LHFP, FCRL1, OOEP and LRRC37A3 when compared to the control level, and/or a decrease in expression of a plurality of the following genes: LOC284751, CD46, ENPP2, C19orf28, TSKS, CHURC1, ADAMTSL4, FLJ40125, CLEC18A, ARHGEF12, C16orf68, TFDP1 and GSTK1 when compared to the control level is a reference profile for a subject who has experienced or is at risk for a cardioembolic stroke.

One embodiment of the invention further provides an ischemia reference profile for subjects who have experienced or are at risk for experiencing carotid stenosis and atherosclerotic stroke. Accordingly, the ischemia reference profile correlates the expression levels of a plurality of the genes correlative for or associated with carotid stenosis and atherosclerotic stroke. For example, an expression profile exhibiting an increase in expression of a plurality of the following genes: NT5E, CLASP2, GRM5, PROCR, ARHGEF5, AKR1C3, COL13A1, LHFP, RNF7, CYTH3, EBF1, RANBP10, PRSS35, C12orf42 and LOC100127980 when compared to the control level, and/or a decrease in expression of a plurality of the following genes: FLJ31945, LOC284751, LOC100271832, MTBP, ICAM4, SHOX2, DOPEY2, CMBL, LOC146880, SLC20A1, SLC6A19, ARHGEF12, C16orf68, GIPC2 when compared to the control level is a reference profile for a subject who has experienced or is at risk for carotid stenosis and atherothrombotic stroke.

One embodiment of the invention further provides an ischemia reference profile for subjects who have experienced or are at risk for experiencing atrial fibrillation. Accordingly, the ischemia reference profile correlates the expression levels of a plurality of the genes correlative for or associated with atrial fibrillation. For example, an expression profile exhibiting an increase in expression of a plurality of the following genes: SMC1A, SNORA68, GRLF1, SDC4, HIPK2, LOC100129034, CMTM1 and TTC7A when compared to the control level, and/or a decrease in expression of a plurality of the following genes: LRRC43, MIF/// SLC2A11, PER3, PPIE, COL13A1, DUSP16, LOC100129034, BRUNOL6, GPR176, C6orf164 and MAP3K7IP1 when compared to the control level is a reference profile for a subject who has experienced or is at risk for atrial fibrillation.

One embodiment of the invention further provides an ischemia reference profile for subjects who have experienced or are at risk for experiencing transient ischemic attacks. Accordingly, the ischemia reference profile correlates the expression levels of a plurality of the genes correlative for or associated with transient ischemic attacks. For example, an expression profile exhibiting an increase in expression of a plurality of the following genes: GABRB2, ELAVL3, COL1A1, SHOX2, GABRB2, TWIST1, DPPA4, DKFZP434P211, WIT1, SOX9, DLX6, ANXA3, EPHA3, SOX11, SLC26A8, CCRL1, FREM2, STOX2, ZNF479, LOC338862, ASTN2, FOLH1, SNX31, KREMEN1, ZNF479, ALS2CR11, FIGN, RORB, LOC732096, GYPA, ALPL, LHX2, GALNT5, SRD5A2L2, GALNT14, OVOL2, BMPR1B, UNC5B, ODZ2, ALPL, RASAL2, SHOX, C19orf59, ZNFLJ4, SRGAP1, ELAVL2, NCRNA00032, LOC440345, FLJ30375, TFPI, PTGR1, ROBO1, NR2F2, GRM5, LUM, FLJ39051, COL1A2, CASP5, OPCML, TTC6, TFAP2B, CRISP2, SOX11, ANKRD30B, FLJ39051, SCN2A, MYNN, FOXA2, DKFZP434B061, LOC645323, SNIP, LOC645323, LOC374491, ADAM30, SIX3, FLJ36144, CARD8, KREMEN1, RP1-127L4.6, FAM149A, B3GAT2, SPOCK3, G30, ITGBL1, IQGAP3, C7orf45, ZNF608, LOC375010, LRP2, TGFB2, SHOX2, HOXC4/// HOXC6, ELTD1, FAM182B///RP13-401N8.2, PRO0478, LIFR, FOLH1, EHF, NDST3, BRUNOL5, LOC728460, PDE1A, POU2AF1, FAT1, PCDH11X///PCDH11Y, FLJ37786, SLC22A4, DHRS13, EHF, MEG3, PIWIL1, LOC203274, LOC100133920///LOC286297, DMRT1, ADM, VWA3B, GAFA3, HESX1, ADAMDEC1, CAV1, LAMB4, TPTE, PPP1R1C, HPSE, AIM2, RUNDC3B, CARD16, FAM124A, MGC39584, OSM, RFX2, MYBPC1, LTBR, C18orf2, SNRPN, FLJ36031, IL1B, TRPM1, OSTCL, MAPK14, KCNJ15///LOC100131955, FIGN, HNT, S100A12, CHIT1, C7orf53, FAM13A1, GNAO1, MAPK14, FAM55D, PRKD2, LIMK2, C18orf54, IGFBP5, EVI1, PLSCR1, FOXC1, LOC646627, ZNF462, CNTLN, ZNF438, DEFB105A///DEFB105B, LOC340017, C1orf67, ACSL1, ADH1B, SLC2A14///SLC2A3, IL1B, ST3GAL4, UBE2J1, PNPLA3 and PAPPA when compared to the control level, and/or a decrease in expression of a plurality of the following genes: NBPF10///RP11-94I2.2, SFXN1, SPIN3, UNC84A, OLFM2, PPM1K, P2RY10, ZNF512B, MORF4L2, GIGYF2, ERAP2, SLFN13, LOC401431, MED6, BAIAP2L1///LOC100128461, LNPEP, MBNL1, NOS3, MCF2L, KIAA1659, SCAMP5, LOC648921, ANAPC5, SPON1, FUS, GPR22, GAL3ST4, METTL3, LOC100131096, FAAH2, SMURF2, SNRPN, FBLN7, GLS, G3BP1, RCAN3, EPHX2, DIP2C, CCDC141, CLTC, FOSB, CACNA1I, UNQ6228, ATG9B, AK5, SPIN3, RBM14, SNRPN, MAN1C1, HELLS, EDAR, SLC3A1, ZNF519, LOC100130070///LOC100130775/// LOC100131787///LOC100131905///LOC100132291/// LOC100132488///RPS27, ZC3H12B, IQGAP2, SOX8, WHDC1L2, TNPO1, TNFRSF21, TSHZ2, DMRTC1/// DMRTC1B, GSTM1, GSTM2, PNMA6A, CAND1, CCND3, GSTM1, GUSBL2 when compared to the control level is a reference profile for a subject who has experienced or is at risk for transient ischemic attack.

One embodiment of the invention further provides a lacunar stroke gene expression reference profile for subjects who have experienced or are at risk for experiencing lacunar stroke. For example, an expression profile exhibiting an increase in expression of a plurality of the following genes: AKAP9, ALS2CR11, BNC2, BZRAP1, C18orf49, CALM1, CCDC114, CCDC78, CCL2, CCL3, CCL3L1, CCL3L3, CCL4, CHST2, CSF1, ERBB2, FAM179A, GBP4, GBR56, GRAMD3, GRHL2, GRK4, HLA-DRB4, ITIH4, KIAA1618, LAG3, LAIR2, LGR6, LOC100132181, LOC147646, LOC150622, LOC161527, OASL, PLEKHF1, PRKD2, PROCR, PRSS23, RASEF, RGNEF, RUNX3, SCAND2, SESN2, SLAMF7, SPON2, STAT1, SYNGR1, TRX21, TGFBR3, TMEM67, TSEN54, TTC12, TUBE1, UBA7, UTS2, and ZNF827, when compared to the control level, and/or a decrease in expression of a plurality of the following genes: AGFG1, BTG1, CFDP1, CHML, CNPY2, FAM105A, FAM70B, FLJ13773, GATM, GTF2H2, GTF2H2B, HLA-DQA1, IGHG1, IL18RAP, IL8, LOC254128, LRRC8B, MPZL3, N4BP2, PDXDC1, PHACTR1, QK1, RTKN2, SLC16A1, SOCS1, SPAG17, ST6GALNAC1, STK17B, STK4, STT3B, STX16, STX7, TBC1D12, TRIM4, UACA, UGCG, VAPA, and WHAMML2, when compared to the control level is a reference profile for a subject who has experienced or is at risk for lacunar stroke. In one embodiment, an expression profile exhibiting an increase in expression of a plurality of the following genes: HLA-DRB4, TTC12, GBP4, UBA7, CCDC78, C18orf49, RASEF, TSEN54, RUNX3, PROCR, TGFBR3, PRSS23, CALM1, FAM179A, CCDC114, LGR6, SCAND2, LAIR2, CCL3, CCL3L1, CCL3L3, LAG3, CCL2, OASL, UTS2, LOC100132181 and ALS2CR11, when compared to the control level, and/or a decrease in expression of a plurality of the following genes: STK4, LRRC8B, PDXDC1, LOC254128, IL8, GTF2H2, UGCG, MPZL3, VAPA, STX7, FAM70B, QKI, CHML, FLJ13773, HLA-DQA1, when compared to the control level is a reference profile for a subject who has experienced or is at risk for lacunar stroke.

The reference profiles can be entered into a database, e.g., a relational database comprising data fitted into predefined categories. Each table, or relation, contains one or more data categories in columns. Each row contains a unique instance of data for the categories defined by the columns. For example, a typical database for the invention would include a table that describes a sample with columns for age, gender, reproductive status, expression profile and so forth. Another table would describe a disease: symptoms, level, sample identification, expression profile and so forth. In one embodiment, the invention matches the experimental sample to a database of reference samples. The database is assembled with a plurality of different samples to be used as reference samples. An individual reference sample in one embodiment will be obtained from a patient during a visit to a medical professional. Information about the physiological, disease and/or pharmacological status of the sample will also be obtained through any method available. This may include, but is not limited to, expression profile analysis, clinical analysis, medical history and/or patient interview. For example, the patient could be interviewed to determine age, sex, ethnic origin, symptoms or past diagnosis of disease, and the identity of any therapies the patient is currently undergoing. A plurality of these reference samples will be taken. A single individual may contribute a single reference sample or more than one sample over time. One skilled in the art will recognize that confidence levels in predictions based on comparison to a database increase as the number of reference samples in the database increases.

The database is organized into groups of reference samples. Each reference sample contains information about physiological, pharmacological and/or disease status. In one aspect the database is a relational database with data organized in three data tables, one where the samples are grouped primarily by physiological status, one where the samples are grouped primarily by disease status and one where the samples are grouped primarily by pharmacological status. Within each table the samples can be further grouped according to the two remaining categories. For example the physiological status table could be further categorized according to disease and pharmacological status.

As will be appreciated by one of skill in the art, the present invention may be embodied as a method, data processing system or program products. Accordingly, the present invention may take the form of data analysis systems, methods, analysis software, etc. Software written according to the present invention is to be stored in some form of computer readable medium, such as memory, hard-drive, DVD ROM or CD ROM, or transmitted over a network, and executed by a processor. The present invention also provides a computer system for analyzing physiological states, levels of disease states and/or therapeutic efficacy. The computer system comprises a processor, and memory coupled to said processor which encodes one or more programs. The programs encoded in memory cause the processor to perform the steps of the above methods wherein the expression profiles and information about physiological, pharmacological and disease states are received by the computer system as input. Computer systems may be used to execute the software of an embodiment of the invention (see, e.g., U.S. Pat. No. 5,733,729).

7. Providing Appropriate Treatment and Prevention Regimes to Patient

Upon a positive determination or confirmation that a patient has experienced an ischemic event, and a determination of the cause of the ischemic event, e.g., using established clinical procedures and/or the biomarkers provided herein and known in the art, the methods further provide for the step of prescribing, providing or administering a regime for the prophylaxis or treatment of ischemia. By diagnosing the occurrence and/or the cause of ischemia using the biomarkers described herein, a patient can rapidly receive treatment that is tailored to and appropriate for the type of ischemia that has been experienced, or that the patient is at risk of experiencing.

For example, if the expression levels of the plurality of ischemia-associated biomarkers indicate the occurrence or risk of ischemia, a positive diagnosis of ischemia can be supported or confirmed using methods known in the art. For example, the patient can be subject to MRI imaging of brain and vessels, additional blood tests, EKG, and/or echocardiogram. Patients who have experienced ischemic transient neurological events may undergo extensive evaluation of the heart, vasculature, blood and brain, and may receive stroke prevention therapy such as antiplatelet/anticoagulation, antihypertensive medication and lipid lowering therapy.

If the expression levels of the plurality of biomarkers indicate the occurrence or risk of an ischemic transient neurological event (e.g., transient ischemic attacks (TIA) or transient cerebral ischemia), the patient can be prescribed a regime of medications and/or life-style adjustments (e.g., diet, exercise, stress) to minimize risk factors can be recommended, including reducing blood pressure and cholesterol levels, and controlling diabetes. Several medications can be used to decrease the likelihood of a stroke after a transient ischemic attack. The medication selected will depend on the location, cause, severity and type of TIA, if TIA has occurred. For example, the patient may be prescribed a regime of an anti-platelet drug. The most frequently used anti-platelet medication is aspirin. An alternative to aspirin is the anti-platelet drug clopidogrel (Plavix). Some studies indicate that aspirin is most effective in combination with another anti-platelet drug. In some embodiments, the patient is prescribed a combination of low-dose aspirin and the anti-platelet drug dipyridamole (Aggrenox), to reduce blood clotting. Ticlopidine (Ticlid) is another anti-platelet medication that finds use to prevent or reduce the risk of stroke in patients who have experienced TIA. In some embodiments, the patient may be prescribed a regime of an anticoagulant. Exemplary anticoagulants include aspirin, heparin, warfarin, and dabigatran. Patients having a moderately or severely narrowed neck (carotid) artery, may require or benefit from carotid endarterectomy to clear carotid arteries of fatty deposits (atherosclerotic plaques) before another TIA or stroke can occur. In some embodiments, the patient may require or benefit from carotid angioplasty, or stenting.

In cases where a non-ischemic transient neurological event (TNE) is indicated, further evaluation to the cause of the non-ischemic TNE can be performed. For example, the subject can be given tests to determine if a migraine or seizure was experienced, and receive proper treatment. Patients with non-ischemic transient neurological events undergo different diagnostic evaluation and therapy, such as EEG and anti-seizure medication for seizures, and anti-migraine medication for migraines.

If the expression levels of the plurality of biomarkers indicate the occurrence or risk of cardioembolic stroke, the patient can be prescribed or administered a regime of an anticoagulant. Exemplary anticoagulants include aspirin, heparin, warfarin, and dabigatran.

If the expression levels of the plurality of biomarkers indicate the occurrence or risk of carotid stenosis, the patient can be prescribed or administered a regime of an anti-platelet drug. The most frequently used anti-platelet medication is aspirin. An alternative to aspirin is the anti-platelet drug clopidogrel (Plavix). Some studies indicate that aspirin is most effective in combination with another anti-platelet drug. In some embodiments, the patient is prescribed a combination of low-dose aspirin and the anti-platelet drug dipyridamole (Aggrenox), to reduce blood clotting. Ticlopidine (Ticlid) is another anti-platelet medication that finds use. Patients having a moderately or severely narrowed neck (carotid) artery, may require or benefit from carotid endarterectomy. This preventive surgery clears carotid arteries of fatty deposits (atherosclerotic plaques) to prevent a first or subsequent strokes. In some embodiments, the patient may require or benefit from carotid angioplasty, or stenting. Carotid angioplasty involves using a balloon-like device to open a clogged artery and placing a small wire tube (stent) into the artery to keep it open.

If the expression levels of the plurality of biomarkers indicate the occurrence or risk of atrial fibrillation, the patient can be prescribed a regime of an anti-coagulant (to prevent stroke) and/or a pharmacological agent to achieve rate control. Exemplary anticoagulants include aspirin, heparin, warfarin, and dabigatran. Exemplary rate control drugs include beta blockers (e.g., metoprolol, atenolol, bisoprolol), non-dihydropyridine calcium channel blockers (e.g., diltiazem or verapamil), and cardiac glycosides (e.g., digoxin).

If the expression levels of the plurality of ischemia-associated biomarkers indicate the occurrence or risk of lacunar stroke, a positive diagnosis of lacunar stroke can be supported or confirmed using methods known in the art. For example, the patient can be subject to clinical evaluation (e.g., determination of one or more of the lacunar syndromes, including (1) Pure motor stroke/hemiparesis, (2) Ataxic hemiparesis, (3) Dysarthria/clumsy hand, (4) Pure sensory stroke, and (5) Mixed sensorimotor stroke), radiologic imaging, retinal imaging, evaluation of blood-brain barrier permeability, evidence of microhemorrhage and blood endothelial markers (e.g., (homocysteine, intercellular adhesion molecule 1 (ICAM1), thrombomodulin (TM), tissue factor (TF) and tissue factor pathway inhibitor (TFPI); Hassan, et al., *Brain* (2003) 126(Pt 2):424-32; and Hassan, et al., *Brain*. (2004) 127(Pt 1):212-9). Upon a positive diagnosis of lacunar stroke, the patient may be administered tissue plasminogen activator within three hours of an ischemic event if the patient is without contraindications (i.e. a bleeding diathesis such as recent major surgery or cancer with brain metastases). High doses aspirin may be given within 48 hours of an ischemic event. For long term prevention of recurrence, medical regimens may be aimed towards correcting the underlying risk factors for lacunar infarcts such as hypertension, diabetes mellitus and cigarette smoking.

8. Solid Supports and Kits

The invention further provides, a solid support comprising a plurality of nucleic acid probes that hybridize to a plurality (e.g., two or more, or all) of the genes set forth in Tables 3 and/or 5, and optionally Table 10, as described herein. For example, the solid support can be a microarray attached to a plurality of nucleic acid probes that hybridize to a plurality (e.g., two or more, or all) of the genes set forth in Tables 3 and/or 5, and optionally Table 10. In various embodiments, the solid supports are configured to exclude genes not associated with or useful to the diagnosis, prediction or confirmation of an ischemic event, or for stroke generally. For example, genes that are overexpressed or underexpressed less than 1.2-fold in subjects with ischemia in comparison to a control level of expression can be excluded from the present solid supports. In some embodiments, genes that are overexpressed or underexpressed less than 1.2-fold in subjects with ischemic stroke, including transient cerebral ischemia, lacunar stroke, cardioembolic stroke, atherothrombotic stroke, TIA, and stroke subsequent to atrial fibrillation, in comparison to a control level of expression can be excluded from the present solid supports. The solid support may optionally further comprise a plurality of nucleic acid probes that hybridize to a plurality (e.g., two or more, or all) of the genes useful for the diagnosis of ischemic stroke, cardioembolic stroke, carotid stenosis, and/or atrial fibrillation, as described herein. In various embodiments, the solid support comprises 1000 or fewer (e.g., 900, 800, 700, 600, 500 or fewer) nucleic acid probes that hybridize to a plurality of ischemia-associated genes, as described herein. The solid support may be a component in a kit.

The invention also provides kits for diagnosing ischemia or a predisposition for developing ischemia. For example, the invention provides kits that include one or more reaction vessels that have aliquots of some or all of the reaction components of the invention in them. Aliquots can be in liquid or dried form. Reaction vessels can include sample processing cartridges or other vessels that allow for the containment, processing and/or amplification of samples in the same vessel. The kits may comprise a plurality of nucleic acid probes that hybridize to a plurality (e.g., two or more, or all) of the genes set forth in Tables 3 and/or 5. In one embodiment, the kits comprise a plurality of nucleic acid probes that hybridize to a plurality of the genes set forth in Table 3. In one embodiment, the kits comprise a plurality of nucleic acid probes that hybridize to a plurality of the genes set forth in Table 5. In one embodiment, the kits further comprise a plurality of nucleic acid probes that hybridize to a plurality of the genes set useful for the diagnosis of ischemic stroke, cardioembolic stroke, carotid stenosis, atrial fibrillation, and/or transient ischemic attacks (TIA), as described herein. The probes may be immobilized on an array as described herein.

In addition, the kit can comprise appropriate buffers, salts and other reagents to facilitate amplification and/or detection reactions (e.g., primers, labels) for determining the expression levels of a plurality of the genes set forth in Tables 3 and/or 5. In one embodiment, the kit comprises appropriate buffers, salts and other reagents to facilitate amplification and/or detection reactions (e.g., primers, labels) for determining the expression levels of a plurality of the genes set forth in Table 3. In one embodiment, the kit comprises appropriate buffers, salts and other reagents to facilitate amplification and/or detection reactions (e.g., primers, labels) for determining the expression levels of a plurality of the genes set forth in Table 5. In one embodiment, the kit further comprises appropriate buffers, salts and other reagents to facilitate amplification and/or detection reactions (e.g., primers) for determining the expression levels of a plurality of the genes useful for the diagnosis of ischemic stroke, cardioembolic stroke, carotid stenosis, atrial fibrillation, and/or transient ischemic attacks (TIA), as described herein. The kits can also include written instructions for the use of the kit.

In one embodiment, the kits comprise a plurality of antibodies that bind to a plurality of the biomarkers set forth in Tables 3 and/or 5. The kits may further comprise a plurality of antibodies that bind to a plurality of the biomarkers useful for the diagnosis of ischemic stroke, cardioembolic stroke, carotid stenosis, atrial fibrillation, and/or transient ischemic attacks (TIA), as described herein. The antibodies may or may not be immobilized on a solid support, e.g., an ELISA plate.

EXAMPLES

The following examples are offered to illustrate, but not to limit the claimed invention.

Example 1

Ischemic Transient Neurological Events (TNE) Identified by Immune Response to Cerebral Ischemia Subjects and Methods
1. Study Patients Patients with ischemic stroke, TIA, and controls were enrolled from the University of California Davis, and the University of California San Francisco. Study protocols were approved by the institutional review boards at each site and written informed consent was obtained from each patient. All patients received standardized clinical evaluations, including medical history, brain imaging, Doppler, vascular angiography, electrocardiogram, echocardiogram, and 24-48 hour cardiac monitoring. Blood samples were drawn into PAXgene tubes (PreAnalytiX, Hilden, Germany) within 72 hours of symptom onset for gene expression analysis.

The diagnoses of stroke, TIA and TNE of nonischemic etiology required consensus of 3 study neurologists. Subjects where a consensus was not obtained were classified as TNE of unclear etiology. A derivation cohort of TIA (n=26), ischemic stroke (n=94) and matched vascular risk factor controls (n=44) were used to identify genes associated with cerebral ischemia (FIG. 1, Table 1). TIA was defined as an episode of neurological dysfunction lasting <24 hours resulting from focal cerebral ischemia with no restricted diffusion on MRI. Ischemic stroke was defined by neurological deficits persisting longer than 24 hours with acute cerebral infarction on imaging. Patients with intracerebral hemorrhage or hemorrhagic infarction were excluded from study. Stroke subtype was classified as large-artery atherosclerotic, cardioembolic, small-vessel lacunar, and cryptogenic as previously described (Adams, et al., *Stroke*. (1993) 24:35-41). Controls were subjects with vascular risk factors without symptomatic cardiovascular disease (stroke, myocardial infarction, peripheral vascular disease) who were similar in age, race, and gender to TIA and stroke subjects. Differences between groups were analyzed using Fisher's exact test, two-tailed t-test, or Wilcoxon-Mann-Whitney test where appropriate (Stata 10.1, College Station, Tex., USA).

TABLE 1

Demographic variables for TIA and ischemic stroke patients compared to vascular risk factor controls.

|  | Control | TIA | | Ischemic Stroke | |
| --- | --- | --- | --- | --- | --- |
|  | (n = 44) | (n = 26) | p | (n = 94) | p |
| Age years (SD) | 62.5 (7.0) | 65.6 (11.4) | 0.17 | 64.5 (10.9) | 0.29 |
| Race Caucasian n (%) | 33 (75%) | 15 (57.9%) | 0.14 | 57 (60.6%) | 0.10 |
| Gender Male n (%) | 22 (50%) | 13 (50%) | 1.00 | 46 (48.9%) | 0.91 |
| Hypertension n (%) | 31 (72.1%) | 19 (73.1%) | 0.93 | 59 (66.3%) | 0.86 |
| Diabetes n (%) | 12 (30%) | 9 (34.6%) | 0.70 | 27 (30.3%) | 0.97 |
| Hyperlipidemia n (%) | 18 (51.4%) | 16 (61.5%) | 0.44 | 34 (38.2%) | 0.18 |

TABLE 1-continued

Demographic variables for TIA and ischemic stroke patients compared to vascular risk factor controls.

|  | Control | TIA | | Ischemic Stroke | |
|---|---|---|---|---|---|
|  | (n = 44) | (n = 26) | p | (n = 94) | p |
| Atrial fibrillation n (%) | 2 (6.3%) | 2 (7.7%) | 0.83 | 10 (11.2%) | 0.42 |
| Prior Stroke/TIA n (%) | 0 | 8 (30.6%) | 0.08 | 24 (27.0%) | 0.09 |
| Stroke/TIA Subtype n (%) |  |  |  |  |  |
| Large Vessel n(%) | N/A | 5 (19.2%) |  | 14 (14.9%) |  |
| Cardioembolic n (%) | N/A | 6 (23.1%) |  | 23 (24.4%) |  |
| Small Vessel n (%) | N/A | 4 (15.3%) |  | 29 (30.8%) |  |
| Cryptogenic n (%) | N/A | 11 (42.3%) |  | 28 (29.8%) |  |
| NIHSS-24 hr (IQR) | N/A | 0 |  | 10.3 (8.7-12.0) |  |
| Hours since TIA/Stroke (SD) | N/A | 33.7 (21.0) |  | 34.7 (22.6) |  | p-values represent the comparison of TIA versus control and ischemic stroke versus control.
Abbreviations:
IQR, Interquartile range;
NIHSS, National Institutes of Health Stroke Scale;
SD, standard deviation.

The genes associated with cerebral ischemia were evaluated in a validation cohort comprised of ischemic TNE (n=17) and nonischemic TNE (n=13) (Table 2). Ischemic TNE were patients with transient neurological symptoms with DWI-positive MRI and minor strokes with an NUBS <5 at 24 hours. Nonischemic TNE included patients with migraine, seizure or syncope. They had no evidence of infarction on MRI and a clinical presentation inconsistent with transient ischemia.

TABLE 2

Characteristics of patients with transient ischemic attacks with restricted diffusion on MRI/minor stroke and nonischemic transient neurological events (TNE)

| Characteristic | DWI+/Minor Stroke (n = 17) | NonIschemic TNE (n = 13) |
|---|---|---|
| Age years (SD) | 60.3 (12.0) | 58.0 (12.2) |
| Male n (%) | 7 (41.2%) | 4 (30.8%) |
| Caucasian n (%) | 9 (52.9%) | 11 (84.6%) |
| Hypertension n (%) | 14 (82.4%) | 5 (38.5%) |
| Diabetes n (%) | 8 (47.1%) | 1 (7.7%) |
| Hyperlipidemia n (%) | 6 (35.3%) | 10 (76.9%) |
| Prior Stroke/TIA n (%) | 5 (29.4%) | 0 |
| NIHSS Admission (IQR) | 2.9 (1-4) | N/A |
| Systolic BP mmHg (SD) | 168.2 (31.1) | 135.3 (9.3) |
| Diastolic BP mmHg (SD) | 87.5 (17.1) | 79.7 (4.5) |

Genes associated with cerebral ischemia were used predict ischemia in TNE of unclear etiology (n=14) (FIG. 1). TNE of unclear etiology were patients with a transient neurological event where diagnostic consensus was not obtained between the three study neurologists, and included two subjects where TIA was thought to be the cause but a brain MRI was not available for review.

2. Sample Processing

A venous blood sample was collected in PAXgene tubes within 72 hours of stroke or TIA onset (PreAnalytiX, Germany). Samples were stored at −80° C. and processed at the same time in the same laboratory to reduce batch effect. Total RNA was isolated according to the manufacturer's protocol (PAXgene blood RNA kit; Pre-AnalytiX). RNA concentration was determined by Nano-Drop (Thermo Fisher) and RNA quality by Agilent 2100 Bioanalyzer. Samples required A260/A280 absorbance ratios of purified RNA ≥2.0 and 28S/18S rRNA ratios ≥1.8. NuGEN's Ovation Whole Blood Solution (NuGEN Technologies, San Carlos, Calif.) was used for reverse transcription, amplification, and sample labeling. Hybridization of each RNA sample was performed according to the manufacturer's protocol on Affymetrix Human U133 Plus 2.0 GeneChips (Affymetrix Santa Clara, Calif.). Arrays were washed and processed on a Fluidics Station 450 and scanned on a GeneChip Scanner 3000. Samples were randomly assigned to microarray batch stratified by diagnosis.

3. Microarray Data Analysis

Microarray data files were pre-processed using robust multichip averaging (RMA), mean-centering standardization and log 2 transformation (Partek Genomics Suite 6.4, Partek Inc., St. Louis, Mo.). Nonspecific probesets with an interquartile range <0.5 across the all subjects were filtered as previously described (Hackstadt, et al., *BMC Bioinformatics*. (2009) 10:11; Gentleman R. Bioinformatics and computational biology solutions using r and bioconductor. *Statistics for biology and health*. 2005:xix, 473 pp). Patients with TIA and ischemic stroke were compared to controls using Analysis of Covariance (ANCOVA) adjusted for age and batch. The analyses included TIA versus controls and ischemic stroke versus controls. After Benjamini-Hochberg false discovery rate (FDR) correction for multiple comparisons, probesets with a corrected p-value <0.05 and fold change ≥|1.2| were considered significant.

4. Gene Functional Analysis

To identify functional pathways associated with the differentially expressed genes, Ingenuity Pathway Analysis (IPA, Ingenuity Systems®, on the internet at ingenuity.com) was used. Pathways with a greater number of genes than expected by chance were considered significant (p<0.05, Fisher's exact test). To identify genes associated with specific immune cells, the list of differentially expressed genes for TIA and stroke were overlapped with previously published lists of genes shown to be unique to granulocytes, natural killer cells, monocytes, B-cells, CD4 T-cells, and CD8 T-cells (Watkins, et al., *Blood*. (2009) 113:e1-9).

5. Prediction Analysis

The probesets common to ischemic stroke and TIA were used to develop a prediction model to discriminate ischemia from controls (FIG. 1). This control group was used to identify genes due to ischemia and not due to vascular risk factors. From the list of 74 common ischemia genes, the optimal genes to discriminate ischemia from controls were identified using forward selection linear discriminant analysis (LDA). LDA is an analytical method that identifies a linear combination of features to separate two or more classes. For this analysis, the genes expressed in blood were the features, and the classes were ischemia and non-ischemia (Table 3). A panel of 26 genes (Table 3, in bold) was identified and used to develop an LDA prediction model to distinguish ischemia from controls. This model was evaluated using 10-fold leave-one-out cross-validation analysis and in a second cohort of subjects with TIA-DWI positive/minor stroke (n=17) and nonischemic TNE (n=13: migraine n=7; seizure n=3; syncope n=3) (FIG. 1). The developed model was then used to predict TNE of unclear etiology.

TABLE 3

The 74 common probesets (63 genes) significantly different between patients with TIA and matched controls and ischemic stroke and matched controls (FDR <0.05, fold change >|1.2|).

| Affy Probeset ID | Gene Symbol | Gene Title | p-value (TIA vs. Control) | Fold-Change (TIA vs Control) | p-value (Stroke vs Control) | Fold-Change (Stroke vs Control) |
|---|---|---|---|---|---|---|
| 222435_s_at | UBE2J1 | ubiquitin-conjugating enzyme E2, J1 (UBC6 homolog, yeast) | 2.53E−07 | 1.98 | 2.59E−13 | 2.11 |
| 202262_x_at | DDAH2 | dimethylarginine dimethylaminohydrolase 2 | 1.21E−05 | 1.88 | 4.81E−05 | 1.54 |
| 1552701_a_at | CARD16 | caspase recruitment domain family, member 16 | 2.21E−05 | 1.94 | 6.06E−08 | 1.89 |
| 203773_x_at | BLVRA | biliverdin reductase A | 2.51E−05 | 1.85 | 4.72E−05 | 1.55 |
| 227616_at | BCL9L | B-cell CLL/lymphoma 9-like | 5.66E−05 | −1.84 | 8.31E−04 | −1.45 |
| 217823_s_at | UBE2J1 | ubiquitin-conjugating enzyme E2, J1 (UBC6 homolog, yeast) | 6.05E−05 | 1.88 | 5.25E−06 | 1.70 |
| 217824_at | UBE2J1 | ubiquitin-conjugating enzyme E2, J1 (UBC6 homolog, yeast) | 6.65E−05 | 1.77 | 2.80E−07 | 1.74 |
| 227612_at | ELAVL3 | ELAV (embryonic lethal, abnormal vision,Drosophila )-like 3 (Hu antigen C) | 6.88E−05 | 1.87 | 9.18E−04 | 1.47 |
| 238016_s_at | LOC100129105 | Similar to hCG1821214 | 9.03E−05 | 1.71 | 3.17E−06 | 1.61 |
| 205896_at | SLC22A4 | solute carrier family 22 (organic cation/ergothioneine transporter), member 4 | 1.03E−04 | 1.84 | 1.80E−04 | 1.54 |
| 205042_at | GNE | glucosamine (UDP-N-acetyl)-2-epimerase/N-acetylmannosamine kinase | 1.27E−04 | −1.72 | 1.33E−04 | −1.49 |
| 210156_s_at | PCMT1 | protein-L-isoaspartate (D-aspartate) O-methyltransferase | 1.34E−04 | 1.70 | 5.33E−04 | 1.43 |
| 210889_s_at | FCGR2B | Fc fragment of IgG, low affinity IIb, receptor (CD32) | 1.58E−04 | 1.92 | 4.54E−05 | 1.68 |
| 1552677_a_at | DIP2A | DIP2 disco-interacting protein 2 homolog A (Drosophila ) | 1.68E−04 | −1.70 | 5.36E−04 | −1.43 |
| 203065_s_at | CAV1 | caveolin 1, caveolae protein, 22 kDa | 1.79E−04 | 1.74 | 1.04E−03 | 1.43 |
| 242251_at | SPATA5 | spermatogenesis associated 5 | 1.80E−04 | −1.85 | 5.51E−04 | −1.52 |
| 232303_at | ZNF608 | zinc finger protein 608 | 2.05E−04 | 1.85 | 4.27E−06 | 1.77 |
| 214933_at | CACNA1A | calcium channel, voltage-dependent, P/Q type, alpha 1A subunit | 2.26E−04 | 1.92 | 1.45E−03 | 1.51 |
| 203371_s_at | NDUFB3 | NADH dehydrogenase (ubiquinone) 1 beta subcomplex, 3, 12 kDa | 2.49E−04 | 1.76 | 8.32E−05 | 1.56 |
| 211366_x_at | CASP1 | caspase 1, apoptosis-related cysteine peptidase (interleukin 1, beta, convertase | 2.93E−04 | 1.72 | 9.95E−05 | 1.54 |
| 212722_s_at | JMJD6 | jumonji domain containing 6 | 3.19E−04 | 1.68 | 4.61E−04 | 1.45 |
| 219308_s_at | AK5 | adenylate kinase 5 | 4.65E−04 | −1.78 | 3.78E−06 | −1.76 |
| 221011_s_at | LBH | limb bud and heart development homolog (mouse) | 4.74E−04 | −1.69 | 5.84E−05 | −1.57 |
| 218732_at | PTRH2 | peptidyl-tRNA hydrolase 2 | 5.46E−04 | 1.72 | 6.43E−06 | 1.70 |
| 214447_at | ETS1 | v-ets erythroblastosis virus E26 oncogene homolog 1 (avian) | 5.51E−04 | −1.72 | 9.12E−04 | −1.47 |
| 1562028_at | CCND3 | Cyclin D3 | 6.37E−04 | −1.83 | 4.42E−04 | −1.58 |
| 206513_at | AIM2 | absent in melanoma 2 | 8.76E−07 | 2.09 | 2.13E−05 | 1.59 |
| 226585_at | NEIL2 | nei like 2 (E. coli) | 1.34E−06 | −2.09 | 2.46E−06 | −1.70 |
| 219394_at | PGS1 | phosphatidylglycerophosphate synthase 1 | 1.36E−06 | 1.97 | 6.62E−05 | 1.51 |
| 225675_at | C14orf101 | chromosome 14 open reading frame 101 | 2.46E−06 | 2.03 | 1.29E−05 | 1.62 |
| 214229_at | DNAH17 | dynein, axonemal, heavy chain 17 | 2.49E−06 | 1.98 | 5.67E−05 | 1.53 |
| 235593_at | ZEB2 | zinc finger E-box binding homeobox 2 | 2.76E−06 | 1.95 | 1.81E−05 | 1.56 |
| 214909_s_at | DDAH2 | dimethylarginine dimethylaminohydrolase 2 | 2.96E−06 | 1.94 | 7.33E−06 | 1.60 |
| 206954_at | WIT1 | Wilms tumor upstream neighbor 1 | 3.27E−06 | 1.92 | 1.43E−04 | 1.47 |
| 204574_s_at | MMP19 | matrix metallopeptidase 19 | 5.46E−06 | −1.95 | 2.25E−04 | −1.49 |
| 226715_at | FOXK1 | forkhead box K1 | 6.31E−06 | −2.05 | 1.91E−08 | −1.95 |
| 228924_s_at | UBE2J1 | Ubiquitin-conjugating enzyme E2, J1 (UBC6 homolog, yeast) | 7.11E−06 | 1.97 | 2.64E−08 | 1.88 |
| 232034_at | LOC203274 | Hypothetical protein LOC203274 | 7.38E−06 | 1.98 | 1.54E−07 | 1.81 |
| 215537_x_at | DDAH2 | dimethylarginine dimethylaminohydrolase 2 | 7.78E−06 | 1.87 | 2.91E−05 | 1.53 |
| 209870_s_at | APBA2 | amyloid beta (A4) precursor protein-binding, family A, member 2 | 9.94E−06 | −1.92 | 3.01E−07 | −1.76 |
| 209369_at | ANXA3 | annexin A3 | 1.34E−05 | 1.92 | 2.11E−06 | 1.69 |
| 231099_at | FKBP15 | FK506 binding protein 15, 133 kDa | 3.97E−05 | 1.91 | 1.17E−03 | 1.45 |
| 217825_s_at | UBE2J1 | ubiquitin-conjugating enzyme E2, J1 (UBC6 homolog, yeast) | 4.84E−05 | 1.82 | 4.87E−09 | 1.92 |
| 231178_at | SPATA4 | spermatogenesis associated 4 | 7.01E−05 | 1.93 | 6.00E−04 | 1.52 |
| 203005_at | LTBR | lymphotoxin beta receptor (TNFR superfamily, member 3) | 7.42E−05 | 1.83 | 2.75E−04 | 1.50 |
| 214748_at | N4BP2L2 | NEDD4 binding protein 2-like 2 | 9.48E−05 | 1.89 | 1.08E−03 | 1.48 |
| 209514_s_at | RAB27A | RAB27A, member RAS oncogene family | 1.03E−04 | 1.83 | 4.97E−05 | 1.60 |
| 224582_s_at | NUCKS1 | nuclear casein kinase and cyclin-dependent kinase substrate 1 | 1.09E−04 | −1.95 | 2.99E−05 | −1.71 |
| 1570035_at | TBC1D10A | TBC1 domain family, member 10A | 1.21E−04 | −1.81 | 1.10E−04 | −1.55 |
| 1552703_s_at | CARD16 /// CASP1 | caspase recruitment domain family, member 16 /// caspase 1, apoptosis-related cy | 1.23E−04 | 1.82 | 3.07E−06 | 1.72 |
| 211959_at | IGFBP5 | insulin-like growth factor binding protein 5 | 1.28E−04 | 1.80 | 5.29E−04 | 1.48 |
| 210951_x_at | RAB27A | RAB27A, member RAS oncogene family | 1.43E−04 | 1.81 | 6.50E−05 | 1.58 |
| 228437_at | CNIH4 | cornichon homolog 4 (Drosophila) | 1.44E−04 | 1.73 | 2.45E−05 | 1.57 |
| 213040_s_at | NPTXR | neuronal pentraxin receptor | 1.48E−04 | −1.70 | 1.11E−03 | −1.40 |
| 207500_at | CASP5 | caspase 5, apoptosis-related cysteine peptidase | 1.61E−04 | 1.76 | 3.46E−05 | 1.59 |
| 224581_s_at | NUCKS1 | nuclear casein kinase and cyclin-dependent kinase substrate 1 | 1.80E−04 | −1.79 | 1.85E−05 | −1.64 |
| 223750_s_at | TLR10 | toll-like receptor 10 | 1.93E−04 | 1.85 | 2.20E−04 | 1.57 |

TABLE 3-continued

The 74 common probesets (63 genes) significantly different between patients with TIA
and matched controls and ischemic stroke and matched controls (FDR <0.05, fold change >|1.2|).

| Affy Probeset ID | Gene Symbol | Gene Title | p-value (TIA vs. Control) | Fold-Change (TIA vs Control) | p-value (Stroke vs Control) | Fold-Change (Stroke vs Control) |
|---|---|---|---|---|---|---|
| 225918_at | GLG1 | golgi apparatus protein 1 | 1.93E−04 | −1.84 | 6.67E−05 | −1.62 |
| 223661_at | NUCKS1 | nuclear casein kinase and cyclin-dependent kinase substrate 1 | 2.24E−04 | −1.82 | 2.47E−05 | −1.66 |
| 210135_s_at | SHOX2 | short stature homeobox 2 | 2.30E−04 | 1.75 | 5.08E−05 | 1.58 |
| 243201_at | HNRNPH2 | Heterogeneous nuclear ribonucleoprotein H2 (H') | 2.56E−04 | 1.87 | 2.80E−04 | 1.58 |
| 202652_at | APBB1 | amyloid beta (A4) precursor protein-binding, family B, member 1 (Fe65) | 2.74E−04 | −1.68 | 8.48E−04 | −1.42 |
| 202137_s_at | ZMYND11 | zinc finger, MYND domain containing 11 | 2.74E−04 | −1.68 | 9.35E−05 | −1.51 |
| 230999_at | FLJ39051 | Hypothetical gene supported by AK096370 | 2.89E−04 | 1.72 | 8.89E−05 | 1.54 |
| 212618_at | ZNF609 | zinc finger protein 609 | 2.94E−04 | −1.77 | 8.53E−04 | −1.47 |
| 235119_at | TAF3 | TAF3 RNA polymerase II, TATA box binding protein (TBP)-associated factor, 140 kDa | 3.23E−04 | −1.67 | 3.21E−05 | −1.55 |
| 218627_at | DRAM1 | DNA-damage regulated autophagy modulator 1 | 3.65E−04 | 1.66 | 2.20E−04 | 1.47 |
| 1559754_at | LTB | Lymphotoxin beta (TNF superfamily, member 3) | 3.82E−04 | 1.76 | 8.28E−04 | 1.48 |
| 209970_x_at | CASP1 | caspase 1, apoptosis-related cysteine peptidase (interleukin 1, beta, convertase | 3.93E−04 | 1.70 | 2.07E−04 | 1.51 |
| 226292_at | CAPN5 | calpain 5 | 4.69E−04 | −1.67 | 2.10E−04 | −1.50 |
| 213908_at | WHAMML1 /// WHAMML2 | WAS protein homolog associated with actin, golgi membranes and microtubules-like | 5.08E−04 | −1.72 | 5.55E−06 | −1.70 |
| 214511_x_at | FCGR1B | Fc fragment of IgG, high affinity Ib, receptor (CD64) | 5.20E−04 | 1.64 | 1.84E−04 | 1.48 |
| 211521_s_at | CYTH4 | cytohesin 4 | 5.60E−04 | 1.68 | 7.39E−05 | 1.56 |
| 232249_at | FMNL3 | formin-like 3 | 5.98E−04 | −1.63 | 5.29E−05 | −1.53 |

The list of 26 probesets found to optimally discriminate cerebral ischemia from controls are shown in bold.

Results

Demographic and clinical characteristics of subjects analyzed in the derivation set are shown in Table 1. There were 26 subjects with TIA, 94 with ischemic stroke, and 44 controls. The mean age was 64.1 years (SD±11.0) and 49.3% were male. The cohort was ethnically diverse: 105 (64%) were Caucasian, 28 (17%) were African American, 16 (10%) were Hispanic, 10 (6%) were Asian, and 5 (3%) were of other race. TIA subjects had a mean ABCD2 score of 4.6 (range 2-6). Controls had vascular risk factors but no symptomatic cerebrovascular or cardiovascular disease. Age, gender, race, hypertension, diabetes, and hyperlipidemia were not significantly different between TIA or ischemic stroke and control subjects.

A total of 160 annotated probesets representing 145 genes were significantly different between TIA and control subjects (FDR<0.05 fold change ≥1.2|). A total of 461 annotated probesets representing 413 genes were significantly different between ischemic stroke and control subjects (FDR<0.05 fold change ≥1.2|). There were 74 probesets (46%) of the 160 probesets differentially expressed in TIA that were common to the 461 probesets differentially expressed in ischemic stroke (Table 3 and FIG. 1). Analysis of the common functional pathways between TIA and ischemic stroke are shown in Table 2. Of the common genes and pathways in TIA and stroke, most were associated with activation and development of the immune cells, including TLR5, TLR6, TLR10, CASP1, CASP6, CARD16, IL8, IL10, CD36 and CD86. TREM-1 signaling involving TLR was the top canonical pathway common in TIA and stroke (Table 4). There were 86 probesets unique to TIA (Table 5), the functional analyses of which are shown in Table 6.

TABLE 4

Functional analysis of pathways common to TIA and ischemic stroke.

| | Pathway | Genes | TIA p-value | Stroke p-value |
|---|---|---|---|---|
| Canonical Pathways | TREM1 Signaling | CASP1, CASP5, CD86, FCGR2B, IL8, IL10, TLR5, TLR6, TLR10 | $1.2 \times 10^{-4}$ | $4.2 \times 10^{-6}$ |
| | Communication between Innate and Adaptive Immune Cells | CD86, IL8, IL10, TLR5, TLR6, TRL10 | $1.4 \times 10^{-2}$ | $7.5 \times 10^{-3}$ |
| | Altered B Cell Signaling | CD86, IL10, LTB, TLR5, TLR6, TLR10 | $3.2 \times 10^{-2}$ | $9.6 \times 10^{-3}$ |
| | Role of Patterns Recognition Receptors | C1QC, CASP1, IL10, IRF7, TLR5, TLR6 | $2.8 \times 10^{-2}$ | $2.9 \times 10^{-2}$ |
| Molecular Functions | Leukocyte development | ADM, BATF, BCL6, BCL11A, BCL11B, C1QC, CASP1, CAV1, CCND3, CCR2, CD36, CD59, CD86, ETS1, F5, FCGR2B, FN1, FUS, HGF, IFNAR1, IL8, IL10, IL12RB2, IL2RB, IL5RA, JAG1, JMJD6, KIT, LIFR, LTB, LTBR, MEIS1, MYB, NRBP2L2, NQO2, PLSCR1, PRL, RNASE1, RNASE2, SMAD7, SNRK, SOCS1, TAPBP, TLR5, TLR6, TOP2A, TPP2, WT1, XRCCR | $1.9 \times 10^{-4}$ | $1.6 \times 10^{-6}$ |

TABLE 4-continued

Functional analysis of pathways common to TIA and ischemic stroke.

| Pathway | Genes | TIA p-value | Stroke p-value |
|---|---|---|---|
| Phagocyte development | C1QC, CCR2, CD36, CD86, FCGR2B, FN1, HGF, IFNAR1, IL10, IRF7, KIT, LIFR, LTB, LTBR, MYB, N4BP2L2, RNASE1, RNAS32, SOCS1, TLR5, TLR6 | $7.4 \times 10^{-3}$ | $8.9 \times 10^{-6}$ |
| Inflammatory response | ANXA3, AIM2, BCL6, CASP1, CASP4, CASP5, CAV1, CCR2, CD36, CD59, CD86, CD164, COL1A1, CXCR7, EDNRB, ETS1, F5, FCGR1A, FCGR2B, FN1, GM2A, GNA12, HGF, IFNAR1, IL8, IL10, IL12RB2, IL18BP, IL2RB, JMJD6, KIT, LTB, LTBR, MARCO, MEIS1, MYLK3, NMV, NQO2, PFDN6, PLSCR1, PRL, RAB27A, RNASE2, S100A12, S1PR3, SERPINF1, SLPI, SIGLEC8, SMAD7, SOCS1, TAPBP, TLR5, TLR6 | $4.7 \times 10^{-4}$ | $5.0 \times 10^{-5}$ |

The canonical and functional pathways represented greater than expected by chance are shown (p < 0.05, Fisher's exact test), along with the genes expressed in the listed pathways. Pathways represent alterations in the blood that occur in patients with TIA and ischemic stroke. Genes that are underlined represent those common to TIA and ischemic stroke.

TABLE 5

The 86 probesets (83 genes) unique to TIA (FDR <0.05, fold change >|1.2|).

| Affy Probeset ID | Gene Symbol | Gene Title | p-value (TIA vs. Control) | Fold-Change (TIA vs. Control) |
|---|---|---|---|---|
| 202912_at | ADM | adrenomedullin | 3.89E-04 | 1.75 |
| 204289_at | ALDH6A1 | aldehyde dehydrogenase 6 family, member A1 | 1.94E-05 | -2.08 |
| 229887_at | ALS2CL | ALS2 C-terminal like | 3.52E-04 | -1.77 |
| 239196_at | ANKRD22 | ankyrin repeat domain 22 | 3.41E-04 | 1.75 |
| 207798_s_at | ATXN2L | ataxin 2-like | 2.93E-04 | -1.73 |
| 1555605_x_at | BAGE | B melanoma antigen | 6.25E-04 | 1.72 |
| 213336_at | BAZ1B | bromodomain adjacent to zinc finger domain, 1B | 3.86E-04 | -1.76 |
| 207326_at | BTC | betacellulin | 5.70E-05 | 1.86 |
| 236853_at | C13orf16 | chromosome 13 open reading frame 16 | 1.65E-04 | 1.88 |
| 210672_s_at | C16orf35 | chromosome 16 open reading frame 35 | 4.95E-04 | -1.81 |
| 243507_s_at | C20orf196 | chromosome 20 open reading frame 196 | 6.15E-04 | -1.69 |
| 1552755_at | C9orf66 | chromosome 9 open reading frame 66 | 5.74E-04 | 1.77 |
| 239771_at | CAND1 | cullin-associated and neddylation-dissociated 1 | 6.41E-08 | -2.23 |
| 205166_at | CAPN5 | calpain 5 | 3.30E-04 | -1.85 |
| 1554744_at | CARD16 | caspase recruitment domain family, member 16 | 1.09E-05 | 2.02 |
| 239871_at | CLTC | Clathrin, heavy chain (Hc) | 1.21E-05 | -2.05 |
| 219717_at | DCAF16 | DDB1 and CUL4 associated factor 16 | 5.45E-04 | -1.66 |
| 236274_at | EIF3B | eukaryotic translation initiation factor 3, subunit B | 5.59E-04 | -1.57 |
| 205757_at | ENTPD5 | ectonucleoside triphosphate diphosphohydrolase 5 | 5.78E-04 | -1.75 |
| 231911_at | ERMN | ermin, ERM-like protein | 3.27E-04 | -1.76 |
| 1565715_at | FUS | Fusion (involved in t(12; 16) in malignant liposarcoma) | 1.53E-04 | -2.00 |
| 231108_at | FUS | fusion (involved in t(12; 16) in malignant liposarcoma) | 4.42E-04 | -1.81 |
| 1565717_s_at | FUS /// NR1H3 | fusion (involved in t(12; 16) in malignant liposarcoma) /// nuclear receptor subf | 3.94E-04 | -1.87 |
| 1557350_at | G3BP1 | GTPase activating protein (SH3 domain) binding protein 1 | 4.92E-05 | -1.91 |
| 205164_at | GCAT | glycine C-acetyltransferase (2-amino-3-ketobutyrate coenzyme A ligase) | 4.57E-04 | -1.77 |
| 36475_at | GCAT | glycine C-acetyltransferase (2-amino-3-ketobutyrate coenzyme A ligase) | 1.50E-04 | -1.85 |
| 207235_s_at | GRM5 | glutamate receptor, metabotropic 5 | 5.20E-04 | 1.72 |
| 204550_x_at | GSTM1 | glutathione S-transferase mu 1 | 6.06E-04 | -1.77 |
| 215333_x_at | GSTM1 | glutathione S-transferase mu 1 | 3.95E-04 | -1.82 |
| 204418_x_at | GSTM2 | glutathione S-transferase mu 2 (muscle) | 3.49E-04 | -1.80 |
| 232207_at | GUSBL2 | glucuronidase, beta-like 2 | 2.97E-06 | -2.20 |
| 1559520_at | GYPA | Glycophorin A (MNS blood group) | 5.00E-04 | 1.76 |
| 202474_s_at | HCFC1 | host cell factor C1 (VP16-accessory protein) | 8.25E-05 | -1.92 |
| 1555673_at | hCG_1749898 | KRTAP2-4 protein | 4.54E-04 | 1.67 |
| 1556351_at | HCN1 | hyperpolarization activated cyclic nucleotide-gated potassium channel 1 | 3.42E-04 | 1.62 |
| 220085_at | HELLS | helicase, lymphoid-specific | 9.00E-05 | -1.83 |
| 240703_s_at | HERC1 | hect (homologous to the E6-AP (UBE3A) carboxyl terminus) domain and RCC1 (CHC1)- | 4.82E-04 | -1.78 |
| 66053_at | HNRNPUL2 | heterogeneous nuclear ribonucleoprotein U-like 2 | 5.94E-04 | -1.76 |
| 219985_at | HS3ST3A1 | heparan sulfate (glucosamine) 3-O-sulfotransferase 3A1 | 4.22E-04 | 1.66 |
| 117_at | HSPA6 | heat shock 70 kDa protein 6 (HSP70B') | 5.07E-04 | 1.79 |
| 1564231_at | IFT80 | intraflagellar transport 80 homolog (Chlamydomonas) | 4.65E-04 | -1.76 |
| 229538_s_at | IQGAP3 | IQ motif containing GTPase activating protein 3 | 3.96E-04 | 1.66 |

TABLE 5-continued

The 86 probesets (83 genes) unique to TIA (FDR <0.05, fold change >|1.2|).

| Affy Probeset ID | Gene Symbol | Gene Title | p-value (TIA vs. Control) | Fold-Change (TIA vs. Control) |
|---|---|---|---|---|
| 208436_s_at | IRF7 | interferon regulatory factor 7 | 1.38E−05 | 1.96 |
| 202714_s_at | KIAA0391 | KIAA0391 | 7.30E−05 | −1.98 |
| 215750_at | KIAA1659 | KIAA1659 protein | 7.50E−05 | −1.80 |
| 242851_at | KIAA1919 | KIAA1919 | 3.38E−05 | −1.94 |
| 205876_at | LIFR | leukemia inhibitory factor receptor alpha | 5.42E−04 | 1.70 |
| 216868_s_at | LOC100129656 | hypothetical LOC100129656 | 2.62E−04 | −1.85 |
| 217060_at | LOC100293532 | similar to hCG2002964 | 1.70E−04 | −1.76 |
| 227106_at | LOC440104 | hypothetical LOC440104 | 7.34E−05 | −1.80 |
| 212274_at | LPIN1 | lipin 1 | 3.28E−04 | −1.73 |
| 226023_at | MAP2K7 | mitogen-activated protein kinase kinase 7 | 3.61E−04 | −1.83 |
| 205018_s_at | MBNL2 | muscleblind-like 2 (Drosophila) | 1.32E−04 | −1.73 |
| 225456_at | MED1 | mediator complex subunit 1 | 7.32E−05 | −1.98 |
| 242111_at | METTL3 | methyltransferase like 3 | 4.27E−04 | −1.73 |
| 233539_at | NAPEPLD | N-acyl phosphatidylethanolamine phospholipase D | 1.84E−05 | −1.96 |
| 206023_at | NMU | neuromedin U | 2.56E−04 | 1.90 |
| 219789_at | NPR3 | natriuretic peptide receptor C/guanylate cyclase C (atrionatriuretic peptide rec | 3.35E−04 | 1.64 |
| 1553931_at | OSTCL | oligosaccharyltransferase complex subunit-like | 2.80E−04 | 1.78 |
| 206048_at | OVOL2 | ovo-like 2 (Drosophila) | 4.51E−04 | 1.70 |
| 202430_s_at | PLSCR1 | phospholipid scramblase 1 | 3.28E−04 | 1.78 |
| 200844_s_at | PRDX6 | peroxiredoxin 6 | 1.25E−04 | −1.90 |
| 201481_s_at | PYGB | phosphorylase, glycogen; brain | 1.28E−04 | −1.88 |
| 1558773_s_at | RANBP10 | RAN binding protein 10 | 4.88E−05 | −1.99 |
| 227036_at | RASAL2 | RAS protein activator like 2 | 5.53E−04 | 1.68 |
| 1556672_a_at | RBM6 | RNA binding motif protein 6 | 2.06E−04 | −1.76 |
| 226603_at | SAMD9L | sterile alpha motif domain containing 9-like | 5.45E−04 | 1.78 |
| 207570_at | SHOX | short stature homeobox | 1.78E−04 | 1.75 |
| 206634_at | SIX3 | SIX homeobox 3 | 3.63E−04 | 1.63 |
| 223304_at | SLC37A3 | solute carrier family 37 (glycerol-3-phosphate transporter), member 3 | 4.49E−04 | 1.70 |
| 239667_at | SLC3A1 | solute carrier family 3 (cystine, dibasic and neutral amino acid transporters, a | 2.46E−06 | −2.13 |
| 201320_at | SMARCC2 | SWI/SNF related, matrix associated, actin dependent regulator of chromatin, subf | 5.47E−04 | −1.85 |
| 232020_at | SMURF2 | SMAD specific E3 ubiquitin protein ligase 2 | 6.31E−04 | −1.72 |
| 1554473_at | SRGAP1 | SLIT-ROBO Rho GTPase activating protein 1 | 1.38E−04 | 1.73 |
| 210294_at | TAPBP | TAP binding protein (tapasin) | 2.90E−04 | 1.87 |
| 207446_at | TLR6 | toll-like receptor 6 | 1.31E−04 | 1.92 |
| 1569857_s_at | TPP2 | tripeptidyl peptidase II | 9.15E−05 | −1.92 |
| 213943_at | TWIST1 | twist homolog 1 (Drosophila) | 1.71E−04 | 1.78 |
| 206487_at | UNC84A | unc-84 homolog A (C. elegans) | 5.29E−04 | −1.68 |
| 1552536_at | VTI1A | vesicle transport through interaction with t-SNAREs homolog 1A (yeast) | 5.72E−04 | −1.79 |
| 210813_s_at | XRCC4 | X-ray repair complementing defective repair in Chinese hamster cells 4 | 5.38E−04 | 1.70 |
| 238760_at | YARS | tyrosyl-tRNA synthetase | 1.00E−04 | −1.88 |
| 216940_x_at | YBX1 /// YBX1P2 | Y box binding protein 1 /// Y box binding protein 1 pseudogene 2 | 4.26E−04 | −1.88 |
| 208087_s_at | ZBP1 | Z-DNA binding protein 1 | 1.69E−04 | 1.82 |
| 205427_at | ZNF354A | zinc finger 354A | 2.38E−04 | 1.74 |
| 205594_at | ZNF652 | zinc finger protein 652 | 3.92E−04 | −1.83 |

TABLE 6

Functional analysis of the 160 probesets (145 genes) that were significantly different between patients with TIA and matched vascular risk factor controls (FDR<0.05, fold change >|1.2|).

| | Pathway | Genes | p-value |
|---|---|---|---|
| Canonical Pathways | Glutathione Metabolism | GSTM1, GSTM2, IDH3A, PRD86 | $1.9 \times 10^{-4}$ |
| | IL-1 mediated inhibition of RXR function | ALDHGA1, GSTM1, GSTM2, HS3ST3A1, MAP2K7 | $3.0 \times 10^{-3}$ |
| | Aryl Hydrocarbon Receptor Signaling | ALDHGA1, GSTM1, GSTM2, MED1 | $4.7 \times 10^{-3}$ |
| | Phospholipid degradation | LP1N1, NAPEPLD, PRDX6 | $9.4 \times 10^{-3}$ |
| | PPARa/RXRa activation | CAND1, MAP2K7, MED1 | $4.9 \times 10^{-2}$ |
| | NRF2-mediated Oxidative Stress Response | GSTM1, GSTM2, MAP2K7 | $6.4 \times 10^{-2}$ |
| | Apoptosis Signaling | CASPN5, MAP2K7 | $7.0 \times 10^{-2}$ |

TABLE 6-continued

Functional analysis of the 160 probesets (145 genes) that were significantly different between patients with TIA and matched vascular risk factor controls (FDR<0.05, fold change >|1.2|).

| | Pathway | Genes | p-value |
|---|---|---|---|
| Molecular Functions | Glutathione depletion (network) | ADM, BTC, CARD16, FUS, GSTM1, GSTM2, HCFC1, HERC1, HSPA6, IRF7, LPIN1, MAP2K7, MED1, NPR3, PLSCR1, PRDX6, SLC3A1, SMURF2, TAPBP, TLR6, VTI1A, YBX1, ZBP1 | $3.6 \times 10^{-9}$ |
| | Angiogenesis, Endothelia cell activation | ADM, BTC, MED1, YARS | $1.9 \times 10^{-2}$ |
| | Activation of bone marrow precursor cells, colony formation | LIFR, ADM, PLSCR1 | $5.2 \times 10^{-3}$ |
| | Leukocyte attachment, selection | BTC, TAPBP | $5.2 \times 10^{-3}$ |
| | Oxidative stress response | PRDX6, YBX1 | $2.2 \times 10^{-3}$ |
| | Leukocyte development, differentiation | ADM, FUS, HELLS, IRF7, LIFR, PLSCR1, TAPBP, TLR6, TPP2, XRCC4 | $4.2 \times 10^{-2}$ |
| | Macrophage differentiation | IRF7, LIFR, TLR6 | $1.6 \times 10^{-2}$ |

The canonical and functional pathways represented greater than expected by chance are shown (p < 0.05, Fisher's exact test), along with the genes expressed in the listed pathways.

Using genes previously identified as unique to each immune cell type (Watkins, et al., *Blood.* 2009; 113:e1-9), the proportion of cell types expressing RNA in TIA and ischemic stroke were estimated. Genes differentially expressed in TIA were associated with granulocytes and B-cells (FIG. 2). Genes differentially expressed in ischemic stroke were associated with granulocytes, monocytes, natural killer cells (NK) and B-cells, and, to a lesser extent, with megakaryocytes (MK) and CD4 T-cells (FIG. 2).

Of the 74 probesets (63 genes) common to TIA and stroke, a 26 gene panel was identified that optimally distinguished subjects with cerebral ischemia from controls (FIG. 1). An LDA model based on this gene panel correctly predicted 26 out of 26 TIA subjects, 85 out of 94 ischemic stroke subjects, and 41 out of 44 control subjects. On cross-validation analysis, the 26 gene LDA model correctly predicted 89% of cerebral ischemia subjects and 89% of control subjects (FIG. 3). The probability of predicted diagnosis for the majority of subjects with and without ischemia was >90%.

In a validation cohort of TIAs with DWI positive lesions and minor strokes, ischemia was the predicted diagnosis in 17 out of 17 subjects (100%). In a cohort of nonischemic TNE that included patients with migraine, seizure, and syncope, nonischemia was predicted in 10 of 13 subjects (77%). The 26 gene LDA model was then used to predict ischemia in subjects with TNE of unclear etiology. Cerebral ischemia was predicted in 71% (n=10) of subjects, and 29% (n=4) were predicted to be nonischemic events. Though the sample size was small, TNE of unclear etiology predicted to be ischemic had higher ABCD2 scores compared to those predicted to be non-ischemic (Table 7).

TABLE 7

Summary of transient neurological events of unclear etiology predicted to be due to ischemia or nonischemia.

| | Predicted Ischemia (n = 10) | Predicted Nonischemia (n = 4) | p |
|---|---|---|---|
| Age years (SD) | 71.7 (19.2) | 70.3 (13.5) | 0.90 |
| Race Caucasian n (%) | 7 (70%) | 3 (75%) | 1.00 |
| Gender Male n (%) | 4 (40%) | 1 (25%) | 1.00 |
| Hypertension n (%) | 8 (80%) | 2 (50%) | 0.52 |

TABLE 7-continued

Summary of transient neurological events of unclear etiology predicted to be due to ischemia or nonischemia.

| | Predicted Ischemia (n = 10) | Predicted Nonischemia (n = 4) | p |
|---|---|---|---|
| Diabetes n (%) | 4 (40%) | 0 (0%) | 0.25 |
| Hyperlipidemia n (%) | 2 (20%) | 2 (50%) | 0.31 |
| Atrial fibrillation n (%) | 4 (40%) | 0 (0%) | 0.25 |
| ABCD$^2$ Score (IQR) | 5 (4-6) | 3 (2-4) | 0.04 |
| Duration >60 minutes n (%) | 7 (70%) | 2 (50%) | 0.58 |
| Weakness n (%) | 6 (60%) | 1 (25%) | 0.56 |
| Language/Speech n (%) | 4 (40%) | 1 (25%) | 1.00 |
| Sensory symptoms n (%) | 4 (40%) | 3 (75%) | 0.28 |
| Headache n (%) | 2 (20%) | 1 (25%) | 1.00 |

Prediction was based on the 26 gene model developed from common ischemia genes in patients with TIA, ischemic stroke and controls (Fisher's exact test, Wilcoxon-Mann-Whitney test)

DISCUSSION

TIA and stroke were demonstrated to share a common immune response to cerebral ischemia. One half of the genes expressed in TIA were also expressed in stroke, representing activation of innate and adaptive immune responses. This common immune response to ischemia in TIA and stroke was able to distinguish subjects with and without cerebral ischemia. Given the difficulty in determining etiology of transient neurological events, and the significance of this distinction to treatment, a reliable marker that identifies ischemic TNE would be clinically useful.

Immune Response to Ischemia to Identify TIA

TIA is a challenging diagnosis because transient neurological symptoms can be mimicked by several common conditions including migraine, seizure, and syncope (Ferro, et al., *Stroke.* (1996) 27:2225-2229; Castle, et al., *Stroke.* (2010) 41:1367-1370; Bos, et al., *JAMA.* (2007) 298:2877-2885; and Johnston, *JAMA.* (2007) 298:2912-2913). The genes associated with cerebral ischemia, as identified by those common to TIA and ischemic stroke, might identify cerebral ischemia in patients with transient neurological symptoms. We identified a profile of 26 genes able to distinguish TIA and minor stroke subjects from nonischemic TNE. When the profile was used to predict subjects with transient neurological symptoms of unclear etiology, 71% were predicted to be ischemic. This is important as improved recognition of ischemic TNE could improve the delivery of urgent neurovascular evaluation and treatment shown to prevent stroke in TIA. Furthermore, identifying nonischemic TNE that mimic TIA could reduce the costs of hospital observation and extensive evaluation typical of patients diagnosed with TIA.

TNE predicted to be ischemic tended to have higher ABCD2 scores. This is consistent with other studies demonstrating the diagnostic potential of the ABCD2 score to identify transient events due to ischemia (Josephson, et al., Stroke. (2008) 39:3096-3098; Sheehan, et al., Stroke. (2009) 40:3449-3454). An ABCD2 score >4 has been shown to identify 60% of TIAs and 82% of minor strokes (Sheehan, et al., Stroke. (2009) 40:3449-3454). Additionally, an ABCD2 score <4 identified 65% of nonischemic TNE. However, this leaves 40% of TIAs, 18% of minor strokes, and 35% of nonischemic TNE incorrectly identified, indicating that additional methods to distinguish ischemic from nonischemic TNE are required. Diagnosis is critical as early stroke risk is low in nonischemic TNE and is as high as 10-25% in TIA (Johnston, et al., Lancet. (2007) 369:283-292). The genes identified in this study were able to identify all TIAs and minor ischemic strokes, including those subjects with an ABCD2 score <4. Further study is required to determine if an RNA profile can add to the ABCD2 and/or MRI-DWI. The ABCD2 score and/or RNA may be of use in patients where MRI cannot be performed due to contraindications, cost or accessibility. Additionally, RNA may provide additional information that complements the ABCD2 score in TIA. For example patients with a low ABCD2 score with an RNA profile suggesting ischemia may benefit from urgent evaluation. However, this requires additional evaluation.

Immune Response Common to TIA and Stroke

The common peripheral immune response to cerebral ischemia identified was associated with communication between innate and adaptive immune cells, including activation of granulocytes and B cells. This response reflects features shared by TIA and stroke, including immune cell interaction with ischemic but not infarcted tissue, acute thrombosis, and possibly a stress response to acute injury.

Aspects of the common immune response have previously been demonstrated in stroke (Yilmaz, et al., Neuromolecular Med. (2010) 12:193-204). Toll like receptor (TLR) signaling was present in both TIA and stroke, with expression of TLR5, TLR6 and TLR10 identified. TLRs play critical roles in initiating the innate immune response and shaping the adaptive immune response. In mice, knockout of TLR4 results in smaller infarct volumes, better outcomes, and decreased inflammatory markers including IRF-1, iNOS, COX2 and MMP9 (Lund, Curr Opin Immunol. (2008) 20:332-338; Macrez, et al., Lancet Neurol. (2011) 10:471-480). Likewise, knockout of TLR2 can reduce CNS inflammatory markers ICAM-1, IL-6, MCP, and ELAM-1 (Hua F, et al., Brain Res. (2009) 1262:100-108; Abe, et al., Stroke. 2010; 41:898-904), and modulation of TLR-9 can reduce infarct size in mice and non-human primates (Bahj at, et al., J Cereb Blood Flow Metab. (2011) 31:1229-1242). In human stroke, TLR expression is less well characterized. The expression of TLR2 and TLR4 on monocytes at the time of stroke is associated with larger infarct volumes, increased protein levels of IL1B, TNF-α, IL6 and VCAM1 and worse outcomes at 3 months (Urra, et al., Stroke. (2009) 40:1262-1268; Brea, et al., J Cereb Blood Flow Metab. (2011) 31:1424-1431). TLR7 and TLR8 may also be associated with poor outcome and greater inflammatory response (Brea, et al., Clin Immunol. (2011) 139:193-198). Our study suggests that TLR 5, 6 and 10 play a role in the peripheral inflammatory response in both stroke and TIA, suggesting that further study of these receptors is required.

TREM-1 signaling was the top common pathway identified in both TIA and ischemic stroke. TREM (Triggering receptor expressed on myeloid cells) is a receptor that can modulate the innate immune response to prevent excessive inflammation and tissue damage (Dower, et al., J Immunol. (2008) 180:3520-3534; Ford, et al., Curr Opin Immunol. (2009) 21:38-46). TREM regulation of TLR responses is mediated through modification of the caspase-recruitment domain protein (CARD) complex (Hara, et al., Nat Immunol. (2007) 8:619-629; Murillo, et al., Drugs Today (Barc). (2003) 39:415-438). In our study, expression of TLR and CARD genes was identified, with CARD16 being expressed more in TIA than stroke. Further study of TREM-1 signaling in cerebral ischemia may provide a means to modulate inflammation in ischemic brain injury.

The expression of genes associated with B-cells occurred in both stroke and TIA. This suggests that B-cells may play an important role in cerebral ischemia. B-cells have prominent effects on inflammatory responses (Lund, et al., Curr Opin Immunol. (2008) 20:332-338; LeBien, et al., Blood. 2008; 112:1570-1580). Depletion of B cells in multiple sclerosis worsens CNS injury (Ray, et al., J Neuroimmunol. 2011; 230:1-9; Matsushita, et al., J Immunol. (2010) 185: 2240-2252). In experimental stroke, infarct size can be reduced with B cell transfusion (Ren, et al., J Neurosci. (2011) 31:8556-8563). The ability of B-cells to limit CNS injury is dependent on the anti-inflammatory effects of IL-10 (Ren, et al., J Neurosci. (2011) 31:8556-8563; Mann, et al., J Immunol. (2007) 178:3447-3456; Fillatreau, et al., Nat Immunol. (2002) 3:944-950). Our study suggests that B-cells are important in the immune response to cerebral ischemia in stroke and TIA.

Limitations

Sample size was small in this preliminary study. Larger studies are required to ensure TIA and nonischemic TNE populations are comprehensively evaluated. Microarray studies evaluating many genes have an inherent risk of false discovery. Though we adjusted for this risk using FDR corrected p-values and assessed the developed model in a validation cohort, evaluation of identified genes and pathways in a second independent cohort is required. Reliability of findings is increased because identified genes and pathways associated with ischemia were present in both TIA and stroke subjects. Since blood samples were obtained within 72 hours of TIA or stroke, differences in immune response to ischemia that may exist beyond this time remains unclear. Analysis of individual immune cells was performed based on prior studies on genes unique to each cell type. Further evaluation of individual immune cell response to ischemia in stroke and TIA is required. A clinical diagnosis of TIA has limitations in its accuracy, and this may have been introduced into the derived genes to predict ischemia in TNE. Though TIAs were selected based on criteria to make ischemia the most likely etiology, it is possible that some TIA patients were misclassified. Ischemic stroke patients were used to ensure the identified genes were present in patients with definitive cerebral ischemia. Future studies could follow patients with TIA and TNE over time to refine clinical diagnoses. Since short-term risk of stroke confirms that an initial event was a TIA rather than a mimic, the profile may also be valuable as a predictor of stroke risk.

In conclusion, a common peripheral response to ischemia in stroke and TIA was identified. The genes and pathways provide insight into the peripheral inflammatory response to cerebral ischemia. With further study, the common immune response may demonstrate clinical utility to discriminate ischemic from nonischemic causes of TNE, and thus facilitate evaluation and treatment of TIA.

Example 2

Use of Biomarkers for Predicting and/or Diagnosing Myocardial Ischemia

Methods for Predicting Myocardial Ischemia
1. Study Patients

Patients with acute myocardial infarction were enrolled from the University of California Davis. The institutional review board at each site approved the study protocol and written informed consent was obtained from each patient. Patients with myocardial infarction were >18 years of age, and had acute myocardial ischemia. Myocardial ischemia was determined by cardiologist based on medical history, troponin, creatinine kinase, CKMB, bloodwork, electrocardiogram, echocardiogram, and angiography. All patients had standardized clinical evaluations. Blood samples were drawn into PAXgene tubes (PreAnalytiX, Hilden, Germany) within 100 hours of myocardial ischemia onset. A total of 17 subjects were analyzed using the 26 gene expression profiles.

2. Sample Processing

Blood was collected by venipuncture into PAXgene tubes (PreAnalytiX, Germany). Samples were stored frozen and then processed at the same time to minimize technical variation. Total RNA was isolated according to protocol (PAXgene blood RNA kit; Pre-AnalytiX) and analyzed for quality using Agilent 2100 Bioanalyzer and quantity by Nano-drop. Reverse transcription, amplification, and sample labeling were carried out using Nugen's Ovation Whole Blood reagents (Nugen Technologies, San Carlos, Calif.). Each RNA sample was hybridized to Affymetrix Genome U133 Plus 2 GeneChips and scanned according to protocol (Affymetrix Santa Clara, Calif.). Raw expression values were pre-processed using robust multichip averaging (RMA), mean-centering standardization and log 2 transformation (Partek Inc., St. Louis, Mo.) for prediction analyses.

3. Prediction of Myocardial Ischemia

Prediction analyses were performed using linear discriminant analysis (Partek). The 26 gene profile was used to predict ischemia in patients with acute myocardial infarction. The 26 gene profile prediction model was developed on patients with and without cerebral ischemia. The prediction model was applied to patients with acute myocardial infarction to predict ischemia (Table 1). The prediction models assign a probability of belonging to ischemia or non-ischemia group based on the pattern of gene expression.

Results for Predicting Myocardial Ischemia

The demographic and clinical features of the 17 subjects with myocardial ischemia are summarized in Table 1. The average age was 57.4 years (SD 14.2) and 64.7% were male. The cohort was of mixed race and ethnicity with 64.7% of Caucasian race. Hypertension was present in 82.3%, hyperlipidemia in 58.8%, diabetes in 58.8%. Of the 17 subjects with myocardial infarction, 15 were predicted to have ischemia. This results in an 88.2% sensitivity to diagnose myocardial ischemia using the 26 gene expression profile.

TABLE 8

Characteristics of the 17 myocardial infarction subjects studied, and results of the prediction using the 26 gene expression profile.

| Characteristic | Myocardial Ischemia (n = 17) |
|---|---|
| % Correctly Predicted by 26 gene model | 88.2% (15/17) |
| Age yrs (SD) | 57.4 (14.2) |
| Gender male n (%) | 11 (64.7%) |
| Caucasian n (%) | 11 (64.7%) |
| Hypertension n (%) | 14 (82.3%) |
| Diabetes n (%) | 10 (58.8%) |
| Hyperlipidemia n (%) | 10 (58.8%) |

Example 3

Use of Biomarkers for Predicting and/or Diagnosing Pulmonary Ischemia

Methods for Predicting Pulmonary Embolism
1. Study Patients

Patients with acute pulmonary embolism were enrolled from the University of California Davis. The institutional review board at each site approved the study protocol and written informed consent was obtained from each patient. Patients with myocardial infarction were >18 years of age, and had acute myocardial ischemia. Pulmonary embolism was determined by study physician based on medical history, D-dimer, bloodwork, pulmonary spiral CT scan, and ventilation perfusion scan. All patients had standardized clinical evaluations. Blood samples were drawn into PAXgene tubes (PreAnalytiX, Hilden, Germany) within 100 hours of pulmonary ischemia onset. A total of 3 subjects were analyzed using the 26 gene expression profiles.

2. Sample Processing

Blood was collected by venipuncture into PAXgene tubes (PreAnalytiX, Germany). Samples were stored frozen and then processed at the same time to minimize technical variation. Total RNA was isolated according to protocol (PAXgene blood RNA kit; Pre-AnalytiX) and analyzed for quality using Agilent 2100 Bioanalyzer and quantity by Nano-drop. Reverse transcription, amplification, and sample labeling were carried out using Nugen's Ovation Whole Blood reagents (Nugen Technologies, San Carlos, Calif.). Each RNA sample was hybridized to Affymetrix Genome U133 Plus 2 GeneChips and scanned according to protocol (Affymetrix Santa Clara, Calif.). Raw expression values were pre-processed using robust multichip averaging (RMA), mean-centering standardization and log 2 transformation (Partek Inc., St. Louis, Mo.) for prediction analyses.

3. Prediction of Myocardial Ischemia

Prediction analyses were performed using linear discriminant analysis (Partek). The 26 gene profile was used to predict ischemia in patients with acute pulmonary embolism. The 26 gene profile prediction model was developed on patients with and without cerebral ischemia. The prediction model was applied to patients with acute pulmonary ischemia to predict ischemia (Table 9). The prediction models assign a probability of belonging to ischemia or non-ischemia group based on the pattern of gene expression.

Results for Predicting Pulmonary Embolism

The demographic and clinical features of the 3 subjects with pulmonary embolism are summarized in Table 9. The average age was 51.0 years (SD 17.1) and 66.7% were male. The cohort was of mixed race and ethnicity with 66.7% of Caucasian race. Of the 3 subjects with pulmonary embolism, all 3 were predicted to have ischemia. This results in a 100% sensitivity to diagnose pulmonary ischemia using the 26 gene expression profile in the 3 subjects studied.

Table 2: Characteristics of the 3 subjects with pulmonary embolism studied, and results of the prediction using the 26 gene expression profile.

TABLE 9

Characteristics of the 3 subjects with pulmonary embolism studied, and results of the prediction using the 26 gene expression profile.

| Characteristic | Pulmonary Embolism (n = 3) |
|---|---|
| % Correctly Predicted by 26 gene model | 100% (3/3) |
| Age yrs (SD) | 51.0 (17.1) |
| Gender male n (%) | 2 (66.7%) |
| Caucasian n (%) | 2 (66.7%) |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A kit comprising a microarray attached to nucleic acids that hybridize to ischemia biomarkers comprising UBE2J1, ELAVL3, FCGR2B, BLVRA, JMJD6, DDAH2, PTRH2, CARD16, CAV1, ZNF608, NDUFB3, SLC22A4, PCMT1, CACNA1A, CASP1, LOC100129105, AK5, DIP2A, ETS1, CCND3, GNE, BCL9L, SPATA5 and LBH, wherein the microarray comprises 1000 or fewer hybridizing nucleic acids, and further comprising buffers, salts and/or other reagents to facilitate amplification and/or detection reactions for determining the expression levels of ischemia biomarkers.

2. The kit of claim 1, wherein the microarray is further attached to nucleic acids that hybridize to ischemia biomarkers comprising AIM2, NEIL2, PGS1, C14orf101, DNAH17, ZEB2, WIT1, MMP19, FOXK1, LOC203274, APBA2, ANXA3, FKBP15, SPATA4, LTBR, N4BP2L2, RAB27A, NUCKS1, TBC1D10A, CARD16///CASP1, IGFBP5, RAB27A, CNIH4, NPTXR, CASP5, TLR10, GLG1, SHOX2, HNRNPH2, APBB1, ZMYND11, FLJ39051, ZNF609, TAF3, DRAM1, LTB, CAPN5, WHAMML1///WHAMML2, FCGR1B, CYTH4 and FMNL3.

3. The kit of claim 1, wherein the microarray is further attached to nucleic acids that hybridize to ischemia biomarkers comprising ADM, ALDH6A1, ALS2CL, ANKRD22, ATXN2L, BAGE, BAZ1B, BTC, C13orf16, C16orf35, C20orf196, C9orf66, CAND1, CAPN5, CARD16, CLTC, DCAF16, EIF3B, ENTPD5, ERMN, FUS, FUS///NR1H3, G3BP1, GCAT, GRM5, GSTM1, GSTM2, GUSBL2, GYPA, HCFC1, hCG 1749898, HCN1, HELLS, HERC1, HNRNPUL2, HS3ST3A1, HSPA6, IFT80, IQGAP3, IRF7, KIAA0391, KIAA1659, KIAA1919, LIFR, LOC100129656, LOC100293532, LOC440104, LPIN1, MAP2K7, MBNL2, MED1, METTL3, NAPEPLD, NMU, NPR3, OSTCL, OVOL2, PLSCR1, PRDX6, PYGB, RANBP10, RASAL2, RBM6, SAMD9L, SHOX, SIX3, SLC37A3, SLC3A1, SMARCC2, SMURF2, SRGAP1, TAPBP, TLR6, TPP2, TWIST1, UNC84A, VTI1A, XRCC4, YARS, YBX1///YBX1P2, ZBP1, ZNF354A and ZNF652.

4. The kit of claim 1, wherein the microarray is further attached to nucleic acids that hybridize to stably expressed endogenous reference biomarkers comprising USP7, MAPRE2, CSNK1G2, SAFB2, PRKAR2A, PI4 KB, CRTC1, HADHA, MAP1LC3B, KAT5, CDC2L1///CDC2L2, GTSE1, TCF25, CHP, LRRC40, hCG_2003956///LYPLA2///LYPLA2P1, DAXX, UBE2NL, EIF1, KCATF1, PRKRIP1, CHMP4A, TMEM184C, TINF2, PODNL1, FBXO42, LOC441258, RRP1, C10orf104, ZDHHC5, C9orf23, LRRC45, NACC1, LOC100133445///LOC115110 and PEX16.

5. The kit of claim 1, wherein the microarray is further attached to nucleic acids that hybridize to ischemia biomarkers comprising FAT3, GADL1, CXADR, RNF141, CLEC4E, TIMP2, ANKRD28, TMM8A, PTPRD, CCRL1, FCRL4, DLX6, GABRB2, GYPA, PHTF1, CKLF, CKLF, RRAGD, CLEC4E, CKLF, FGD4, CPEB2, LOC100290882, UBXN2B, ENTPD1, BST1, LTB4R, F5, IFRD1, KIAA0319, CHMP1B, MCTP1, VNN3, AMN1, LAMP2, FCHO2, ZNF608, REM2, QKI, RBM25, FAR2, ST3GAL6, HNRNPH2, GAB1, UBR5, VAPA, MCTP1, SH3GL3, PGM5, CCDC144C///LOC100134159, LECT2, SHOX, TBX5, SPTLC3, SNIP, RBMS3, P704P, THSD4, SNRPN, GLYATL1, DKRZP434L187, OVOL2, SPIB, BXDC5, UNC5B, ASTN2, FLJ35934, CCDC144A, ALDOAP2, LDB3, LOC729222///PPFIBP1, HNRNPUL2, ELAVL2, PRTG, FOXA2, SCD5, LOC283027, LOC344595, RPL22, LOC100129488 and RPL22.

6. The kit of claim 1, wherein the microarray is further attached to nucleic acids that hybridize to ischemia biomarkers comprising IRF6, ZNF254, GRM5, EXT2, AP3S2, PIK3C2B, ARHGEF5, COL13A1, PTPN20A///PTPN20B, LHFP, BANK1, HLA-DOA, EBF1, TMEM19, LIIFP, FCRL1, OOEP, LRRC37A3, LOC284751, CD46, ENPP2, C19orf28, TSKS, CHURC1, ADAMTSL4, F1140125, CLEC18A, ARHGEF12, C16orf68, TFDP1 and GSTK1.

7. The kit of claim 1, wherein the microarray is further attached to nucleic acids that hybridize to ischemia biomarkers comprising NT5E, CLASP2, GRM5, PROCR, ARHGEF5, AKR1C3, COL13A1, LHFP, RNF7, CYTH3, EBF1, RANBP10, PRSS35, C12orf42, LOC100127980, FLJ31945, LOC284751, LOC100271832, MTBP, ICAM4, SHOX2, DOPEY2, CMBL, LOC146880, SLC20A1, SLC6A19, ARHGEF12, C16orf68, GIPC2 and LOC100144603.

8. The kit of claim 1, wherein the microarray is further attached to nucleic acids that hybridize to ischemia biomarkers comprising SMC1A, SNORA68, GRLF1, SDC4, HIPK2, LOC100129034, CMTM1, TTC7A, LRRC43, MIF///SLC2A11, PER3, PPIE, COL13A1, DUSP16, LOC100129034, BRUNOL6, GPR176, C6orf164 and MAP3K7IP1.

9. The kit of claim 1, wherein the microarray is further attached to nucleic acids that hybridize to ischemia biomarkers comprising HLA-DQA1, FLJ13773, RASEF, CALM1, QKI, TTC12, CCL3///CCL3L1///CCL3L3, CCDC78, PRSS23, LAIR2, C18orf49, MPZL3, UTS2, FAM70B, UTS2, LOC254128, LGR6, IL8, CHML, STX7, PROCR, VAPA, LAG3, OASL, LOC100132181, HLA-DRB4, CCL2, UGCG, PDXDC1, ALS2CR11, SCAND2, GBP4, RUNX3, LRRC8B, TSEN54, UBA7, STK4, FAM179A, TGFBR3, CCDC114, GTF2H2, AKAP9, BNC2, BZRAP1, CCL4, CHST2, CSF1, ERBB2, GBR56, GRAMD3, GRHL2, GRK4, IT1H4, KIAA1618, LOC147646, LOC150622, LOC161527, PLEKHF1, PRKD2, RGNEF, SESN2, SLAMF7, SPON2, STAT1, SYNGR1, TRX21, TMEM67, TUBE1, ZNF827, AGFG1, BTG1, CFDP1, CNPY2, FAM105A, GATM, GTF2H2, IGHG1, IL18RAP, N4BP2, PHACTR1, QK1, RTKN2, SLC16A1, SOCS1, SPAG17, ST6GALNAC1, STK17B, STT3B, STX16, TBC1D12, TRIM4, UACA, and WHAMML2.

10. The kit of claim 1, further comprising one or more reaction vessels that have aliquots of some or all of reaction components to facilitate amplification and/or detection reactions for determining the expression levels of ischemia biomarkers.

11. The kit of claim 1, further comprising sample processing cartridges or other vessels that allow for the containment, processing and/or amplification of samples in the same vessel.

* * * * *